(12) United States Patent
Freeman et al.

(10) Patent No.: US 11,461,936 B2
(45) Date of Patent: Oct. 4, 2022

(54) WEARABLE IMAGE MANIPULATION AND CONTROL SYSTEM WITH MICRO-DISPLAYS AND AUGMENTATION OF VISION AND SENSING IN AUGMENTED REALITY GLASSES

(71) Applicant: Raytrx, LLC, Tulsa, OK (US)

(72) Inventors: Michael Hayes Freeman, Tulsa, OK (US); Richard C. Freeman, Tulsa, OK (US); Mitchael C. Freeman, Sapulpa, OK (US); Chad Boss, Tulsa, OK (US); Jordan Boss, Tulsa, OK (US)

(73) Assignee: Raytrx, LLC, Tulsa, OK (US)

( * ) Notice: Subject to any disclaimer, the term of this patent is extended or adjusted under 35 U.S.C. 154(b) by 601 days.

(21) Appl. No.: 16/511,202

(22) Filed: Jul. 15, 2019

(65) Prior Publication Data
US 2019/0385342 A1  Dec. 19, 2019

Related U.S. Application Data

(63) Continuation-in-part of application No. 15/073,144, filed on Mar. 17, 2016, now Pat. No. 9,955,862, and
(Continued)

(51) Int. Cl.
*G06T 11/00* (2006.01)
*A61B 3/113* (2006.01)
*G06F 3/01* (2006.01)

(52) U.S. Cl.
CPC .............. *G06T 11/00* (2013.01); *A61B 3/113* (2013.01); *G06F 3/017* (2013.01)

(58) Field of Classification Search
CPC ............. G06T 19/006; G06T 2219/024; G06T 15/503; G06T 17/05; G06T 19/00;
(Continued)

(56) References Cited

U.S. PATENT DOCUMENTS 7,639,208 B1  12/2009  Ha et al.
8,135,227 B2   3/2012  Lewis et al.
(Continued)

FOREIGN PATENT DOCUMENTS

KR  1020180068351  6/2018

OTHER PUBLICATIONS

KIPO, "International Search Report", dated Jun. 16, 2016, Published in: WO.
(Continued)

*Primary Examiner* — Brandi N Thomas
(74) *Attorney, Agent, or Firm* — Head, Johnson, Kachigian & Wilkinson, PC

(57) ABSTRACT

A wearable mixed reality system comprising a camera input system, and image projection system capable of being worn by a user, and a processor in communication with the camera input system and the image projection system. The processor may be capable of receiving a real-world image from the camera input system and simultaneously displaying at least a portion of the real-world image and an augmented image on the image projection system such that a user views the portion of the real-world image and the augmented image simultaneously.

17 Claims, 31 Drawing Sheets

Related U.S. Application Data a continuation-in-part of application No. 15/940,561, filed on Mar. 29, 2018, now Pat. No. 10,111,583, and a continuation-in-part of application No. 16/173,719, filed on Oct. 29, 2018, now Pat. No. 10,874,297, and a continuation-in-part of application No. 15/962,661, filed on Apr. 25, 2018.

(60) Provisional application No. 62/697,854, filed on Jul. 13, 2018, provisional application No. 62/134,422, filed on Mar. 17, 2015, provisional application No. 62/489,801, filed on Apr. 25, 2017.

(58) Field of Classification Search
CPC ....... G06T 2215/16; G06T 7/73; G06T 17/00; G06T 15/00; G06T 11/00; G06T 15/205; G06T 19/20; G06T 2207/30201; G06T 5/003; G06T 7/70; G06T 7/74; G06T 1/0007; G06T 15/04; G06T 15/10; G06T 19/003; G06T 2207/10016; G06T 2207/30244; G06T 7/564; G06T 7/579; G06T 11/001; G06T 15/08; G06T 15/20; G06T 15/50; G06T 17/20; G06T 2200/21; G06T 2207/10012; G06T 2207/10028; G06T 2207/30204; G06T 2207/30248; G06T 2210/08; G06T 2210/41; G06T 3/0056; G06T 5/00; G06T 5/002; G06T 5/006; G06T 7/13; G06T 7/529; G06T 7/536; G06T 1/20; G06T 11/40; G06T 11/60; G06T 13/40; G06T 15/005; G06T 15/06; G06T 15/506; G06T 17/10; G06T 2200/08; G06T 2200/24; G06T 2200/28; G06T 2207/10021; G06T 2207/10121; G06T 2207/20084; G06T 2207/30008; G06T 2207/30168; G06T 2207/30196; G06T 2207/30208; G06T 2210/16; G06T 2219/004; G06T 2219/2016; G06T 2219/2021; G06T 3/00; G06T 3/0062; G06T 3/0093; G06T 7/0002; G06T 7/0004; G06T 7/10; G06T 7/11; G06T 7/174; G06T 7/194; G06T 7/20; G06T 7/246; G06T 7/254; G06T 7/269; G06T 7/50; G06T 7/521; G06T 7/55; G06T 7/593; G06T 7/62; G06T 7/80; G06T 7/85; G06T 9/00; G06F 3/011; G06F 3/012; G06F 1/163; G06F 3/017; G06F 3/013; G06F 40/51; G06F 3/0425; G06F 3/016; G06F 3/147; G06F 3/0484; G06F 3/167; G06F 3/0304; G06F 3/01; G06F 3/04815; G06F 3/0346; G06F 3/00; G06F 3/005; G06F 3/14; G06F 17/00; G06F 2203/04806; G06F 3/002; G06F 30/00; G06F 16/29; G06F 16/954; G06F 21/31; G06F 3/0481; G06F 3/0485; G06F 3/16; G06F 3/162; G06F 3/165; G06F 40/169; G06F 1/1686; G06F 1/1688; G06F 1/1694; G06F 1/1698; G06F 1/3203; G06F 1/325; G06F 1/3259; G06F 16/9027; G06F 16/907; G06F 21/6245; G06F 2111/04; G06F 2203/04101; G06F 3/0321; G06F 3/03545; G06F 3/0482; G06F 3/0483; G06F 3/0488; G06F 3/04883; G06F 3/05; G06F 3/1423; G06F 3/1454; G06F 30/12; G06F 30/17; G06F 40/58; G02B 27/0172; G02B 2027/0138; G02B 2027/014; G02B 2027/0178; G02B 27/017; G02B 27/0093; G02B 2027/0187; G02B 2027/0141; G02B 27/0179; G02B 2027/0134; G02B 2027/0181; G02B 2027/0183; G02B 30/25; G02B 21/368; G02B 2027/011; G02B 2027/0123; G02B 2027/013; G02B 2027/0147; G02B 2027/0174; G02B 27/0025; G02B 27/0101; G02B 30/00; G02B 5/18; G02B 5/20; G02B 2027/0127; G02B 2027/0161; G02B 26/101; G02B 27/01; G02B 27/0176; G02B 3/0037; G02B 3/0068; G02B 6/3504; G02B 1/002; G02B 17/06; G02B 19/0047; G02B 2003/0093; G02B 2027/0105; G02B 2027/0112; G02B 2027/0118; G02B 2027/0125; G02B 2027/0159; G02B 2027/0185; G02B 21/365; G02B 23/10; G02B 23/12; G02B 26/004; G02B 26/02; G02B 26/06; G02B 26/0816; G02B 26/10; G02B 26/105; G02B 26/124; G02B 26/125; G02B 27/0075; G02B 27/0103; G02B 27/0961; G02B 27/0972; G02B 27/1066; G02B 27/141; G02B 27/145; G02B 27/30; G02B 3/00; G02B 3/08; G02B 3/14; G02B 30/27; G02B 5/045; G02B 6/0011; G02B 6/005; G02B 6/0055; G02B 6/2706; G02B 6/4204; G02B 6/423

See application file for complete search history.

(56) References Cited

U.S. PATENT DOCUMENTS

| | | |
|---|---|---|
| 8,311,328 B2 | 11/2012 | Spruck |
| 8,350,898 B2 | 1/2013 | Chang et al. |
| 8,494,298 B2 | 7/2013 | Lewis et al. |
| 8,771,805 B2 | 7/2014 | Laude et al. |
| 8,798,756 B2 | 8/2014 | McClure et al. |
| 8,812,120 B2 | 8/2014 | Greenberg et al. |
| 8,831,734 B2 | 9/2014 | Nanduri et al. |
| 8,831,745 B2 | 9/2014 | Hung et al. |
| 8,874,224 B2 | 10/2014 | Greenberg et al. |
| 8,874,239 B2 | 10/2014 | Greenberg et al. |
| 8,886,329 B2 | 11/2014 | Greenberg et al. |
| 8,912,979 B1 | 12/2014 | Gomez |
| 8,934,983 B2 | 1/2015 | Greenberg et al. |
| 8,954,157 B2 | 2/2015 | Faraji et al. |
| 8,976,086 B2 | 3/2015 | Hilkes |
| 9,002,462 B2 | 4/2015 | McClure et al. |
| 9,042,985 B2 | 5/2015 | Marsh et al. |
| 9,044,590 B2 | 6/2015 | Greenberg et al. |
| 9,044,591 B2 | 6/2015 | Greenberg et al. |
| 9,050,468 B2 | 6/2015 | Greenberg et al. |
| 9,061,150 B2 | 6/2015 | Greenberg et al. |
| 9,072,888 B2 | 7/2015 | Greenberg et al. |
| 9,072,900 B2 | 7/2015 | Caspi et al. |
| 9,078,739 B2 | 7/2015 | Greenberg et al. |
| 9,084,895 B2 | 7/2015 | Greenberg et al. |
| 9,089,690 B2 | 7/2015 | Greenberg et al. |
| 9,089,701 B2 | 7/2015 | Zhou et al. |
| 9,089,702 B2 | 7/2015 | Dorn et al. |
| 9,095,709 B2 | 8/2015 | McClure et al. |
| 9,095,710 B2 | 8/2015 | Horsager et al. |
| 9,095,722 B2 | 8/2015 | Meeh et al. |
| 9,097,891 B2 | 8/2015 | Border et al. |
| 9,955,862 B2 | 5/2018 | Freeman et al. |
| 10,345,768 B2 | 7/2019 | Fullam et al. |
| 2005/0168569 A1 | 8/2005 | Igarashi et al. |
| 2007/0121070 A1 | 5/2007 | Alster et al. |
| 2009/0123036 A1 | 5/2009 | Huang et al. |
| 2010/0079356 A1 | 4/2010 | Hoellwarth |
| 2010/0277471 A1 | 11/2010 | Beato et al. |
| 2011/0043644 A1 | 2/2011 | Munger et al. |

(56) References Cited

U.S. PATENT DOCUMENTS

| | | |
|---|---|---|
| 2012/0068913 A1 | 3/2012 | Bar-Zeev et al. |
| 2012/0200595 A1 | 8/2012 | Lewis et al. |
| 2013/0155507 A1 | 6/2013 | Ryu et al. |
| 2013/0162673 A1 | 6/2013 | Bohn |
| 2013/0194254 A1 | 8/2013 | Miyoshi et al. |
| 2013/0215147 A1 | 8/2013 | Hilkes et al. |
| 2013/0329190 A1 | 12/2013 | Lewis et al. |
| 2013/0335543 A1 | 12/2013 | Hilkes et al. |
| 2014/0214122 A1 | 7/2014 | Nanduri et al. |
| 2014/0232645 A1 | 8/2014 | Ali et al. |
| 2014/0243971 A1 | 8/2014 | Pugh et al. |
| 2015/0084841 A1 | 3/2015 | Hilkes |
| 2015/0193984 A1 | 7/2015 | Bar-Zeev et al. |
| 2015/0355481 A1 | 12/2015 | Hilkes et al. |
| 2015/0362733 A1 | 12/2015 | Spivack |
| 2015/0378074 A1 | 12/2015 | Kollin et al. |
| 2016/0027216 A1 | 1/2016 | da Veiga et al. |
| 2016/0037849 A1 | 2/2016 | Shearman et al. |
| 2016/0055822 A1 | 2/2016 | Bell |
| 2016/0062636 A1* | 3/2016 | Jung .................... G06F 3/04817 715/762 |
| 2016/0196694 A1 | 7/2016 | Lindeman |
| 2016/0262608 A1* | 9/2016 | Krueger ................. G16H 50/20 |
| 2016/0267720 A1 | 9/2016 | Mandella et al. |
| 2016/0270648 A1 | 9/2016 | Freeman et al. |
| 2016/0377871 A1 | 12/2016 | Kress et al. |
| 2016/0379593 A1 | 12/2016 | Borenstein et al. |
| 2017/0010469 A1 | 1/2017 | Samec et al. |
| 2017/0236332 A1 | 8/2017 | Kipman et al. |
| 2017/0242253 A1 | 8/2017 | Benesh |
| 2017/0323615 A1 | 11/2017 | Hazra et al. |
| 2018/0045964 A1 | 2/2018 | Jones et al. |
| 2018/0046179 A1* | 2/2018 | Choi ..................... B64C 39/024 |
| 2018/0249151 A1* | 8/2018 | Freeman ............... A61B 3/0025 |
| 2019/0049949 A1* | 2/2019 | Moeller ................ B64C 39/024 |
| 2019/0339528 A1 | 11/2019 | Freeman et al. |

OTHER PUBLICATIONS

KIPO, "International Search Report", dated Jul. 31, 2018, Published in: WO.

KIPO, "International Search Report", dated Oct. 28, 2019, Published in: WO.

KIPO, "International Search Report", dated Nov. 11, 2019, Published in: WO.

Loshin et al., "The Programmable Remapper: Clinical Applications for Patients With Field Defects", "Optometry and Vision Science", Nov. 4, 1988, pp. 389-395, vol. 66, No. 6.

Wrobleswki et al., "Testing of Visual Field With Virtual Reality Goggles in Manual and Visual Grasp Modes", "http://www.hindawi.com/journals/bmri/2014/206082", Jan. 1, 2014, pp. 1-7, vol. 2014, No. 206082, Publisher: Biomed Research International.

* cited by examiner

ORIGINAL LINE

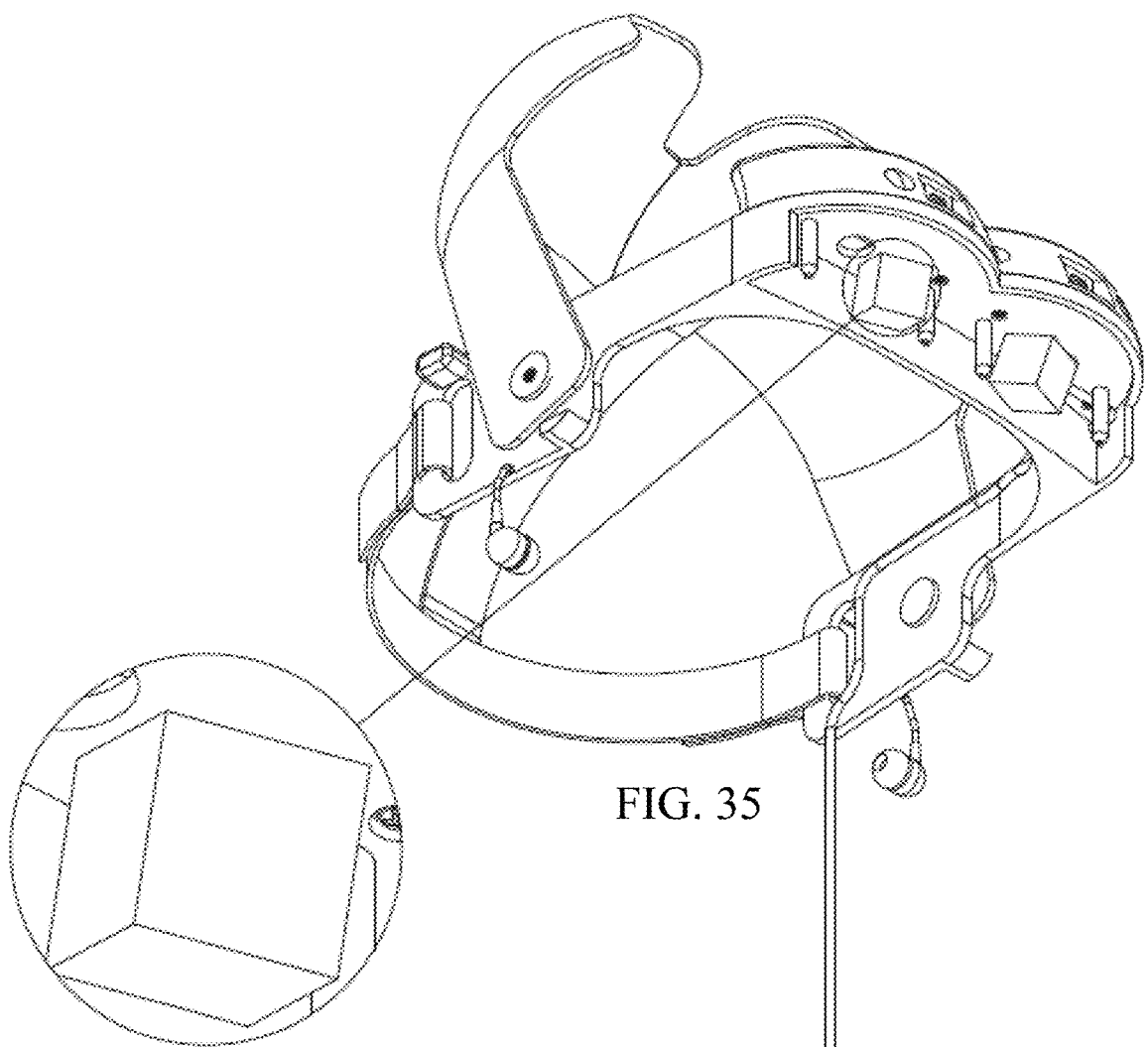
FIG. 35
FIG. 35a
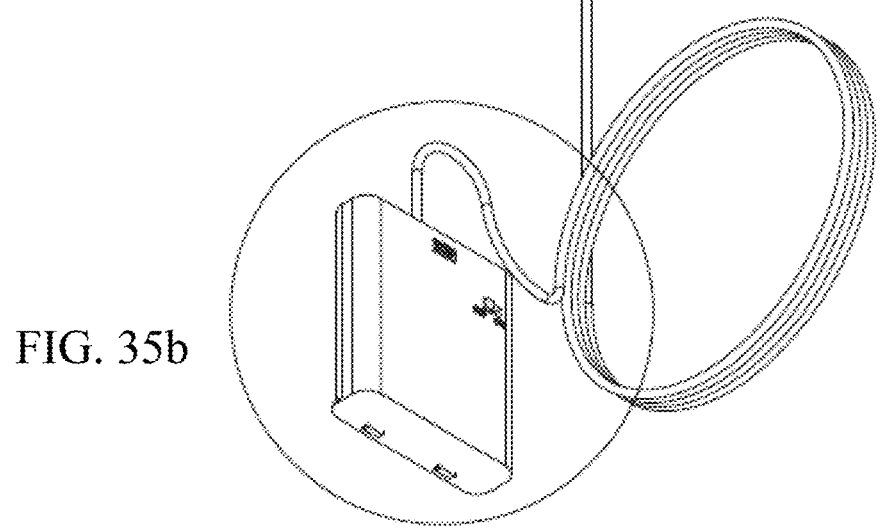
FIG. 35b

WEARABLE IMAGE MANIPULATION AND CONTROL SYSTEM WITH MICRO-DISPLAYS AND AUGMENTATION OF VISION AND SENSING IN AUGMENTED REALITY GLASSES

CROSS REFERENCE

This application is based on and claims priority to U.S. Provisional Patent Application No. 62/697,854 filed Jul. 13, 2018. This application is also a continuation-in-part of U.S. patent application Ser. No. 15/073,144 filed Mar. 17, 2016, which issued on May 1, 2018 as U.S. Pat. No. 9,955,862, U.S. patent application Ser. No. 15/940,561 filed Mar. 29, 2018, which issued on Oct. 30, 2018 as U.S. Pat. No. 10,111,583, and U.S. patent application Ser. No. 16/173,719 filed Oct. 29, 2018, all of which claim the benefit of U.S. Provisional Patent Application No. 62/134,422 filed Mar. 17, 2015; and of U.S. patent application Ser. No. 15/962,661 filed Apr. 25, 2018, which claims the benefit of U.S. Provisional Patent Application No. 62/489,801 filed Apr. 25, 2017. All are incorporated herein by reference.

BACKGROUND OF THE INVENTION

Field of the Invention

The present invention relates generally to improvements in augmented reality (AR) glasses, including using such glasses for medical purposes for the correction of vision defects, and more particularly to a system and methods for compensating for visual defects, for detecting the vision defects, capturing an image, modifying the image for correcting the visual defect, and displaying a modified image for that correction, and also for the correction of what prescription glasses would otherwise do. This present invention also incorporates novel hardware and software applications related to the invention, including the application of smart contact lenses.

Description of the Related Art

Macular degeneration (AMD), macular hole, and other FOV (Field of Vision) related blindness or vision defect conditions, such as central macular scar, histoplasmosis, end-stage glaucoma, Stargardt's disease, central serous retinopathy, myopic macular degeneration, diabetic macular edema, cystoid macular edema, macular holes, macular atrophy, central macular scar, histoplasmosis, macular hole, anterior ischemic optic neuropathy, and retinitas pigmentosa, are often irreversible. The impact to a patient's life due to the loss of a portion of their vision is enormous, including degraded and loss of the ability to read, watch TV, and see computer screens. Some of the conditions can be halted, and fortunately leaves some of the vision intact, and in the case of macular hole or macular degeneration, the peripheral vision remains intact; while in the case of retinitas pigmentosa the peripheral vision is lost and only "tunnel vision" remains. In each of these cases, augmentation of a projected image with pixel manipulation together with real world visual information can aid the patient in recovering some or all of their sight.

There have been previous attempts to augment the sight of a patient whose other sight is defective or otherwise impaired, or otherwise compensate for the patient's damaged or impaired sight. For instance, previous efforts have focused on devices that increase the intensity or contrast of the patient's sight and/or increase the magnification of the image seen by the patient while wearing virtual reality goggles, which block all other external sight. These attempts have not been very effective, are bulky and expensive, and are presented only in an immersive, occluded, ensconced virtual reality (VR) type of viewing environment, meaning that the patient's existing real-world sight is restricted and the patient can only see what is projected onto that display, while everything else is blocked out. Thus, the patent using these VR type goggles loses the ability to see what is actual around him or her with any remaining sight. This is a disadvantage because a person wearing VR type googles and some AR glasses, which use wave guides that necessarily mechanically restrict the peripheral view, cannot completely see how to move in their environment, walk, or navigate steps or the immediate environment around him or her, so that the display is only potentially useful when sitting or remaining stationary. This causes any user to have to remove the goggles from their eyes to be able to receive actual visual clues from the real-world environment; a serious limitation of this type of application. Another limitation with these type VR goggles or AR glasses is that they do not bear an accurate relation to the real world a person might see, as the field of view is too small, and a patient wearing these type of VR goggles or AR glasses may experience motion sickness versus real world vision, due to blur, whirr, and latency.

Since the peripheral receptors in the retina are usually still functioning, it is the purpose of this invention, in one embodiment for a medical application of AR glasses, to stretch, skew, and manipulate the image being projected on the eye to avoid the macula, and be directed to the retina's peripheral receptors. In this way, the entire image is projected on the functioning retinal receptors, and any involvement of the macula is avoided. The method taught in this invention is how to create a matrix distortion of the entire image and project it onto the periphery of the eye, while avoiding the macula.

However, by combination of hardware, software, and firmware, as taught herein, the patient, by using "see through" glasses or lenses that provide a wide field of vision, upon which an augmented image can also be displayed, can have both real world and augmented visual information which corrects for the vision defect suffered delivered to the eyes. This is an improvement to the existing art and a new "mixed reality" wearable invention.

Under the teaching herein, the visually impaired user can be introduced to both real world visual information and augmented information, at the same time, such that together the two separate inputs provide a "mixed reality" vision. This can be accomplished, as taught herein, with virtually no latency, such that the augmentation enhances the user's remaining real-world eyesight experience. Under this patent, the user can still see some real world visual information with their peripheral eyesight so that the user can move, walk, and navigate his or her immediate surroundings with as much surety and safety as the user would otherwise have, and at the same time rely on the augmented reality of an augmented pixel/image moved video feed.

The present invention is aimed at one or more of the problems identified above.

SUMMARY OF THE INVENTION

In general, in a first aspect, the invention relates to a vision corrective wearable device which, in its preferred embodiment, uses a mixed reality type of glasses/lenses together with new software and hardware to achieve the desired effect. This invention may manipulate an image or video to avoid unsighted areas, such as the damaged areas that result with macular degeneration or macular hole, and project the image on the glasses/lenses where it can be viewed by the next-nearest sighted areas of the eye. It may also merge such augmented video back into real world images, which can be viewed alongside the real-world images received without video by, typically, the periphery of the naked eye. It may also correct for nearsightedness and farsightedness at the same time as the correction of the central vision.

In another aspect of this invention, there is no manipulation of the pixels for eye correction; rather, an AR headset may provide a computer-mediated video shown on a display screen such that the wearer sees both the real world and the augmented video at the same time. In this aspect of the invention, such features as voice/speech recognition, gesture recognition, obstacle avoidance, an accelerometer, a magnetometer, a gyroscope, GPS, special mapping as used in simultaneous localization and mapping (SLAM), cellular radio frequencies, Wi-Fi frequencies, Bluetooth and Bluetooth light connections, infrared cameras, and other light, sound, movement, and temperature sensors may be employed, as well as infrared lighting, eye-tracking, and dynamic opacity, as set forth herein.

The mixed reality headset described herein may be used for medical, commercial, industrial, gaming, drone control, app experience, and military applications, to name a few.

It must be remembered that the entire retina is the light and color sensitive tissue that lines the inside of the eye. As such, the retina functions in a manner similar to film in a camera; hence, this invention may supplement the retina's camera effect by providing an augmented, mixed reality duality of vision to the user using both one or more external cameras and a display, as well as the eye's natural vision. Because it is important to make the augmented video or image hit as many cones as possible, the higher the rate of resolution, the better. In addition, in a preferred embodiment of the invention, the display may cover at least 50 degrees of the user's field of vision (FOV) or greater, although the invention will also work with a lesser FOV.

Thus, in one aspect of the invention, the image to be displayed may cover the entire 120 degrees of normal eye vision, while in another aspect of the invention, the image may be displayed on 90 degrees, 80 degrees, or 50 degrees FOV. The greater the FOV of the manipulated video display, the better reintegration of the real world in the exterior periphery of the eye's vision.

The image to be displayed may be intended to be displayed on all or a portion of the lenses of the mixed reality glasses, goggles, or other display techniques, where is extant both video and normal vision.

Part of the duality of the vision may be the real-world vision that the user sees where there is no augmented modified video, typically on the periphery of the lenses of the glasses and beyond that, simply the user's own unrestricted vision. The other portion of the duality of vision may be the augmented, modified video or picture which is typically, in the case of macular degeneration, focused on the portion of the eye closest to the central vision, concentrating manipulated pixels and images onto areas that are still sighted and avoiding areas that are unsighted. Together, these may make up a mixed reality augmented reality vision which may help correct for the defect of eye diseases like macular degeneration, all of which eye diseases are referred to herein sometimes as "defects" or "deficits".

In its natural state, the optical elements in the eye focus an image onto the retina of the eye using the lens, initiating a series of chemical and electrical events within the retina. Nerve fibers within the retina receive these signals and send electrical signals to the brain, which then interprets these signals as visual images. In fact, all of us "see" an image upside down, since the eye bends the image through the lens, and the brain has the unique ability to "upright" the image in brain implemented natural simulation. This invention may use this natural "simulation" created by the brain to "see" a whole picture or video, without any part missing, when in actuality there is a portion of the lens that does not display an image.

Thus, this invention may also employ the "brain-stitching" theory behind the natural blind spot, scotoma, or punctum caecum, which naturally exist in every human's eye. This naturally occurring "hole" is the place in the visual field that corresponds to the lack of light-detecting photoreceptor cells on the optic disc of the retina where the optic nerve passes through the optic disc. Because there are no cells to detect light on the optic disc, this part of the eye's Field of Vision (FOV) is naturally occurring as unsighted and invisible to the human eye, as no visual information can be captured there. However, it has been recognized for a long time that some process in our brains interpolates the blind spot based on surrounding detail and information from the same eye or the other eye, and "fills-in" the blind spot with visual information so similar that we do not normally perceive the blind spot.

This invention teaches that by removing and displacing pixels or images of pictures or video from a non-sighted portion of a defective macula to the area just surrounding the damaged portion of the macula, the brain will interpret the image as a whole, and dismiss the actual hole that is cut into the picture or video. Computing software and chips may create a modified camera generated display image which corrects for the missing macular portion of the retina by not projecting any video or picture on the unsighted areas, and instead displaying the entire image or video on all remaining sighted areas.

This invention has discovered a new concept for the correction of defects like macular degeneration which supposes and enables the brain-stitching/natural brain simulation theory. It has been proven on one notable patient, Brig. Gen. Richard C. "Dick" Freeman (U.S.A.F. Ret.) who is one of the inventors here and one of the inventors who first invented streaming mobile video. General Freeman had macular degeneration, and upon wearing a device using the invention and its augmentations, could instantly "see" a nose on a face, which, due to the macular degeneration, has not been visible for years. The brain-stitching was, in his case, instant, and did not need to be "learned" by the brain.

Thus, in one embodiment of this invention, there may be up to four distinct "phases" of visual images a user could experience. These four phases are called the image manipulation techniques (IMT) herein. In actuality, the invention may work with less than the four, but the most preferable embodiment involves all four. For instance, with virtual reality googles, only the first and second phases may be necessary. Just these two steps may be applied to mixed reality and augmented reality hardware. However, looking at the preferred embodiment, the example of the four phases is explained.

The first phase of the image manipulation techniques is the "hole" of diverse shapes and sizes, resembling as closely as possible the user/patient's own defect, which is virtually "cut" into the picture or video through software techniques, to be displayed to the lenses for the eyes to view. Here, in this first phase, there may be no video or image display, except what the user might see with the naked eye and with the existing defect.

The second phase IMT is the augmented reality video display, which may include pixel mapping, interpolation, and synthesis. This is the area where the pixels that have been "cut out" of the video or image are repositioned to the nearest adjacent area of the eye. These pixels and subpixels may be repositioned in the area directly around the defective area of the eye, and the brain, like the case of the punctum caecum, fills in the "hole" with the visual information added to the surrounding area. In another embodiment of the invention, the image may be displayed directly onto the eyes through techniques like retinal projection. In another embodiment of the invention, the image may be displayed by virtue of smart contact lenses, which can create a display on a contact lens covering the eye.

This manipulation of pixels or images, whether of a picture or video, may present itself with more than 100% of the visual information which must be displayed onto the immediate adjoining areas of the eye. One method to have more than 100% of the image or video displayed on 100% of the screen may be to interleave the video, rather than have it display progressively, where on one scan the original image is shown, and on the alternative scan the repositioned pixels are shown. In another embodiment, a simple reduction of the image may occur. This may be necessary because a part of the image or video has been "cut out" in software and repositioned on the next adjacent space to the deficit in the eye. In another embodiment, the method to displace and replace more than 100% of the information may be accomplished with pixel mapping and replacement. This pixel mapping and replacement may occur after the camera has acquired the image or video and the buffering begins. This manipulation may take place in a central processing unit (CPU) of a micro circuit, and more specifically in a graphics processing unit (GPU), occasionally called the visual processing unit (VPU). These GPU chips may be specialized electronic circuits designed to rapidly manipulate and compress/decompress video and alter memory to accelerate the creation of images in a frame buffer intended for output to a display device. Speed may be key here, as any latency will be evident in the display to the eye. With proper software, most of the modern GPU's can be configured to have only a one millisecond delay between acquisition of the image or video, manipulation of the pixels, and the display of the video, which the eye can easily accommodate and absorb in the display with little or no effect. The system may load ansler grid data from memory and may generate a shader based on the input ansler grid data. The system may then load the shader into the GPU.

In the field of computer graphics, a shader is a computer program that is used to do shading: the production of appropriate levels of light, darkness, and color within an image, or, in the modern era, also to produce special effects or do video post-processing. Shaders calculate rendering effects on graphics hardware with a high degree of flexibility. Most shaders are coded for a graphics processing unit (GPU), though this is not a strict requirement. Shading languages are usually used to program the programmable GPU rendering pipeline, which has mostly superseded the fixed-function pipeline that allowed only common geometry transformation and pixel-shading functions; with shaders, customized effects can be used. The position, hue, saturation, brightness, and contrast of all pixels, vertices, or textures used to construct a final image can be altered on the fly, using algorithms defined in the shader, and can be modified by external variables or textures introduced by the program calling the shader.

Shaders are used widely in cinema postprocessing, computer-generated imagery, and video games to produce a seemingly infinite range of effects. Beyond just simple lighting models, more complex uses include altering the hue, saturation, brightness, or contrast of an image, producing blur, light bloom, volumetric lighting, normal mapping for depth effects, bokeh, cel shading, posterization, bump mapping, distortion, chroma keying (so-called "bluescreen/greenscreen" effects), edge detection and motion detection, psychedelic effects, and a wide range of others.

However, to accomplish the requisite video compression and manipulation, both the CPU and the GPU may need to be used and functions separated, and an ASIC, which is an application specific integrated circuit, may be used to help combine the necessary CPU and GPU functions. The CPU and the GPU may work together, however, to accomplish the task and may need other parts on a circuit or circuit board to fully perform, such as capacitors, resistors, input/output connectors, circuitry, and the like.

It can be recognized that in many instances, since the area of defect is typically not expressed in a standard form, like an oval or circle, there may also be algorithms that instantly measure how far away a pixel would have to be moved to go upwards, downwards, to the left side or to the right side, or transversely from the original area in which the pixel resides. Thus, a measurement may be taken from the area of defect (non-sighted) to determine which way to move the pixels up, down, to the left or right sideways, or transversely, such as up and left or down and right. The software and algorithms may be programmed to move the pixels to the closest original place where there is sight, whichever way they need to be moved. Thus, two pixels or parts of an image which were originally exactly adjacent to one another on any axis up/down, sideways, or transverse may be moved together one way, or, if one pixel or part of an image is closer to one border than to the other, the pixels may be split with one pixel or image going to its closest border and the other pixel or image going to its closest border. This may be the essence of corrective subpixel mapping and modification.

The cutting of the hole and repositioning of the video or image may be accomplished primarily by stretching the pixels to a larger overall area than the original captured image (i.e. 100° stretches to 120° overall space, but the center 10° is cut out). In this method all the pixels are still there, in relatively the same size and shape, as originally captured and buffered by the camera(s), except either the far edge boundary has been extended or cropped. This method works well with goggles, but not as well with the mixed reality improvements in the technique. Thus, the preferred method in mixed reality corrective glasses (MRCG) is to use pixel mapping, interpolation, and synthesis (PMIS). Under this method, the pixels in the area of the display to be avoided may be mapped, in real or near real time, within or without a buffer, and software algorithms may keep the same shape of the image, but reduce the size of the pixels to subpixels. For example, an image which was, for instance, shown on four pixels may be reduced to be shown on three, two, or just one pixel. The resulting display may have the entire image, but a fewer number of pixels and subpixels may be created. Under this method, pixels may have been reduced to subpixels, which may have been moved in the video according to the software implementation and the shape of the defect. In this way, the area that is moved may not necessarily have to have a specific boundary, like an oval or a circle, but the pixels may be removed from any defect area, no matter how irregular, and repositioned to a sighted area just adjacent. Thus, the idea is not just one where boundaries are created, but where the image or video pixels are moved one by one out of the non-seeing, defect area to another place as close to that unsighted area as possible with the remaining image being likewise transposed to make room for the removed and replaced pixels and image. Thus, the area to be avoided may be very irregular and complex, which makes no difference, as once it is mapped, pixels may be removed from the space where no sight is and placed adjacent as closely to the place on the pixel map as possible, which is described herein as subpixel mapping and placement.

Pixels as used herein may be perceived spaces where subpixel mapping is a recently developed technology involving algorithms to obtain and map the spatial distribution information of area covered within mixed pixels and then reposition them on a smaller or different scale. See, FIG. 25. Algorithms can be applied to pixel-mapped video or image content, and images moved from one location in the video to another. The shape to be avoided may have edges and otherwise not be a homogenous shape, like a circle or oval. In some instances, the pixels or subpixels may be distorted in order to have more than 100% of the image included into 100% of the display space. In this case, the pixels or image may take on a shape which is not a typical pixel square, but can be something besides a square, and often more like a tetrahedron or polyhedron, or shapes like triangles or parallelograms.

Under this method, the classification on a per pixel basis may be established and then reconstituted in a pixel/subpixel format to achieve subpixel mapping for modification. By applying known pixel and subpixel mapping techniques, as well as the ones invented by the inventors here, an image or video can be displayed with augmented pixel/subpixel manipulation and stitching so that a whole image exists, just not in the original place as the camera input originally assigned.

Next is the third phase, where video may be faded back into reality video through stitching or a similar technique, which may be used to merge or combine the second phase with the third phase in steps, where the second phase is phased out and the third phase of real world captured video dominates, and then is the unaltered video feed. In this third phase, direct camera input may be a phased-in re-engagement of the real-world projected image. In the third phase, the second phase image manipulation technique may merge with the third phase image manipulation technique to phase out the over 100% pixel manipulation and may work the other way to reintroduce the image or video back to 100% of what the camera actually acquires as an image. However, in this phase, the video may still be manipulated so as to correct for line-of-sight (to correct for the eye visions versus the camera captured images) and to correct for the epipolar geometry effect of the eyes moving inward and outward/straight.

This third phase software/hardware stitching may be akin to the techniques commonly utilized in 3D video stitching software. It is in phase three where the augmented video may then be returned to an un-modified video of what the user would actually see if the cameras were projecting and displaying raw, unmodified video or images. This raw video may be projected or displayed on the retina or the contacts or lenses of glasses where only a portion of the field of vision is used for phases one through three and the rest of the display area may be reserved for phase four video, where it may be merged by the eye and brain with the real-world vision which is external to phase four.

Further, phase four may be where the user sees with his or her peripheral vision the real world and upon which either the sight through the lenses or beyond the lenses, no video is displayed. This phase may also include any extra peripheral vision that is extant outside of the glasses, lenses, contacts, or retinal projection, and may provide the user with additional real-world cues and images.

Thus, by using phases one through four, a user may experience four distinct image sets, all of which may merge through the brain's natural simulations to create one mixed reality view of the world, which may be corrected for a defect. Thus, on a display of see-through glasses, there may be projected an augmented video, which could be as large as 30 to 50 degrees field of vision. This could be greater or smaller depending on the type of defect and the amount of correction. Outside that augmented video display on the lens may be displayed a video of what the eyes would ordinarily see, but augmented in a phase-in/phase-out of the augmented video.

In another embodiment of the invention, an implanted lens or lenses, akin to the manner of an implanted intraocular lens, may perform some or all of the pixel manipulation by diverting the pixels away from the damaged areas of the macula. This could be done with dual lenses like those used in intraocular lenses for visually impaired patients (IOLVIP or IOL-VIP), which is an intraocular lens system aiming to treat patients with poor central vision due to age related macular degeneration. The IOLVIP procedure involves the surgical implantation of a pair of lenses that magnify and divert the image using the principals of the Galilean telescope. By arranging the lenses, it is possible to direct the image to a different part of the eye than the fovea. In this way, the head-mounted display (HMD), which may be glasses, frame, and headgear (HMD), and/or external display may be calculated to coordinate with the implanted lenses to cut out the image ordinarily displayed where the defect exists and project the full image on the display, which may then be diverted by the implanted lenses and become a full image. This is unlike the IOLVIP lenses that are used now, which only carry a portion of the actual image information.

In one embodiment, this invention may comprise a system having a database, a CPU, a model view controller, a camera intake, a display controller, and a display unit. The model view controller, which may be hardware, firmware, software, memory, microcontroller, state machine, or a combination of any of the foregoing, may be coupled to the database and may be configured to establish a reference to a visual model associated with a user's visual defect; then the one or more cameras may take a picture or video of the actual image, the software may make corrections for the user's visual defect, and the corrected/modified image, which may have been corrected for the user's visual defect, may be displayed.

In summary of the invention, one or more cameras and lenses may assist the user in identifying his or her visual impairment boundaries. This information may then be transferred into a visual modification program, which may augment the displayed video and picture images to displace the part of the image/video within the vision impaired boundaries and remove it to the nearest sighted area. In one embodiment of the invention, the visual modification program may also re-introduce real world images captured by a camera input system (CIS) so that an augmented video segment is displayed on the lenses, wherein the augmented video segment is phased back to a real-world, un-modified video such that the edges of the displayed system are in sync or near sync with the real-world vision seen by the eyes while wearing the HMD. The invention may also include a method to store the modified visual model in the database and to project it on a display. The invention may also include a diagnostic impairment mapping (DIM) system and method to capture information about the area and location of the eye defect, as in mapping an area where macular degeneration has occurred and little or no sight or vision remains. The corrected visual model may include data related to the quality of the user's vision and the manipulation of images and/or pixels or other visual portions of a video or recorded image or images which correct for that user's visual defect. In one embodiment, the corrected image may not be a manipulation of pixels, but rather a mapping of pixels in software/firmware and then a step of correction for the user's visual defect through repositioning of the image onto other pixels or subset of pixels, which are then projected onto the sighted areas of the eye, such that a whole picture or video is shown, but the portion of the eye that is defective is left with no image/video projection.

BRIEF DESCRIPTION OF THE DRAWINGS

Non-limiting and non-exhaustive embodiments of the present invention are described with reference to the following figures, wherein like reference numerals refer to like parts throughout the various views, unless otherwise specified.

FIG. 35 is a diagrammatic illustration of the placement of one or more micro displays for projecting the image onto the lens(s);

FIG. 35a is a diagrammatic illustration of the one or more micro displays used to create the image on the lens(s);

FIG. 35b is a diagrammatic illustration of a dongle in which can be housed a battery, micro circuits and a controller, such as a D-PAD;

FIG. 36b is a diagrammatic illustration of an ear-piece which can either be attached, as in an onboard sound-system, or unattached, such as magnetically or electronically connected to hearing-aids, or Bluetooth connected to a set of earbuds or earphones; and.

Figure 1:
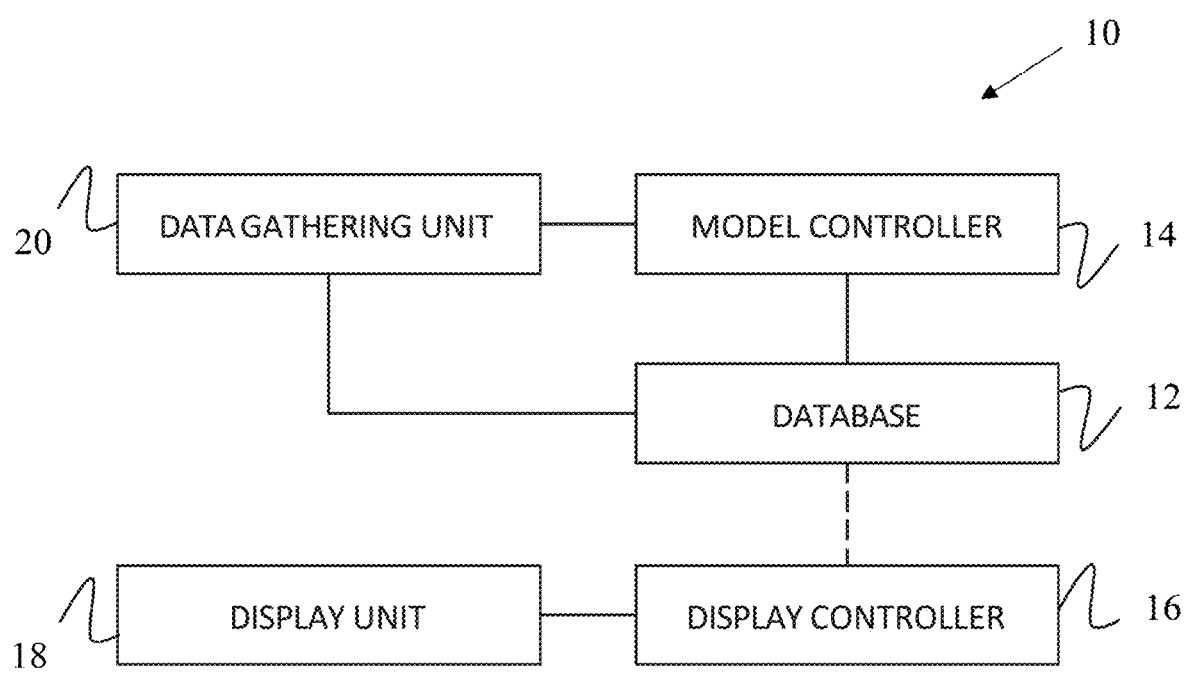
FIG. 1 is a block diagram of a system to augment a patient's vision, according to an embodiment of the present invention.

Other advantages and features will be apparent from the following description and from the claims.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification. It will be apparent to one having ordinary skill in the art that the specific detail need not be employed to practice the present invention. In other instances, well-known materials or methods have not been described in detail in order to avoid obscuring the present invention.

Reference throughout this specification to "one embodiment," "an embodiment," "one example," or "an example" means that a particular feature, structure, or characteristic described in connection with the embodiment or example is included in at least one embodiment of the present invention. Thus, appearances of the phrases "in one embodiment," "in an embodiment," "one example," or "an example" in various places throughout this specification are not necessarily all referring to the same embodiment or example. Furthermore, the particular features, structures, or characteristics may be combined in any suitable combinations and/or sub-combinations in one or more embodiments or examples. In addition, it is appreciated that the figures provided herewith are for explanation purposes to persons ordinarily skilled in the art, and that the drawings are not necessarily drawn to scale.

Embodiments in accordance with the present invention may be embodied as an apparatus, method, or computer program product. All of the systems and subsystems may exist or portions of the systems and subsystems may exist to form the invention. Accordingly, the present invention may take the form of an entirely hardware embodiment, an entirely software embodiment (including firmware, resident software, micro-code, etc.), or an embodiment combining software and hardware aspects that may all generally be referred to herein as a "unit," "module," or "system." Furthermore, the present invention may take the form of a computer program product embodied in any tangible media of expression having computer-usable program code embodied in the media.

Any combination of one or more computer-usable or computer-readable media (or medium) may be utilized, including but not limited to, for example, a random-access memory (RAM) device, a read-only memory (ROM) device, an erasable programmable read-only memory (EPROM or Flash memory) device, a portable compact disc read-only memory (CDROM), an optical storage device, a magnetic storage device, or what is commonly called the cloud. Computer program code for carrying out operations of the present invention may be written in any combination of one or more programming languages, including but not limited to, for example, Java, Mac, WebGL, OpenGL, C+, C#, Ruby, PHP, and so on. Further, the intelligence in the main circuitry may be software, firmware, or hardware, and may be microcontroller based or included in a state machine. The invention may be a combination of the above intelligence and memory and may exist in a central processing unit or a multiple of chips including a central graphics chip. The computer portion of the invention may include a model view controller.

The flowchart and block diagrams in the flow diagrams illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable media that can direct a computer or other programmable data processing apparatus to function in a particular manner, such that the instructions stored in the computer-readable media produce an article of manufacture, including instruction means which implement the function/act specified in the flowchart and/or block diagram block or blocks.

Several (or different) elements discussed herein and/or claimed are described as being "coupled," "in communication with," "integrated," or "configured to be in communication with" or a "system" or "subsystem" thereof. This terminology is intended to be non-limiting, and where appropriate, be interpreted to include, without limitation, wired and wireless communication using any one or a plurality of suitable protocols, as well as communication methods that are constantly maintained, are made on a periodic basis, and/or made or initiated on an as needed basis.

As used herein, when the word or term "picture," "image," or "video" is used it shall mean all or any one of the same.

The disclosure particularly describes a system, a method, and computer program instructions stored in media that augment the sight of an individual or user whose sight has been damaged or is otherwise defective. In general, the present invention provides techniques that may be implemented in systems, methods, and/or computer-executable instructions that (1) map the defective areas of the user's sight, (2) establish one or more boundaries that delineate between the effective and defective areas of the user's eye(s), (3) capture an image (or series of images) using a camera associated with the user, (4) map the captured image (or series of images) and generate a corrected image (or series of images), and (5) present the corrected image(s) to the user's eye(s).

With reference to FIG. 1, an exemplary system 10, according to one embodiment of the present invention, is illustrated. The system 10 may include a database 12 of information, which is originally programmed and which permits further programming and reuse and repurposing of existing and new data; a model view controller 14; a display controller 16; and a display unit or units 18, such as a dual display associated with a reflected display 18. The system may also incorporate one or more data acquisition units, such as a camera, sensor, controller, or D-Pad.

The system may load ansler grid data from memory and generate a shader based on the input ansler grid data. The system may then load the shader into a graphics processing unit (GPU). In the field of computer graphics, a shader is a computer program that is used to do shading: the production of appropriate levels of light, darkness, and color within an image, or, in the modern era, also to produce special effects or do video post-processing.

Shaders calculate rendering effects on graphics hardware with a high degree of flexibility. Most shaders are coded for GPU, though this is not a strict requirement. Shading languages are usually used to program the programmable GPU rendering pipeline, which has mostly superseded the fixed-function pipeline that allowed only common geometry transformation and pixel-shading functions; with shaders, customized effects can be used. The position, hue, saturation, brightness, and contrast of all pixels, vertices, or textures used to construct a final image can be altered on the fly, using algorithms defined in the shader, and can be modified by external variables or textures introduced by the program calling the shader.

Shaders are used widely in cinema postprocessing, computer-generated imagery, and video games to produce a seemingly infinite range of effects. Beyond just simple lighting models, more complex uses include altering the hue, saturation, brightness or contrast of an image, producing blur, light bloom, volumetric lighting, normal mapping for depth effects, bokeh, cel shading, posterization, bump mapping, distortion, chroma keying (so-called "bluescreen/greenscreen" effects), edge detection and motion detection, psychedelic effects, and a wide range of others.

Live low-latency video may be acquired via serial interface from a camera or imaging device. Alternatively, video may be acquired from multiple cameras for stereo vision, etc. The previously generated shader based on the user inputted ansler grid may provide the vector coordinates for remapping. Using the vector coordinates, the shader may manipulate the video pixels in the GPU. The pixels may be remapped to avoid vision defects as defined by the ansler grid. The output of the shader may be loaded into an output buffer to be displayed. Output buffers may include HDMI interface.

The GPU may be any desired CPU, including but not limited to a GPU, a FPGA, an ASIC, etc.

This system may include an algorithm that allows the mapping to be changed in real time to aid in the feedback loop, including a feedback loop that incorporates the HMD.

As will be discussed in more detail below, a data gathering unit 20 may be used to gather data that may be used to develop a visual model of the user's eyesight. The data may be used to establish the visual model, and the visual model and other data may be stored in the database 12. Since the peripheral receptors in the retina are usually still functioning in the macular degeneration case, the present invention may stretch, skew, and/or otherwise manipulate the image(s) presented to the eye(s) of the user to avoid the macula or the damaged portions of the macula. Thus, the entire image may be presented to, or onto, the functioning retinal receptors. As explained in more detail below, the present invention may create a distortion map of the image and display it, or project it onto the periphery of the eye(s), while avoiding the damaged portion of the macula. The distorted image may be presented to and/or projected onto the eye using goggles, glasses, smart contact lenses, or a photon projection using a virtual retina display of the image directly onto the periphery of the eye.

In general, the model view controller 14 may be coupled to the database 12 and may be configured to establish the visual model associated with a user and to store the visual model in the database. The visual model may include data related to a quality of the user's vision. The model view controller 14 may be further configured to establish a boundary as a function of data associated with the visual model. This process is discussed in further detail below. The boundary may be indicative of an area to be corrected within the user's vision. The model view controller may be further configured to establish a retinal map as a function of the boundary and to store the retinal map in the database.

The display controller 16 may be configured to receive and to store the retinal map. The display controller 16 may be further configured to receive an image (or series of images) from a camera, such as a video camera, associated with the user and to apply corrections to the image(s) based on the retinal map and responsively generate corrected image(s).

In one aspect of the present invention, viewing may be associated with predefined settings; for example, day time, night time, reading, watching television or cinema, or viewing images or video right on the HMD. The correct setting may be automatically selected for specific conditions and/or may be user selectable to fit changing conditions. For example, the settings may be associated with one or more macular or retinal maps, which may be generated.

The display unit 18 may be coupled to the display controller 16 and may be configured to receive the corrected image(s) and to present the corrected image(s) to the eye of the user. It should be noted that the present invention may be configured to present corrected video, as a series of images, to the eye of the user.

In general, the model view controller 14 and database 12 in one embodiment may exist in a computer module, circuit board, or ASIC, or in a laptop, computer, or notepad. In another embodiment, the model view controller 14 may exist on a circuit board within a headset, in a computer, specific or specifically designed hardware or apparatus, and application specific integrated circuit (ASIC) server, or servers operating independently, or in a networked environment. The data gathering unit 20 (described in further detail below) may be linked, at least temporarily, or may be data transferred over a network, electronically, or through a physical media; for example, through a wire or wireless system such as radio frequencies or infrared connection.

In one aspect of the present invention, the retinal map may be established automatically and adjusted, with or without the user's specific update permission, at or by the model view controller and then transferred electronically to the display controller.

In another aspect of the present invention, the model view controller 14 may establish a plurality of retinal maps that vary in either the parameters used to generate the retinal map and/or the method used to generate the retinal map. The plurality of retinal maps may be stored at the display controller 16. The user may then cycle through the retinal maps and select, for use, one of the retinal maps that works best. For instance, a particular retinal map may work best for the instant conditions. Thus, the user may select a retinal that works best for the conditions which currently exist.

As discussed more fully below, the display controller 16 and the display unit 18 may be embodied in a head mounted display, goggles, or glasses that are mounted to or worn by the user. Alternatively, the display controller may be mounted in a helmet or other headgear. Alternatively, the display controller 16 and display unit 18 may be embodied in a unit that is separated from, i.e., not worn by, the user, such as on a dongle connected to an HMD. One or more sensors may be utilized to find the location and distance of the user's eyes relative to the display unit 18 such that the image may be displayed properly and to track the user's eye movement relative to the display using eye-tracking.

Each eye of the user is different and typically has a unique defect. For instance, one eye of the user may have a specific defect, having a specific shape, size, and location, while the other eye of the user may not have a defect or may have a defect having a different shape and size. Thus, each eye of the user may be mapped separately and a respective visual model of each eye established. A border of the defect of each eye may be generated and an associated retinal map may likewise be generated. In one embodiment, separate cameras may generate a separate set of images for each eye and the display controller 16 may generate a respective series of images to be presented to each eye. Cameras may be of very high quality, and 4K or 8K cameras and projection may provide the best results.

Figure 2:
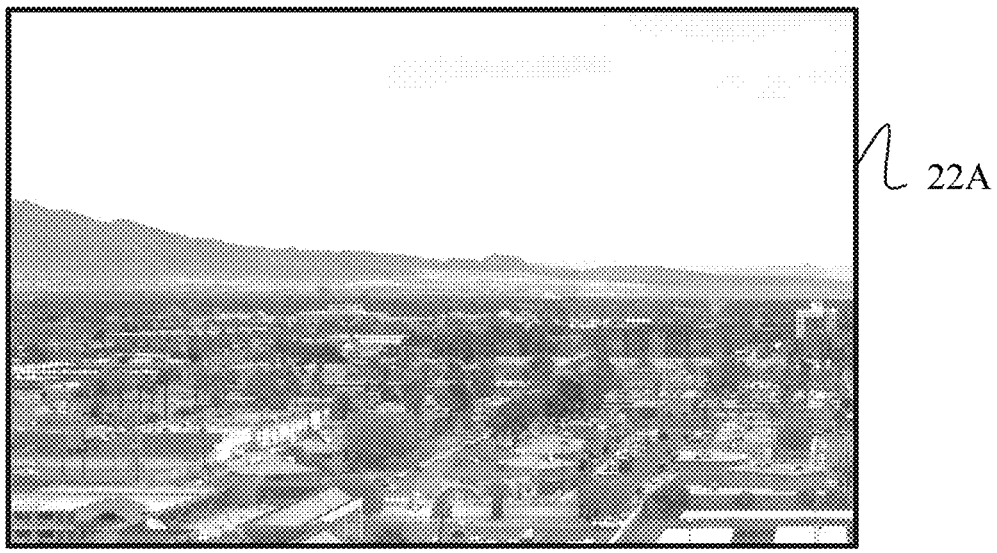
FIG. 2 is a diagrammatic illustration of a patient's vision without a defect.
Figure 3:
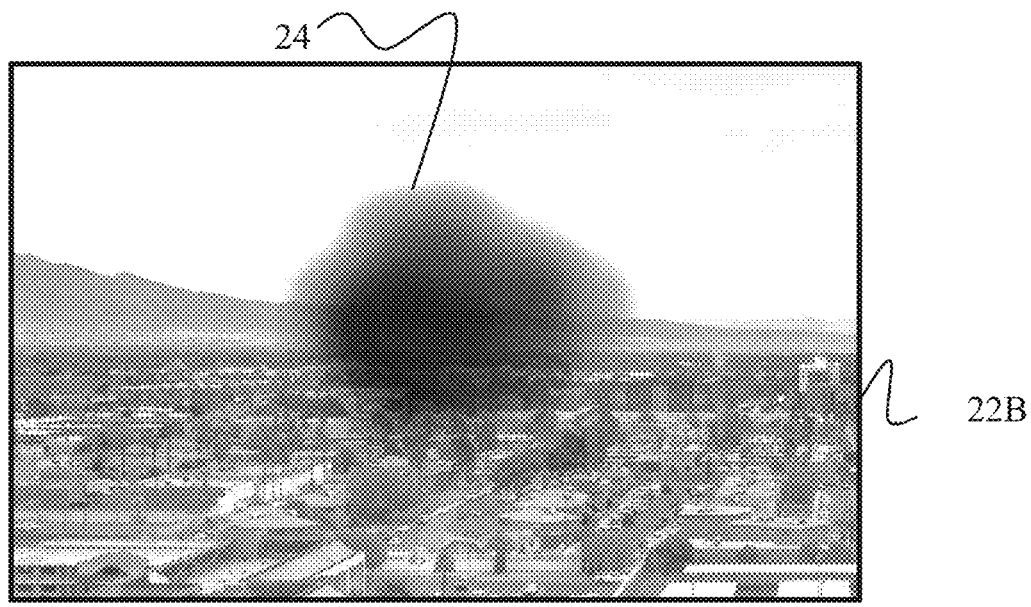
FIG. 3 is a diagrammatic illustration of a patient's vision with a defect.

With reference to FIG. 2, a graphic 22A representing the vision of a user's eye without a defect is shown for purposes of comparison. With reference to FIG. 3, a graphic 22B representing the vision of a user's eye with a defect is shown. The defect is represented by the dark shape 24 shown in the center of the graphic 22B.

In one aspect of the present invention, the visual model may be established using the data gathering unit 20. The data gathering unit 20 may include at least one of (1) a field of vision ophthalmological instrument, (2) a portable mobile field of vision test apparatus, and (3) a computer-based system. The process of gathering data using the data gathering unit 20 is discussed in more detail below.

Figure 4A:
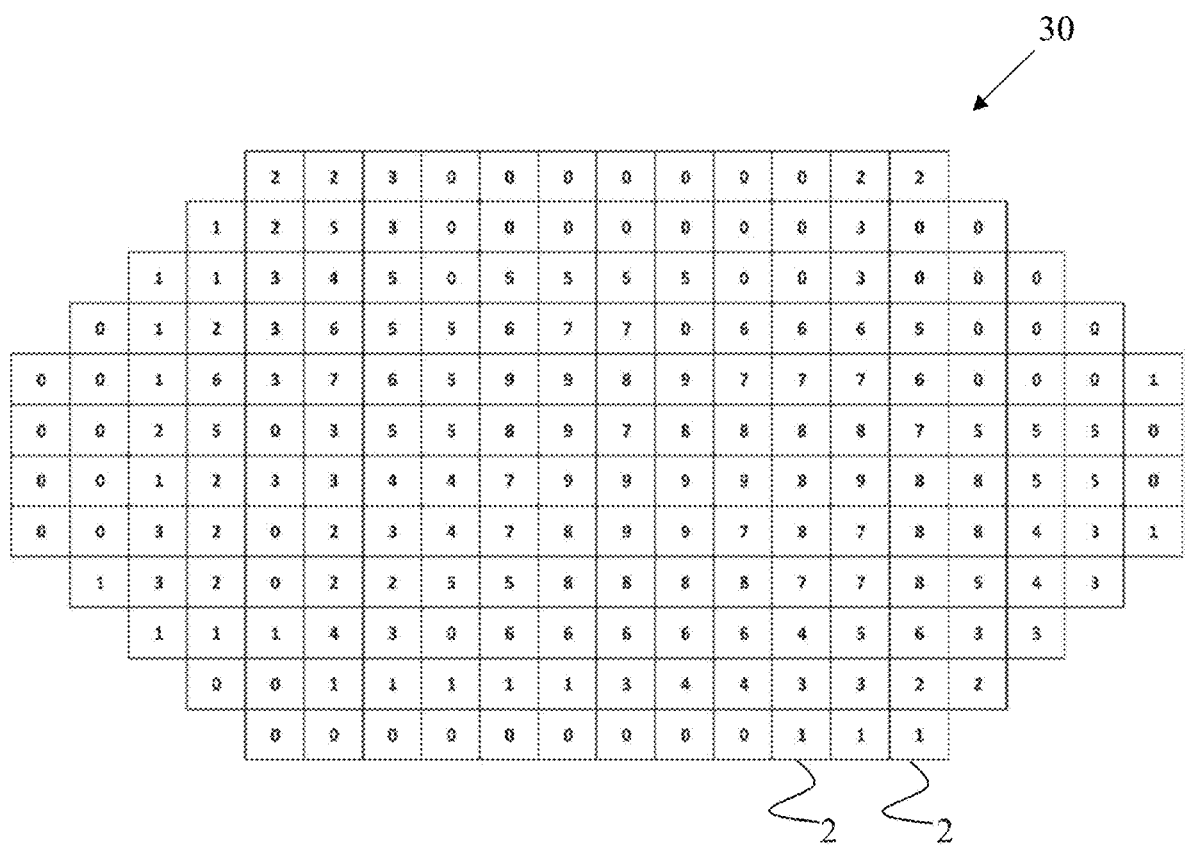
FIG. 4A is an illustration of a sample visual model, according to an embodiment of the present invention.

With reference to FIG. 4A, a simplified example of field of vision (FOV) data 26 is shown. The FOV data 26 may be used to create the visual model. The FOV data 26 may include a plurality of cells 28 arranged in a grid 30. Each cell 28 may have an associated value associated with the quality of the user's vision. The values may be based on an absolute or representative scale that is indicative of the quality of vision. Alternatively, the values may be a deviation from a standard value, or a value of an associated cell. For purposes of explanation, in the exemplary FOV data 26 of FIG. 4A, the values in the grid utilize a scale of 0 to 9, where 0 represents no defect, 9 represents a defect, and the values 1 to 8 represent a quality of vision between 0 and 9. It should be noted that a scale of 1 to 9 is for discussion purposes only. The scale utilized may be any suitable scale, for example, 0 to 99, 0 to 255, −30 to 30, or any suitable scale. Furthermore, the illustrated grid has 12 rows and 20 columns, but any size grid may be utilized. The shape of the grid may be used to approximate the shape of an eye and may be different between the left and the right eye. The size of the grid may be dependent upon the data gathering process, or data gathering unit 20 and/or the display unit 18. In another embodiment, the FOV data may be represented by a contour, polygon, or morphological operator.

The boundary may be established as a function of the values associated with the cells in the grid. In one embodiment, the values in the grid values may be compared with a threshold to establish the boundary. For example, in the above example, the threshold may be set to 7. Thus, any cell 28 having a value of 7 or greater is within the boundary and any cell 28 having a value of 0 is outside of the boundary.

Figure 4B:
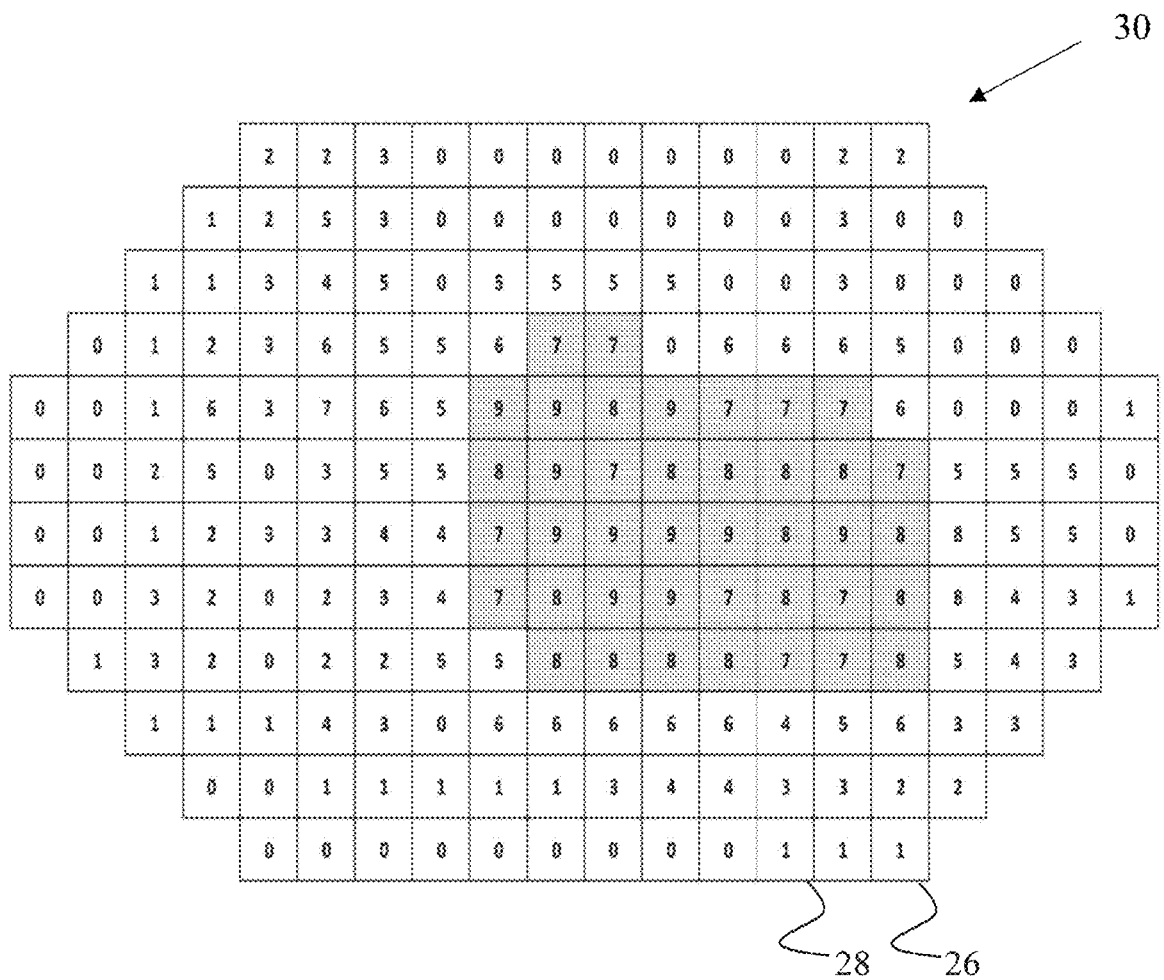
FIG. 4B is an alternative view of the sample visual model of FIG. 4A.

A modified view of the FOV data 26 is shown in FIG. 4B, in which the cells 28 meeting the above threshold are highlighted.

Alternatively, the FOV data 26 may be used to create a contour. The visual model may emerge from interpreting the raw data and is not necessarily a point-by-point transformation of the raw data. The intent is to put the removed pixels as close to where they ordinarily would have been; thus, the algorithms in the software may determine exactly where to move such pixels/rays based on (i) the whole of the defect, (ii) the distance of the specific pixel or ray from the border of the defect, (iii) whether a pixel is a new image or a part of an existing image, meaning whether the pixel is a part of an image or on the border of an image change, (iv) the other options for the pixel to move another way, and (v) where the adjacent pixels to be adjusted are being moved.

In another embodiment of the invention, vector images may be used. For the purpose of this patent, vector images and pixels are used interchangeably. However, in practice, unlike digital images which are made up of (usually) millions of tiny squares or other shapes known as pixels, vector images are made from mathematical points connected together by lines and curves to create different shapes. Since they are based on math and algorithms, not merely pre-placed pixels, vector shapes are extremely flexible and do not suffer from the same limitations as pixels.

The invention may be made up of five (5) major systems and a number of subsystems. One or more of the systems or subsystems may be combined, omitted, or integrated.

First Major System: Head-Mounted Display

The first major system is the head-mounted display (HMD), such as glasses, frame, and headgear (HMD), which may be worn on the head of a user and positioned over the eyes and nose like typical glasses or like the helmet of a jet pilot. In one embodiment, the HMD may be connected to another device that provides power, while in an alternative embodiment, the HMD may have its own power from the mains or from wireless power transmission or from a battery or other source. The HMD may house the cameras, microcontrollers, connectors, central processing unit, graphics processing unit, software, firmware, microphone, speakers, and subsystems, which may be comprised of sensors, such as motion sensors, six or nine degrees of freedom sensors (up/down; back/forward; left/right; pitch/roll/yaw), gesture recognition sensors, fiducial marker sensors, accelerometer sensor, infrared sensors, motion sensors, alert sensors to alert a user to a danger, gyroscope technology and related sensors, positional tracking sensors including but not limited to Wi-Fi location systems, mobile locations systems, and/or RFID location based systems, sound sensors, and/or optical sensor technologies. In another embodiment, the HMD may contain an RFID reader to read signals from RFID tags. In another embodiment, the HMD may contain optical character recognition/reader sensors to read information from the real world.

Alternatively, some parts of the system mentioned herein may be housed in a dongle attached to the HMD via wire or wireless connection. Alternatively, some portions of the system mentioned herein may be contained in a connected device, like a laptop, smart phone, or Wi-Fi router. Alternatively, some parts of the system mentioned herein may be contained in a remote location and accessed by the HMD via radio frequency (i.e. cellular bands) or other wireless frequencies or via wireline. Thus, in one embodiment of the invention, multiple HUD may be connected through a wire or wireless network in order to develop or control information which can be shared with other users. This may be accomplished by having the HMD gather information from the cameras or sensors processing the information through preset filters and distributing the information to all the other HMDs connected to the network. Alternatively, one or more of the HMDs could obtain information from a remote location, like information from a drone, and that HMD would have the ability to control the information or share the information with all the other HMDs connected to the network. In another embodiment of the invention, the information may be gathered from a remote location or library and shared with other HDCs through an intermediate source, like a smart phone or laptop.

In another aspect of the invention, the HMD may be connected to a device or a piece of equipment, like a forklift, and when activated may display to the user all pertinent information about the forklift, such as fuel level, battery charge, and/or time-to-service, or assist the forklift driver in accessing products in a warehouse. In this specific instance, the HMD may be fitted to use a technique like RFID location-based tracking to identify where the driver should drive the forklift to find the right parcel or product. In similar instance, the HMD may use GPS or cellular triangulation to order a map and route to a specific destination or an interim destination along the route.

In the RFID instance, the HMD may have an RFID reader incorporated into its system and the RFID reader may read RFID tags placed along a route or in a grid, which may define the exact way to get to a desired end. In the GPS/cellular triangulation instance, a GPU chip or cellular chip (sim) may be included in the HMD. This may include having the HMD be a controller that has the means to provide real-time travel as a director including means and method for interactive special mapping, including with simultaneous localization and mapping (SLAM) of a campus, warfield, outside area, house, building, warehouse, or other structure or structures or areas such that a user can access building co-ordinates via the HMD unit, which can provide real-time information about where the user, whether a human, robotic, or vehicle, is in a building or outside, and define the route of travel where a user needs to go to get to a predetermined location and carrying along other information to present at the destination or any interim point. Thus, a forklift driver wearing the HMD may be able to understand the path to get to a specific package or stop at a specific interim location.

The sensor array may also include mechanical linkages, magnetic sensors, optical sensors, acoustic sensors, and inertial sensors. This list is not exhaustive, but illustrative of the type of sensors located on the HMD. The HMD may also house virtual environment (VE) subsystems such as: (1) head and eye tracking for augmenting visual displays and syncing with eye movement; (2) hand and arm tracking for haptic interfaces to control virtual objects and aid in the diagnostic tools; (3) body tracking for locomotion and visual displays; and/or (4) environment mapping interfaces to build a digitized geometrical model for interaction with sensors, diagnostics, and simulations. Other sensor technologies that may be housed on the HMD include digital buttons, which may include power buttons and a D-pad or control pad for accessing and controlling functions by the user either within the HMD or contained within a dongle attached to the HMD. The sensors listed above may include their operating systems and output. The HMD or dongle may also house connectors, such as power connection for recharging a battery or for direct connection to an AC source, as well as other connectors for HDMI, sound, and other input/outputs, such as additional image overlay display, or for a diagnostics protocol for upgrading the system.

The HMD may also house the microprocessor control circuits (MCC) described below.

The HMD may also include a strap and counterweight or other headgear to balance the HMD and maintain its position on the head. In addition, the HMD may include a dongle whereby one or more of the systems or subsystems may be connected via wire or wireless to another device, such as could be worn on a belt or carried in a pocket to reduce the overall weight of the HMD. In an alternative embodiment of the invention, the HMD may exist in a ruggedized or HAZMET helmet, like those worn at construction sites or in a chemical plant or at environmental sites. In an alternative embodiment of the invention, the HMD may exist in a configuration like a welder's helmet, such that the lens and/or part of the headset connected to the lens may be lifted up and removed away from the face of the user by pivoting at a pivot point on the side, on the top, or near the temple of the wearer.

The HMD may contain a battery and receipt charging DC subsystem or, additionally or alternatively, an AC input and converter to connect directly to an AC source. The HMD may additionally or alternately contain a wired and/or wireless subsystems to connect or pair the device to other systems, such as sound, alert systems, fall monitoring systems, heart monitoring, other vital sign monitoring, and various APPs programs, cloud computing, and data storage. Other subsystems in the HMD may include a microphone/speaker and amplifier system, an integrated inertial measuring unit (IMU) containing a three axis accelerometer, a three axis gyroscope, a three axis magnetometer, an auxiliary port for custom sensors such as range finder, thermal camera, etc., GPS, SLAM sensor, gesturing sensor(s), infrared lights or cameras, brightness and color adjustment subsystem and control, network connectivity subsystem and controls, wire or wireless connectivity subsystem and controls, eye-tracking subsystem, gesture recognition subsystem, voice speech recognition subsystem, gyroscope, accelerometer, gagnetometer, obstacle avoidance subsystem, GPS, RFID subsystem and control, SLAM Sensors, other sensors, including infrared sensors and lighting and microphone(s), and various cameras and displays. In one embodiment of the invention, the hand gesturing subsystem may use RGB cameras or IR cameras with time-of-flight information to recognize 3D hand, finger, and arm gestures. This may also be accomplished by a combined gesture recognition subsystem like the Intel Realsense® chipset and may include coarse or fine tuning.

In another embodiment, the display may be a reflected display, like a heads-up display; in another embodiment the display may be a wave-guide display; in another embodiment, the display may be illuminated by a pico projector or other ultra-short throw projector; in another embodiment, the display may be a micro-mirror display; and in another embodiment the display may be projected via prisms.

The HMD may contain an auxiliary port for custom sensors, such as range finder, thermal camera, RFID reader, etc. In another embodiment of the invention, the power charging may be done by a transformerless power supply, such as a reverse switch-capacitor system in a module.

Other subsystems like Bluetooth and Bluetooth Light may be included for near connectivity to cell phones, smart phones, smart watches, tablets, automobiles, and the like for control and/or sending of information and content. The HMD may also include one or more global positioning systems or interior tracking systems, like RFID, Wi-Fi, or cellular tracking location based directional travel. Other communication systems may also be included based on either wire or wireless connectivity of the HMD. The HMD can also be connected, wired or wirelessly, to a main monitoring data system, which may track the health, whereabouts, and condition of the user to be displayed remotely to another person, such as a caretaker or a health care provider.

In another embodiment of the invention, the HMD may act like a router to which other wireless devices may be connected. This may be accomplished by either the HMD being connected to a wired internet system or a wireless internet system, such as a cellular connection or Wi-Fi. In this aspect of the invention, the HMD may operate independently of the other connected devices, but may also be controlled by the other connected devices, such as a smart phone. In this configuration, the smart phone may be paired with the HMD such that the smart phone may begin an application (app) like Pandora or Spotify, for example, and then the HMD plays the music, while the smart phone may be free to be used for other services like a call or searching the internet while the HMD remains active to the app.

In another embodiment of the invention, the HMD may receive its control instructions from another device, such as a laptop, tablet, or smart phone to which the HMD is paired in a network, either through a wire or wireless connection protocols. In this embodiment, the HMD might be activated by a smart phone which has opened the app for streaming content, such as Netflix or Hulu. In this application, for example, the smart phone would access the Netflix app, then send the streaming video to the HMD, which would receive the information either through a wire or wireless connection. In this fashion, the HMD may have access to all apps which a user has registered to their phone or laptop or other device, and the HMD may act as just another display chosen by the user, instead of the display on the smart phone, laptop, or tablet.

Alternatively, system may allow the user to register apps on the HMD and utilize them without any external device. In one embodiment of the invention, the apps icons show up visually and virtually by looking through the reflective lens, with the apps showing up in hologram or 3D or 2D as a part of the modification of the projected video, superimposed over the real-world images. A user could then select an app from the virtual visual representation shown in augmented reality format by a finger gesture, which may then be recognized by the hand and finger gesture tracking subsystem, making the virtual visually displayed app show up as selected, and then launched on the AR display. As such, a third party's app may be re-rendered on the HMD platform. Thus, for instance, a user could see app icons in virtual format overlaid onto the real-word and then select one or more, such as a picture app, from a number of apps showing up in virtual display. The gesturing subsystem may recognize that the user has selected the picture app, and instantly the processor would begin to load pictures on the AR display in virtual format. In this embodiment, the virtual visual AR overlay may re-display the app icons, and the gesturing subsystem may recognize which app is chosen for launch on the AR display. Thus, the augmented reality portion of the system may integrate a hologram or 3D or 2D image of the app, which is a re-display of the native app image, and superimpose the image over the real-world images caught by the cameras. Thus, in one embodiment, it would appear that the user is holding the apps on the palm of the user's hand available for selection with the user's finger of the other hand. To select the drawer of app icons, a user may employ voice command, eye-command, or hand gesture; may select from a virtual global menu, which may appear in virtual format superimposed over the real-world images; or may manually select from a non-virtual menu selection.

In another aspect of the invention, the speakers in the HMD may be earphones, which may make the information displayed to a user private and keep the headset quiet for use, such as on a plane, train, or car.

In another embodiment of the invention, the HMD may be paired with a certain vehicle or drone for control, including gesturing control. It should be noted that in the current state of the industry a drone is typically controlled with a large electromechanical device, which contains controllers to lift, guide, and land the drone, as well as to take pictures or video from the air. This invention teaches that the controls of a drone may be converted into virtual controls via a gesturing subsystem, wherein the controls are virtual controls which are only visible when the user is wearing the HMD. In this way, as one of many instances, a warfighter could use a drone to see over the next hill or obstacle without carrying extra drone control gear. The warfighter could activate the HMD, which may be embedded onto a typical warfighting helmet, and may use hand and finger gestures to control the drone. Additionally, the user or warfighter could use the eye-tracking in the HMD to also control some or all of the drone's functions. The extra value to a warfighter is that he or she could use the HMD in a heads-up display where the reflected display only partially obscures the user's vision and permits the warfighter to continue to be aware of threats in his or her surroundings by checking back and forth from virtual images to reality seen through the heads up display.

In another aspect of the invention, the HMD may be made such that it is capable of being locked on a user so that, in institutional environments, it cannot be easily removed. In this aspect, people such as inmates may be required to wear such HMD headgear so that if there is trouble or an emergency, a manager could either cut off the video feed, leaving the user with only limited sight resources with which to navigate, which could reduce the user's desire to become aggressive, or provide information for emergency exit. In this embodiment, the display screen may be subject to the command of an outside operator and could display, for instance, peaceful pictures and soothing music to calm the user experiencing a fit. Alternately, the display could become opaque and deny the user the ability to see, or the display could be used to heighten awareness with magnification, color enhancements, and sharper contrasts of images and sound.

The HMD may also be used to dispense smells to either enhance a pleasurable experience, or permit a focus on identification of a person or thing, or for training purposes, such as to give a user an artificial experience like would exist in a simulation or another not currently existent real-world situation.

As mentioned above, this invention may solve the typical "heads-up" reflected display problem of visualization in bright light or sunlight conditions. In this instance, the HMD may use a bright display, such as a Quad HD AMOLED display, which may be reflected onto the surface of a lens for the user to see the "virtual" portion of the display. In using a Quad HD AMOLED reflected display, the brightness may be adjusted up or down depending on ambient light. Alternatively, the adjustment may be in the system controller and may automatically adjust depending on what the sensors say the brightness of the ambient light is, which would typically be brighter when in brighter exterior light. The AMOLED, OLED, or similar display may be one display or two displays, one for each eye as reflected on the lens.

In one aspect of the invention, a reflective coating may be applied to the clear lens to enhance the reflectivity of the virtually displayed image. In another aspect of the invention, the reflective coating may not be necessary because of the operation of the dynamic opacity subsystem.

The clear lens upon which the bright display is reflected may be a plastic like Lexan or other clear polycarbonate or glass or any other clear material, and may or may not have a reflector integrated into the lens to improve visibility of the reflected display. In any case, the outside of the lens may also be bonded to a layer containing a liquid crystal display (LCD) or transparent OLED display, which may operate to obscure the outside light to provide greater acuity for the wearer viewing the virtual information displayed in high lighting conditions (dynamic opacity display or DOD). An OLED transparent display can be quite clear, which may make reading fine details or text on objects behind the display possible until something is displayed on the screen in "virtual mode," meaning something from the streaming video is shown on the display/lens. Alternatively, a transparent/translucent LCD may be used as an outer layer, or as a middle layer of the otherwise clear lens and bonded together with the clear lens upon which the reflected display is to be projected, to create the dynamic opacity.

Figure 31:
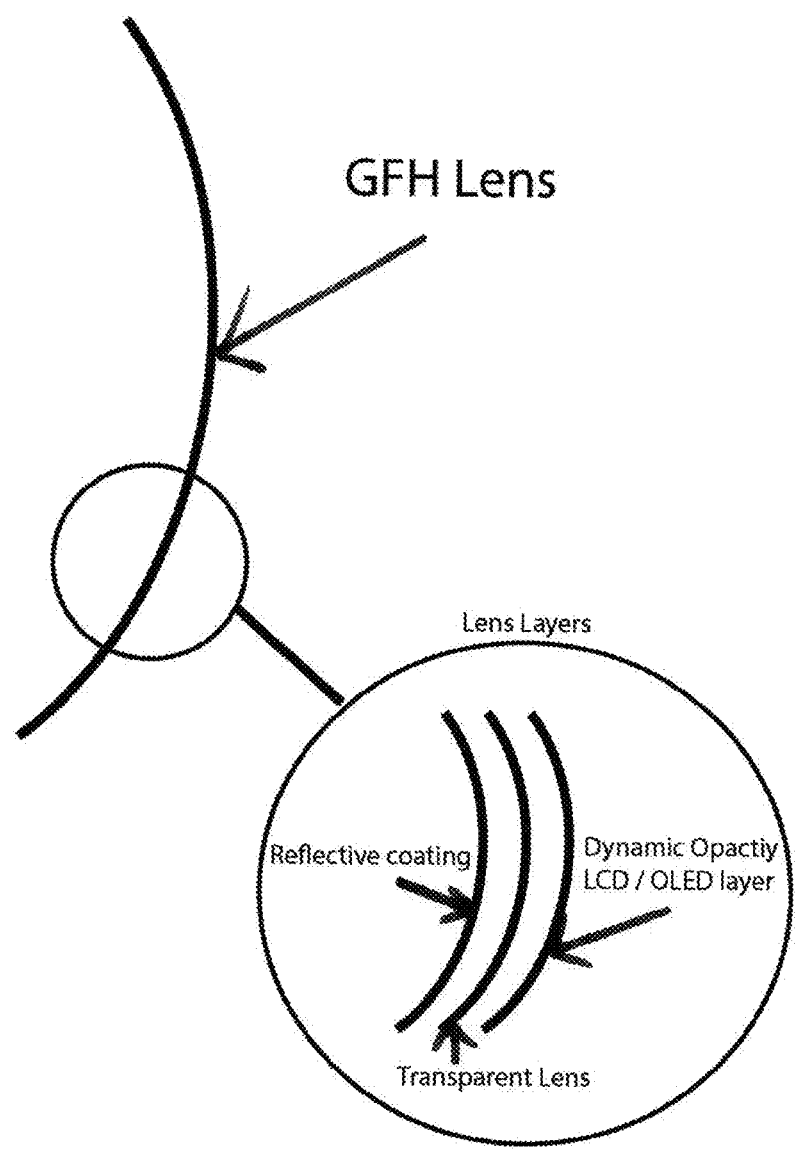
FIG. 31 is an illustration of lens layers.

Dynamic opacity may sense where the image is being projected on the interior of the lens and may obscure from one percent or less to up to 100 percent of the otherwise clear lens. In this aspect, the clear lens may or may not be also coated with a reflective layer. See FIG. 31. The clear lens may also have reflective material on the inside to increase reflectivity of the projected image, such that the base lens is not exactly clear, but is some percentage obscured by the reflective film, paint, or other embedded reflectivity. See FIG. 31.

The dynamic opacity subsystem may be controlled by the display controller and may work in tandem with the information displayed. The display controller may create an image buffer for the projected virtual display, and this information may be shared with the dynamic opacity controller, which may then activate the pixels that correspond with the exact or near exact location where the display controller is projecting the virtual image, so as to make the portion of the reflective lens upon which the image display is being projected opaque on the exterior of the reflective lens, so that the image displayed appears to be brighter due to the backlighting or light filtering provided by the dynamic opacity. The dynamic opacity subsystem may work because the transparent LCD or translucent OLED contain some resolution of pixels, which in the instance of dynamic opacity may be a lower resolution than the projected display, and each pixel is controllable by the dynamic opacity controller, which may get its information of which pixels to activate from the display controller. In the OLED, the activation of the pixels may be turning on the individual OLED RGB pixels in order to achieve the correct level of opacity to compensate for existing brightness for the condition experienced by the user. In this instance, the RGB pixels may be activated to create a shadow effect or, depending on the type of light which is extant, an emphasis on either red, green, or blue, or combinations of the three. In addition, the dynamic opacity subsystem may be pre-programmed to provide a user with various options from warm color to cold (amber to green) for a sunglass effect on the exterior of the reflective lens. In the case of the LCD, the activation of the pixels may be one or more phases and changing the polarization of the pixels to achieve opacity on the exterior of the glasses for the same effect. In this instance, typically, an LCD unit that does not include an RGB component may be employed, as just outside ray blocking is needed.

Alternatively, with dynamic opacity, any other transparent material which provides control of pixels or areas inside the transparency to create an opaqueness may be used. In either case, the outer layer may be transparent to the user, providing a see-through lens to the real world, until virtual information is displayed on the HMD reflective lens, such as a hologram, a 2D image like a movie, or other 3D image or information, including text.

The model view controller (MVC) may control the dynamic opacity display, such as through corresponding data input information about where the reflective display is projecting information. In this instance, the MVC may identify in the buffer or elsewhere, in digital format, where the images are going to be displayed on the reflective display, and the MCV may anticipate these locations and turn on pixels, including RGB pixels in the transparent LCD or OLED, and cloud or rather make more opaque the portions of the lens corresponding to the areas of the lens where the virtual image is displayed. In this fashion, the dynamic opacity may provide a backdrop or background display corresponding to the pixels where the virtual image is displayed making the contrast of the virtual display greater to the eye, so that brightness like natural sunlight can be minimized, which would otherwise compete with the reflected display and cause it to be hard to see. With the dynamic opacity, the reflected display may have a buffer between it and exterior light, which may give the reflected display greater brightness to the eye.

The dynamic opacity could be in either a course or fine mode, meaning that the opacity from the transparent OLED or LCD may either appear in the general area of the virtual display or, for fine applications, may appear in almost or the exact same pixels which correspond to the image pixels being displayed or reflected on the interior of the lens. In another aspect of the invention, the dynamic opacity may work with wave guide displays or prism type displays with equal effect. Likewise, the dynamic opacity described herein may be used with a micro-mirror type display with equal effect.

There are many methods to identify exactly where the coarse or fine opaqueness should appear, but one embodiment may use the same eye-tracking as the primary display/lens. The MVC may thus know exactly where the eye gaze is and how far each way on a six-way axis the virtual display is centered and extends, so that the opaqueness mimics the same space as the virtual display, according to where the eyes are gazing as identified by the eye-tracking software. In this way, the reflected image display may overcome the issue of not being bright enough in daylight and other high light conditions. Likewise, the dynamic opacity may include a transparent OLED or LCD overlay or layer of the lens that can also act as sunglasses for the display and tint the entire display to compensate for bright lights, like on a sunny day. Alternately, a light valve may be used with the same effect in a similar manner. A light valve (LV) is a known device for varying the quantity of light from a source, which reaches a target. Examples of targets are computer screen surfaces or a wall screen or, in this case, the coarse or fine coverage of the virtual display on the glasses lens.

In the dynamic opacity technology, the MCV may be pre-programmed or programmed to automatically compensate for external brightness and/or may act as instant transition lenses. In this case, the entire exterior layer of transparent OLED or LCD may tint to balance the bright external light and still provide additional opaqueness on the portion of the lens where the virtual video or picture or image is being displayed. Alternately, the light valve can be used to completely black out the reflected image lens so that the augmented reality aspect becomes a virtual reality aspect, blocking all real-world information and only displaying information from the micro-displays onto the reflective lens.

In another aspect of the invention, the HMD may be more like a helmet or a face shield than distinguishable lenses.

In another aspect of the invention, the display may be a small display, like an OLED-on-silicon micro-display. Such a display device may consist of two key elements: the silicon backplane that contains circuitry to drive the OLED pixels, and the OLED emissive frontplane layer. With a small micro-display that is only 1 inch by 1 inch but contains 2.5K by 2.5K resolution, with as bright a display as possible (1,000 NITS), one can use two displays, one for each eye, to be the projector on to a reflective or semi-reflective lens. In this case, the micro-displays can serve as the projector for a reflected display which the eyes of the wearer would see. In this instance, the correction or fine tuning may be offered by the ultra-short-throw corrective lenses contained within or on the HMD and the correction for projection of the reflected display from a micro-display mounted on the HMD. These displays can be used to project an ultra-short-throw image onto reflective lenses, which can be clear plastic, such as a polycarbonate resin thermoplastic (Lexan), combined with layers of the dynamic opacity subsystem described herein. In this fashion, the display subsystem may consist of a controller with camera input, which may be buffered and then projected by the micro-displays with the corrective lens or lenses, which can be together, or sandwiching around a polarized layer which is used to direct the light in a specific fashion. The ultra-short-throw image may then be projected onto the reflective lens made of polycarbonate resin or glass or other see-through moldable material, with the dynamic opacity layer included on the reflective lens. The reflective lens may permit the user to see through to the real world, while also enabling the user to see the projected image. By varying the level of the opaqueness of the dynamic opacity, the projected image may be made more visible, especially in high external lighting conditions. Alternately, the dynamic opacity can be increased to where the lens has zero or almost zero transparency so that the projected image is the only thing seen. In this instance, with the reflective lens, the headset goes from an AR device to a VR device. Also, the opacity can make the lens have virtually zero transparency, whether or not there is any image projected on the lens from the micro-projectors.

In another aspect of the invention, the display may be one or more small micro displays like those which have a silicon substrate over which an OLED layer is affixed. OLED micro-displays may be fabricated on silicon backplanes by a vendor like TSMC, with a stack of OLED and other materials affixed above. In one embodiment, the affixed OLED micro-displays may use a white emissive layer that is topped with an array of RGB color filters, much like with LCDs. Sometimes a RGBW structure is used where the white is essentially a clear filter. This white sub-pixel element allows for a brighter display, even up to 1,000 or more NITS. These OLEDs are light emissive so that light (or color) is created only at the targeted or activated pixels, which provides the best contrast with very fast response times (less than 10 mS). The optics design may be similar to the LCD case.

In another embodiment, the OLED may be one where each red, green, and blue sub-pixel emits its own light directly so no color filter or mixer is needed. Typically, an OLED with a white emitter with a color filter is an easier structure to adhere to the silicone and thus an easier manufacturing process than one that creates individual red, green, and blue sub-pixel emitters. In another embodiment, the micro-display is an OLED-on-silicon, which uses a white emitting OLED material with RGB stripe color filters. However, the direct RGB type offers higher efficiency and may be preferred for wearable applications.

Typically, the input to the displays may be with a single MIPI or MIPI converted to LDVS interface. The micro-displays may need a sandwich or pancake of corrective lenses interlaced with a polarization lattice layer to correct for angle of ray to the most direct point to enter the eye.

In addition, the two micro-displays may be "married" to the reflective display for correlation and to cause the largest number of light rays to enter the eye at the most optimum angle. See, FIG. 32. However, the IPD controlled by the software may need the displays to accommodate the narrowest to the widest common human IPD. Typical specs for the micro-displays may include the following:

| Symbol | Parameter | Min | Typ | Max | Unit |
|---|---|---|---|---|---|
| $V_{LINE0P1}$ | LINE_IN-referenced Supply Voltage | 4.9 | 5 | 5.2 | V |
| $V_{DDA}$ | 1.8 V Analog Supply Voltage | 1.62 | 1.80 | 1.98 | V |
| $V_{SSA}$ | Negative Analog Supply Voltage | ? | 0 | ? | V |
| $T_{FA}$ | Functional Ambient Temperature Range | −40 | | 85 | ° C. |
| $T_J$ | Junction Temperature Range | −40 | 27 | 125 | ° C. |

| Item | Parameter | Current | Target |
|---|---|---|---|
| Format | 2048 × RGB × 2048 | | |
| Color Dot Pitch | 2.88 × 8.64. μm | | |
| Image Diagonal | .99 in | | |
| Frame Rate | 60-120 Hz | −40 | |
| Color Gamut (% sRGB) | DCI-P3 Desired | 72% | 125% |
| Contrast Ratio | | 3,000 | 10,000 |
| Brightness (nits) | | 1.50 | 1,000 to 2,000 |
| Brightness Uniformity | | | ◆ 85% |
| Speed (Response Time [ns]) | Lowest Possible Requested Overall Oculenz RT budget is <10 mS. | | <10 |
| Video Input | MIPI Requested. Expected (25-pair mini-LVDS) * ASIC Change requested moving forward | | |
| OLED Power Consumption | Not to exceed 500 mW per display | | |
| Power | 1.2 V to 5 V | | |
| Input Formats | Requested MIPI. Expected = LVDS 24-bit RGB, 24-bit YCbCr 4:4:4, or 16-bit YCbCr 4:2:2 | | |

| Symbol | Parameter | Conditions | Min[1] | Typ[2] | Max[1] | Comments |
|---|---|---|---|---|---|---|
| $V_{LINE0P1}$ | Supply Voltage | At LINE_0P1 | 1.2 | | 5 | . |

-continued

| Symbol | Parameter | Conditions | Min[1] | Typ[2] | Max[1] | Comments |
|---|---|---|---|---|---|---|
| $I_{LINE0P1}$ | Supply Current | At LINE_0P1; en = 1 | | | 500 mW | |
| $t_{RAMP}$ | Supply Ramp Time | At LINE_0P1 | 0.1 | | 100 | |
| $t_S$ | Startup time | ramp at en = 0 | | | 100 mS | |

In another embodiment, the silicon fab may offer embedded memory on the silicon backplane, and, taking advantage of memory such as DRAM or EEPROM or other writeable and readable memory, the drivers, such as LVDS or other drivers or display converters to a MIPI protocol, may be embedded into the memory of the silicon chip that serves as the backplane for the OLED or AMOLED to provide faster display speeds and better communication integration. Further, on-silicon memory in the display's silicon backplane may allow the writing and changing of custom drivers that can be read from any system. Utilization of this on-silicon memory may make it possible to also store optical input and output information about the display in order for the main subsystem to understand any type of optical distortion that needs to be corrected for and provide for that correction in the main video buffering processes.

In another aspect of the invention, the display may be one or more small micro displays like the those offered by Kopin, which is a 1 inch by 1 inch, 2.5K by 2.5K resolution OLED or AMOLED display(s) affixed to the silicon. These micro-displays may be used to project an image onto a clear lens connected to the head mounted display that contains computer intelligence through a CPU and can be known as a smart head mounted display or HMD. In another aspect of the invention, there may also be either or both a layer of reflective film on the lens or the outer layer of the lens that contains the dynamic opacity technology as explained above. In this instance, a corrective lens or lenses may be affixed to very small micro-displays, which may be bright enough to provide a reflected image onto the reflective lens. In this instance, in order to correct and fine tune the image for displaying on an ultrashort throw between the display and the inside of the reflective lens, the micro-displays may utilize one or more image correcting lenses and may be combined with a middle layer of a wave guide or polarization, which may provide enhanced image resolution and may guide the image's rays to exactly where it is to be displayed on the reflective lens.

Figure 32:
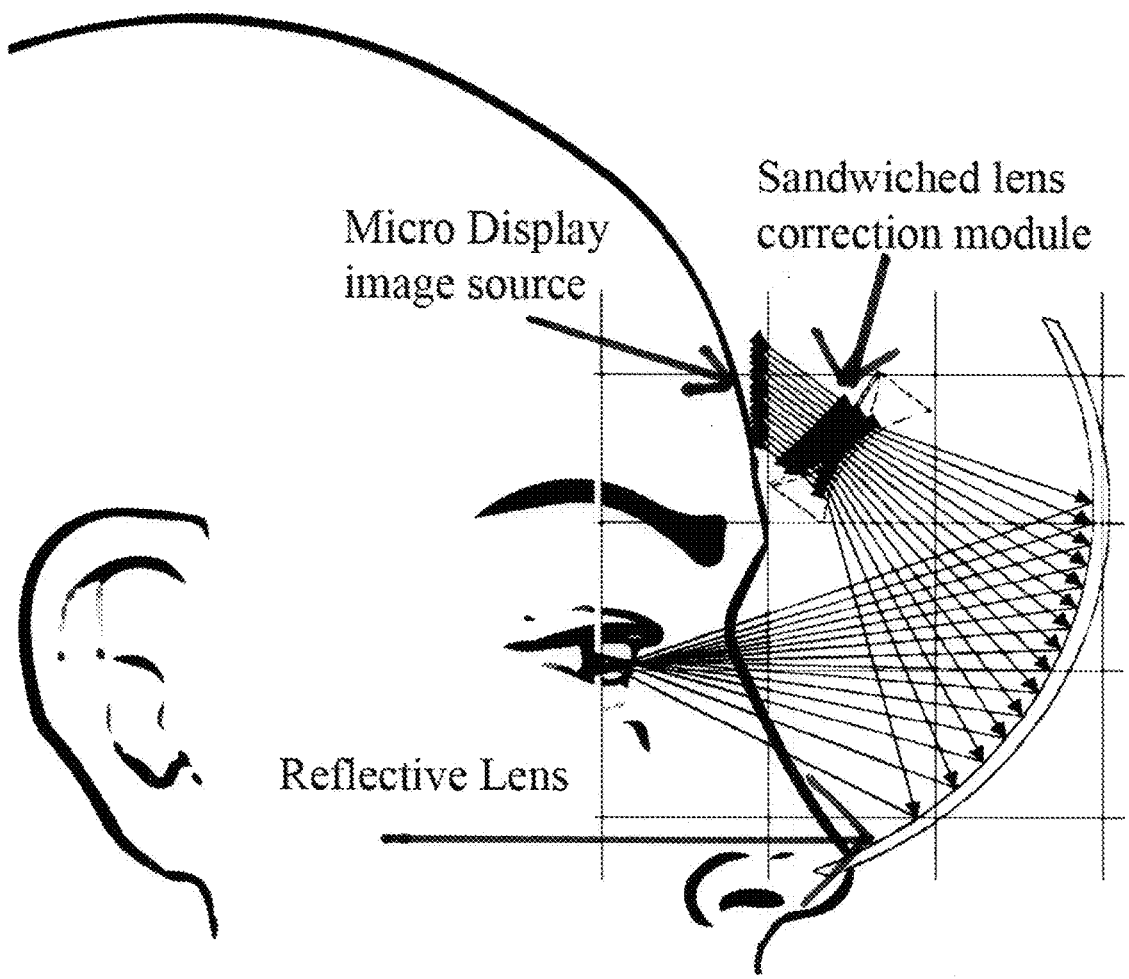
FIG. 32 is an illustration of a micro display configuration.
Figure 33:
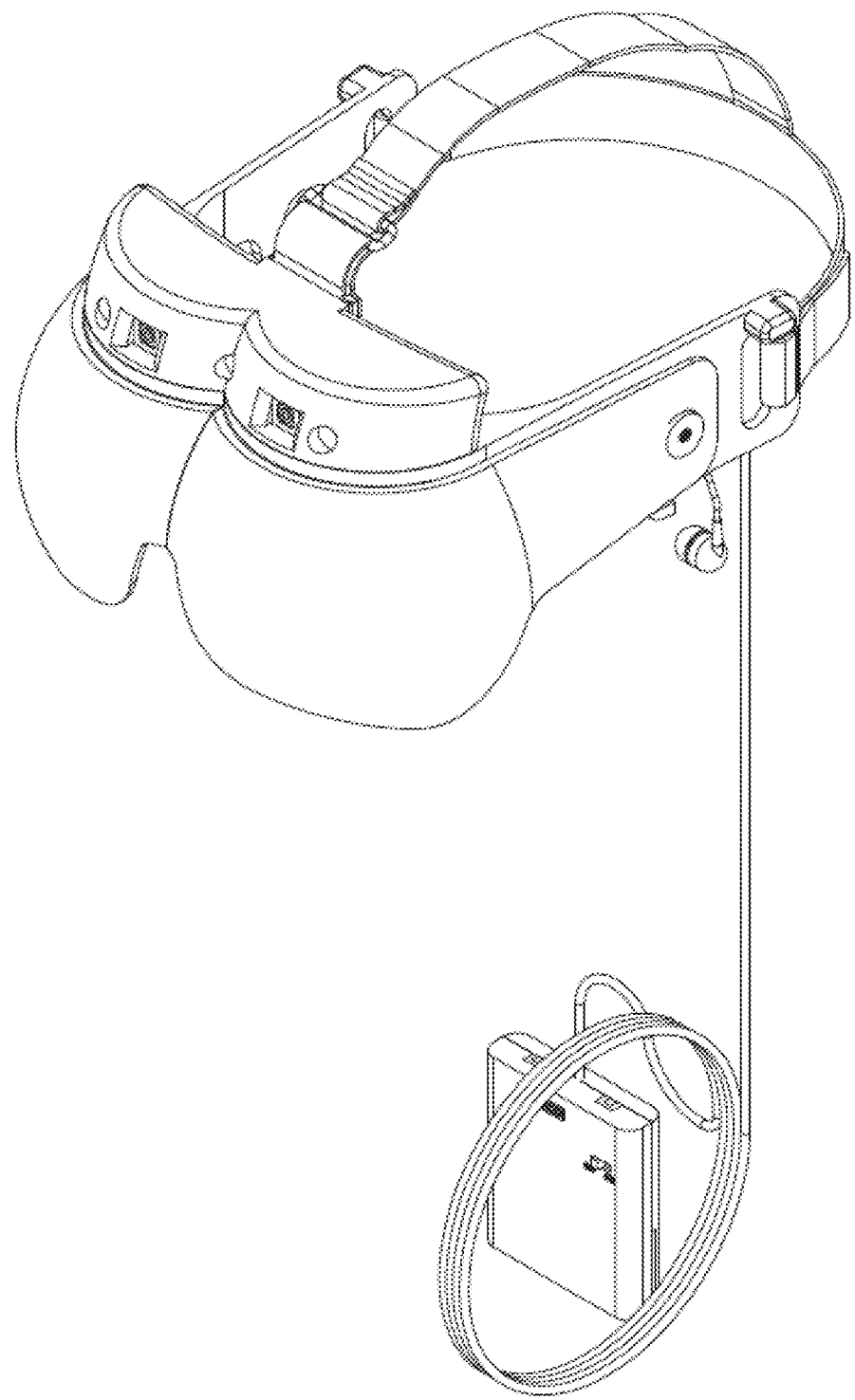
FIG. 33 is perspective view of the head mounted display (HMD) with a battery/circuit dongle, according to an embodiment of the present invention.
Figures 34, 34A, 34B, 34C, 34D:
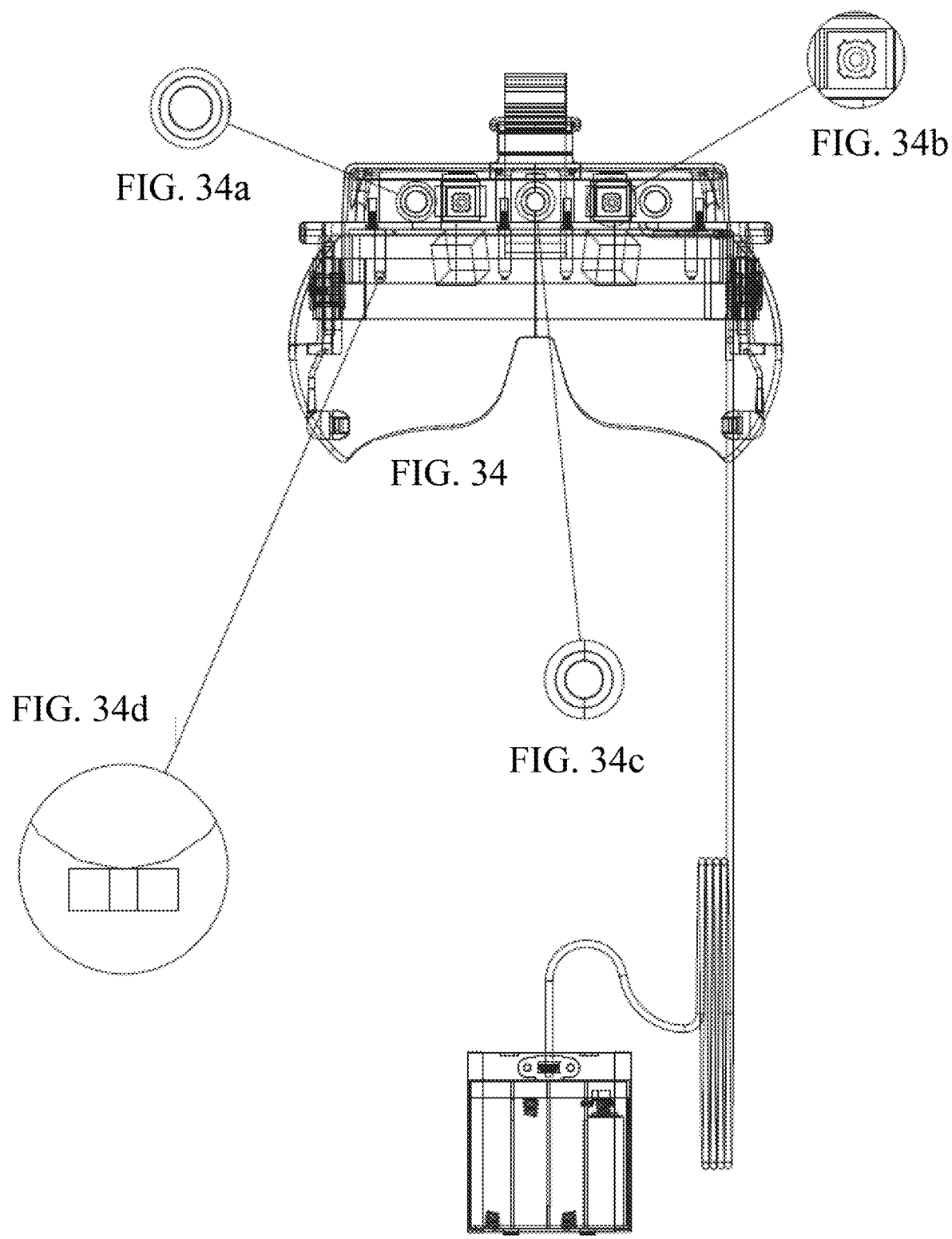
FIG. 34 is a diagrammatic illustration of the front of the HMD.
FIG. 34a is a diagrammatic illustration of a high-resolution camera.
FIG. 34b is a diagrammatic illustration of a second high-resolution camera.
FIG. 34c is a diagrammatic illustration of a 6 to 9 degrees of freedom sensor.
FIG. 34d is a diagrammatic illustration of a placement of an IR light for the eye-tracking subsystem.
Figure 36A:
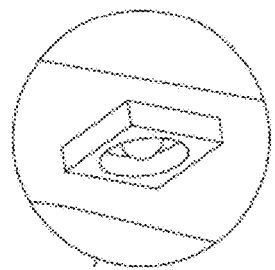
FIG. 36a is a diagrammatic illustration of an eye-tracking camera which can be mounted on the lens(s) or on another structure such as a nose bridge or a laterally extended nose bridge.
Figure 36B:
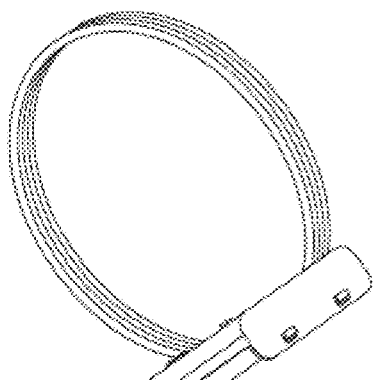
Figure 36:
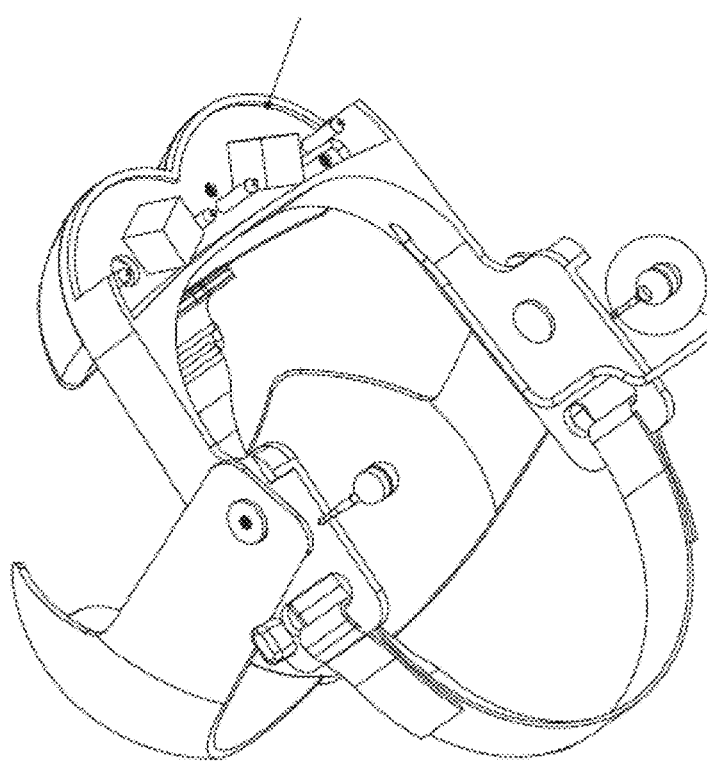
FIG. 36 is a diagrammatic illustration of the undercarriage of the HMD.
Figure 37:
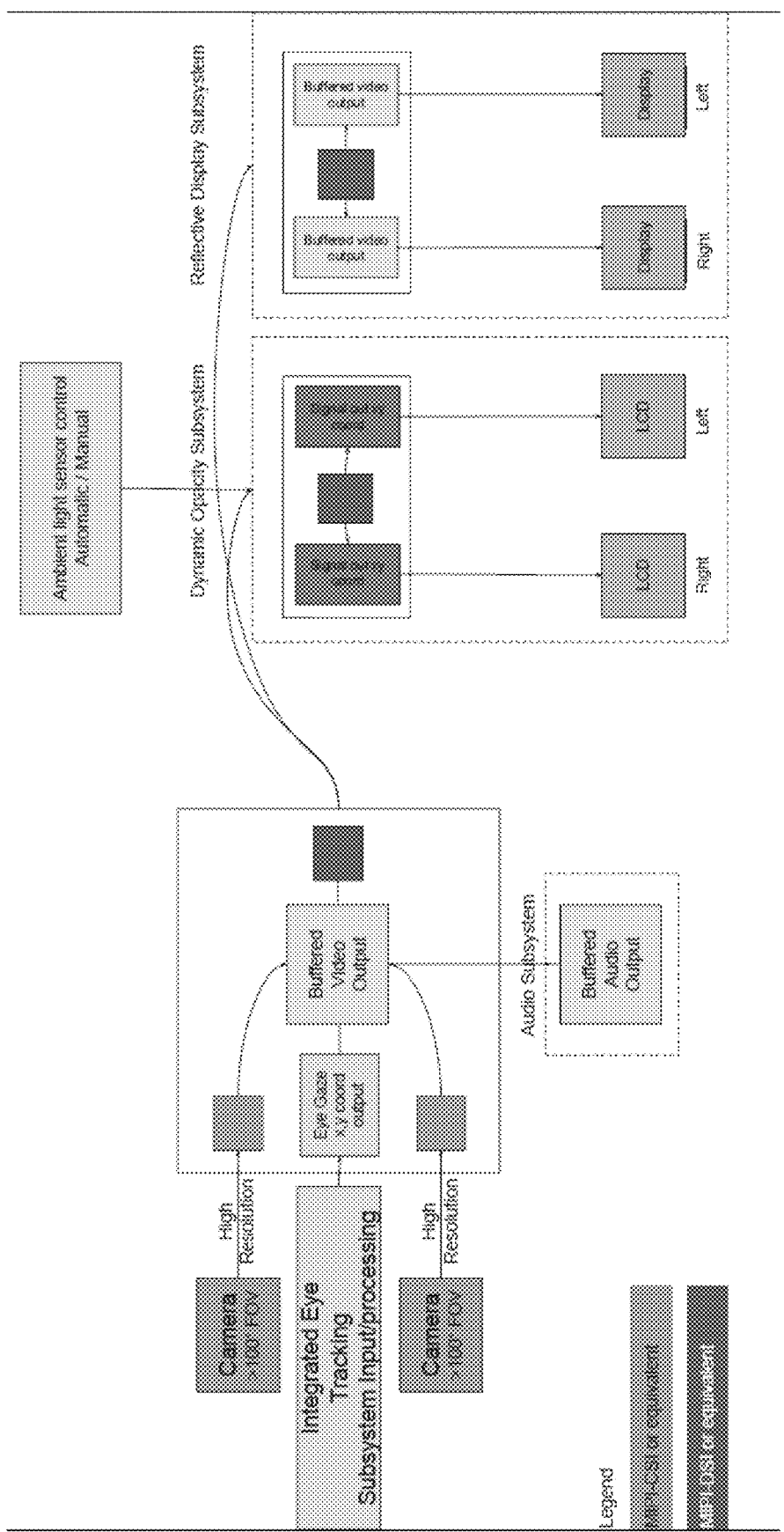
FIG. 37 is a schematic illustrating the camera and display subsystems.

In one embodiment of the invention, two corrective lenses may sandwich a wave guide or polarization layer. The image projection source may be a small display, as shown in FIG. 32, that is rotated to achieve the greatest clarity and field of view. The image may then pass through a circular polarizer. The circular polarized image may then pass through a lens with a positive diopter to focus the light through a linear polarizer. This linearly polarized light may then pass through a negative diopter lens, and possibly multiple negative diopter lenses, to achieve the necessary projection size required. The purpose of the polarizing films, used either in combination with other correcting lenses or not, may be to retard light from being emitted through light that is reflected onto the display and to focus the light rays on the specific part of the reflective lens as is desired. After passing through the lens curvatures, which may provide the correct size of projection, the image may then be reflected into the eye using a spherical lens, possibly coated with a semi-reflective or reflective surface. In this aspect of the invention, the angle of the display and lens combination to the angle of the spherical reflection surface may be adjustable to provide focus for eye location, which can be monitored using eye-tracking technologies combined with the control of the projected image. Further, an adjustment can be permitted on the corrective lens, which may be correlated to the micro-display, and thereby one can change the closeness of the lens to the micro-display, which would permit the user to adjust the reflected lens display closer or further from the user's face, to better allow room for the user's own corrective glasses or large facial features, like a large nose or other gear worn on the face, like an oxygen mask or filter mask (i.e. like for a fighter pilot or in a HAZMAT situation).

The eye-tracking subsystem may work through hardware and software. The software may be connected to the system's GPU working in connection with the system's model view controller. The eye-tracking may be captured by infrared (IR) light being projected onto the eye, which may create a glint or reflection, which may then be captured by an IR sensitive camera. Typically, an eye-tracking system may capture the glint from the eye from 30 frames per second to 500 frames per second. This information may be stored in real time in the model view controller (MVC) and then processed into a virtual space represented by XY or Cartesian coordinates. These coordinates may provide the system with the information about where the user's gaze is in relation to the reflective lens.

When used for medical applications like AMD, the eye-tracking information may be correlated with the buffered information about the person's eye visual defect such that when the manipulated image is displayed, it is in sync with the user's gaze. This may be necessary because the eye scanning and eye movement necessitates that the buffered and manipulated area of the video be moved to correspond to the user's eye gaze so that the buffered hole and the user's defect align and remain in sync. All this processing may happen in real-time and keep up with the movement of the user's eye. Latency may be important and keeping the latency to less than 10 milliseconds may aid in preventing the user from feeling dizzy and preventing whirr.

In another embodiment of the invention, the medical application of the system may include real-time blood pressure and heart rate monitoring.

In addition, the eye-tracking methods used to register eye movement to find the direction and targets of a person's gaze may also be used to reveal abnormalities in eye functioning, noticing fatigue, intoxication, drug abuse, or drug reaction. Further, the eye-tracking technology included in the system may be able to screen for such medical issues as concussion, Parkinson's disease, and/or eye defects, such as lazy-eye. When used in combination with learning disabilities, the system may help researchers learn more about an individual's dyslexia or other reading problems.

In another embodiment of the invention, a computerized worm gear or drive may be used, or non-computerized mechanical device such as a worm gear or gear may be used to move the micro-displays on the HMD such that the displays can be aligned with a person's own inter pupillary distance or IPD. In the case of a computerized worm gear, this gear may get its information about how far to move in one to four directions from the eye-tracking subsystem, which may measure the distance from the gleam detected in each of the person's eyes and transmit measurement data into movement data so that the worm drive aligns the micro-display in the HMD to the perfect position for the person's own IPD and relative height vis-à-vis the way the HMD is worn, so that alignment side to side and up and down is accomplished. Alignment of the user's eyes on a four axis may be necessary because this ensures the sharpest reflected image for each individual user in combination with how the user wears the HMD. In one embodiment, the IPD may be fixed based on the average of human variance. In another embodiment, the IPD may be variable and may allow the user to set the separation according to their eyes, via either mechanical or software means. In the mechanical, a small motor, such as a micro worm drive or a worm drive with a piezo motor, may allow for the range of adjustment. Alternatively, the IPD may be adjusted through software by shifting the image projected on the display. Typically, more than enough image data may be collected so that the image can be shifted left or right to accommodate a variance of IPD.

In another aspect of the invention, the HMD may be capable of being locked on a user so that in institutional environments it cannot be easily removed. In this aspect, people such as inmates may be required to wear such HMD headgear, so that if there is trouble or an emergency, a manager could either cut off the video feed leaving the user with only limited sight resources with which to navigate, which may reduce the desire to become aggressive, or may provide information for emergency exit. In this embodiment, the display screen may be subject to the command of an outside operator, and could display, for instance, peaceful pictures and soothing music to calm the user experiencing a fit. Alternately, the display may become opaque and deny the user the ability to see, or the display may be used to heighten awareness with magnification, color enhancements, and sharper contrasts of images and sound. The HMD may also be used to dispense smells to either enhance a pleasurable experience or permit a focus on identification of a person or thing, or for training purposes, like to give a user an artificial experience like would exist in a simulation or another not currently existent real-world situation.

In another aspect of the invention, the HMD may be more like a helmet or the display more like a face shield than lenses.

In another aspect of the invention, the HMD may be more like a band and the reflective display may be like two partial spherical clear lenses, one partial sphere over each eye.

In another aspect of the invention, the real world may not be displayed, but rather may be blocked out by the dynamic opacity and only videos, television shows, emails, or other online or prepackaged information may be displayed, either with or without the macular degeneration type pixel manipulation, so that a user could experience other forms of entertainment, training, learning, or task accomplishment with the mixed reality glasses than just a real-world projection onto the display. The HMD may also be fitted with night-vision, infrared, or other types of cameras so that the experience is hyper real world. Thus, any kind of camera may be used to make a display. In this embodiment of the invention, the HMD may be programmed to act as a host for other devices utilizing technologies like Apple Airplay, which may permit the HMD to be "paired" with other devices, like a phone or smart watch. In this instance, one may refer to the HMD as a smart head mounted display or HMD and all the applications (apps) on a person's cell phone or tablet may be transferred to the HMD seamlessly. So, in this instance, a user could begin a Hulu or Netflix movie on a cell phone or tablet, and then it could be directed or transferred to the HMD for continued viewing, which would free up the cell phone for other use.

In another aspect of the invention, the apps may appear virtually as being projected by the micro-displays in a fashion to simulate a hologram. In this instance, the gesturing sensors may pick up on the xy coordinates which app a finger is pointing to and when a specific gesture is executed, like "air clicking" on a specific app, such as Netflix or Blackpills app, the controller system may recognize the selection and open that app up in a way so that it is projected as a hologram or other image on the lens. Alternately, the app may be opened up by a voice command, or other shortcut, that, when executed, portrays the app as a visual image on the reflective screen as a hologram or other image so that the user can see what the app has to offer.

In these aspects of the invention, the HMD may be connected to the internet via cellular or WI-FI or other radio frequencies or wireline or wireless frequencies and may act like a router with other devices, which can attach themselves to the HMD, much like computers acquire and connect to a typical internet router. This may allow the HMD with the a Wi-Fi or cellular enabled circuit board to have the ability to access the internet or transmit either Bluetooth or Bluetooth Low Energy to and from other devices.

In another aspect of the invention, the HMD may have speakers or earphones attached with volume control to permit sound to enter to the user from the HMD.

In another aspect of the invention, the HMD may be loaded with artificial intelligence, like the Google virtual assistant, Siri, or Alexis. In this instance, the HMD may be programmed with a virtual assistant virtual image and may be able to show a visual virtual assistant (VVA), not just a voice like Siri or Alexis. Technology may be included like that invented by a group from the University of Washington, where researchers have created a new tool that takes audio files, converts them into realistic mouth movements, and then grafts those movements onto existing video. In this instance, the AI software neural nets may be trained to change a video of a speaking mouth to other words or may be used to create a VVA with a minimum of actual videos taken of the live subject which is to be the VVA.

In another aspect of the invention, voice recognition technology may be combined with voice and video recognition, such that when the artificial intelligence (AI) voice responds, like Siri on Apple or Alexis on Google/Android applications, there may also be a corresponding image of a person or thing on the HMD lenses. Thus, in one instance, instead of just a voice response as with Siri and Alexis, an image of a girl would appear with the AI response and the words would be synced with action from the "virtual person." The virtual person, called here as "Simone," would be numerous sets of pre-recorded responses that go with the questions. These AI questions and responses may be generally known, and in this instance, like other AI instances, the AI could access the internet or other stored data information in order to formulate a response. For instance, a user of the HMD could ask Simone, "What is the weather in Laguna Beach" and Simone's AI could access the GPS or cellular triangulation to understand that the user is in Laguna Beach, Calif., as opposed to Florida, and the Simone image could appear as a virtual person on the HMD lenses and respond visually and audibly to the user, "Here is the weather in Laguna Beach today" and either describe the weather or provide web-based data on current weather conditions. The basic aspect of this invention is that typical voice AI routines may now have a visual element that is displayed on the HMD. In another aspect of this invention, the virtual person could be named, for instance, Simon, and so on, and the user could select the visual image from a menu list. The menu list could contain both live people who have pre-recorded certain parts of speech and actions and animated or 3D versions of characters, such as superheroes, Pokémon characters, or other cartoon type characters that serve as the visual image. In another aspect of the invention, a visual representation of a loved one, such as a mother, father, or spouse of the user, could be selected from the menu by first uploading a picture or video of the person, and then mouth technology could be used to make it appear that the person was saying the voiced words.

This could be combined with AI learning where the user, in setup, would speak his or her name, and the AI virtual person would have a template from which to pronounce the name of the user correctly so that each HMD could be personalized to call the user by his or her own name.

In another aspect of the invention, the HMD may be adapted for use on dogs or other animals to aid in training, having the trainer pre-record video instructions, to be projected on the HMD lens, much like the virtual person above, which could command the animal to conduct a task, and if the animal correctly executes, as recorded by the HMD, a treat would be dispensed from the HMD or other device controlled by the HMD.

The system may also provide a visual virtual assistant that interfaces with the outside world of the internet and the stored system memory. The visual virtual assistant may be a virtual person, male, female, gender neutral, or cartoon, who may provide answers and responses to instructions from the user. Thus, instead of just hearing a voice like the Google assistant, Cortana, Siri, or Alexis, there may be a person of the user's choice, which pops into view and responds to your voice requests. With the visual virtual assistant, the user may speak questions or wishes and a chosen visual virtual assistant may appear to grant the user's wish and lets the user see them fulfilled in virtual reality, such as displaying a music video or the cover CD of a track the user requested to be played. The user may summon the visual virtual assistant at any time while wearing the headset. The visual virtual assistant may talk to the user in a conversational manner, ready to help the user with many things and perform a variety of simple tasks, like playing music. However, the visual virtual assistant may also be used to control smart-home gadgets, giving it the ability to control home or office thermostats and other devices.

For medical and industrial solutions, the system may utilize technology that deploys bone sound conduction technology. This technology may bypass the middle and inner ear, where most hearing loss mechanisms occur, and permit a user with hearing loss to hear better. The system may decode sound waves and convert them into vibrations that can be received directly by the cochlea so the eardrum is never involved. The sound reaches the ears as vibrations through the bones (or skull) near the back of the ear. For other solutions, the system may include speakers, earbuds, or headphones, or may connect with the user's own earphones through Bluetooth or Bluetooth Low Energy (BLE).

Under these embodiments, the HMD may include either speakers which would be controllable or have incorporated into its sound system earbud type speakers, which are either attached via wire or via a wireless network in the HMD, like Bluetooth light.

In another aspect of the invention, the cameras may be used to not only display an image in real time to the user, but also to record the image that a camera captures for replay later. Thus, a user, if sleepy, could activate a record button, causing the CPU and GPU to record the real-world images, for instance from a football game, and the user, when awakened, could then enable the recorded display to show on the lenses of the HMD. This feature could also be used to recall real world experiences, for instance to record a university lecture for playback and contemplation at another time. The playback may be in real time, slow motion, freeze framed, stopped, and fast forwarded or reversed. In this aspect of the invention, the HMD may have a subsystem that permits storing data and replaying data and menus to identify the stored information, or to recall an instruction previously given. In this instance, the user could activate the record function when taking medication and the CPU would log such information and be able to respond to visual, text input, or auditory requests, like, "did I take my medicine today?" to which the HMD would respond yes or no or not known, depending on whether the recorded information was available. In another aspect of the invention, the record function may be configured to automatically record certain functions, like image recognition software, which could activate the recording of taking medicine, convert that to database information, and be able to play back the correct information to the user. The HMD could also become Bluetooth enabled when in the proximity of other devices, like a pulse oximeter or blood pressure cuff, and automatically record this information and store it in the database to be replayed, recorded for later use, or sent to a third party, which might be a caretaker or health care provider, or stored for recall by the user.

In another aspect of the invention, other meaningful information may be displayed along with either the real-world information or non-real-world information, such as TV or a movie, where a user can allow the information to be altered or amended by text information or sound to conduct a certain time-based task, like, for instance, an alert to take medicine, check on a pet, or answer a phone call or email. In this instance, the HMD may permit the user to use a D-pad, fiducial marker, or other controller to switch from a real world or non-real-world experience on the display to a task-based experience, such as an email or phone call or video phone call.

In some embodiments, the user may use voice command to call up a virtual dial pad, and then use finger gesturing to punch the numbers and make a cell call. Alternately, the user may use the visual virtual assistant to place a call from a list of previously recorded callers. The user may virtually text by calling up a text menu and creating a text message and then telling the visual virtual assistant which known number to send it to. The system may be able to do virtually any task that a cell phone can do. The system may work by creating a custom Wi-Fi, cellular, or Bluetooth network in the user's home, allowing the system to seamlessly get handoffs, so the user can sync, stream, or share information to or from a computer, tablet, or cell phone to the headset. For instance, the user can start a Netflix movie on a cell phone, then transfer the movie to watch on the headset, or start a call on a cell phone and then transfer it to the headset.

These examples are but a few of the many tasks that may need the user to switch the input of the display, and all examples used herein are by way of illustration and not limitation. In this specific case, the main idea is that the HMD may be akin to a wearable computer, and may permit a change in the user's environment and display to correspond with the task or undertaking necessary at the time, whether to see the real world, to see the non-real world, or use the HMD as a wearable computer, online device, Wi-Fi device, RFID device, near field communication device, or other communication device, learning device, or a smart device, like one that would clock elapsed time.

In another aspect of the invention, the HMD, acting as a wearable computing device, may be capable of processing a credit card payment or undertaking some other task that the physical limitations of the user would otherwise prohibit or that the use of the HMD would enhance.

In another aspect of the invention, the HMD may not provide specific correction for eye diseases like macular degeneration, which requires repositioning pixels or vectored images, but may contain all the subsystems which exist to inform the user and show a user how to reach a certain waypoint or prioritize travel, all displayed on the lens display of the HMD. In another aspect of the invention, the pixel manipulation may be used, but not to correct for eye defects like macular degeneration, but to reposition a display onto a certain portion of the lenses, so that a user can see both the display and the real time world at the same time.

Thus, the HMD may contain other wearables technology to monitor, report, and track or direct the user. This may be done by audio, or within the display or as a separate display, where, for instance, the real-world environment is displayed, and a text is also shown of directions or alerts or any kind of useful information to the user. Alerts may also be signaled by vibrations from the HMD. The HMD may also signal messages to people external to the HMD, and, for instance, to alert third parties that an impaired sighted person is passing, or alert third parties that the person has some sort of authority, like a siren, or flashing light, in the case of police officers or emergency personnel.

The HMD may also contain an image projection and lenses (IPL) system, which is the combination of the projector and lenses upon which the image or corrected image is to be displayed, along with their connectors and integration with the other systems and subsystems.

The HMD may also contain connectors for a user diagnostics programming, and computer interface, for wearable computing functions and other subsystems explained herein. The examples above are designated herein as subsystems of the invention, which also is understood to include all powering, connectivity, computing, display, and integration of the subsystems. The computing and user diagnostic programming may be resident in the system or external through a connector. Thus, for instance, the user diagnostics programming can be in the circuitry and intelligence of the system or the HMD or accessed externally through wire or wireless connections to a device like a tablet, laptop, computer, or mainframe. The HMD may all be worn on the head, or be like a helmet, or be dispersed on other parts of the body as auxiliary wearables.

Second Major System: Camera Input System

The second major system is the camera input system (CIS), which may include one or more cameras and their lenses, connectors, and operating systems. As mentioned above, the cameras may be typical video or still cameras or may be of a specialized nature, like night vision, infrared, 360° cameras, thermal imaging, magnification, color, black and white, or 3D cameras with each their own distinctive displays. One or more of each of these different types of cameras may be incorporated into the CIS.

In a typical medical correction configuration, the HMD may contain one or more camera and camera systems for capturing the real word visuals that the user would ordinarily see. The HMD may also contain one or more cameras that monitor eye movement so that corrective software can receive this eye positioning information and approximate the epipolar geometry of the eyes (eyes moving inwards or outwards, left or right, transversely) and calculate for the same, as well as the offset of the line of sight of the cameras versus the actual eye position so that the display shows nearly what the user's eye would ordinarily see.

In another embodiment of the invention, the CIS may be partially or completely embedded on smart contact lenses, where the cameras, in the instance of macular degeneration, may be positioned on the smart contact lens (SCL) in the exact location where no sight exists, being typically in the most central 15% of the eye. The SCL may contain is own battery, sensors, communication, and charging apparatus, including communication devices such as backscatter, interscatter, Bluetooth, Wi-Fi, ZigBee, RFID, and other antenna transmissions. In these instances, the HMD may provide the energy to be harvested by the SCL and the communication network and protocols, for wireless communication, all of which may be a subsystem of the HMD. Thus, if SCL were worn by themselves, they may need another device to harvest energy and communication reference from; here the HMD system may provide the necessary energy and communication link and may be synced together.

In another embodiment of the invention, one or more cameras per eye may be used to create monocular or binocular vision. In this instance, the HMD system may also have a method to monitor the movement of at least one eye, like a camera in the HMD facing back towards one or more eyes to monitor the eye movement, for line of sight augmentations to the projected image, and for epipolar geometry corrections for the movement of the eyes focusing on far away versus close items. This camera may utilize eye tracking software to provide to the IMP the information necessary for an adjustment in the display so that the image displayed as nearly as possible represented the real-world images; thus, there may be correction for epipolar geometry and line of sight, at least in the software.

In another embodiment of the invention, one camera may be used, creating monocular vision to be displayed to one or both eyes. In this instance, the monocular vision may be corrected per eye, so that the cut-outs are different for each eye, such that the correction best suits each eye differently.

In another embodiment there may be one or two or more cameras per eye receiving real world input. In the instance of using two cameras per eye, it is recommended that the cameras may be offset towards each other, so that each camera's FOV intersects the other. This is because, when capturing a wide field of vision, the cameras themselves may interject a certain amount of distortion. A typical camera lens, which may not introduce a great degree of distortion, may have only up to about 75 degrees FOV. Thus, to capture more than 75 degrees FOV, which may be necessary under this patent's teaching, two cameras may be recommended to avoid wide-angle lenses, which introduce distortion, and to avoid the most distortion from camera lenses that attempt wide FOV. By using the joint image from two cameras, however, and then stitching the image together as one in software, less distortion may be introduced into the actual image to be manipulated and a higher degree of pixel accuracy may be maintained from the camera input to the image manipulation program(s) (IMP).

Third Major System: Microcontroller Control Circuits

The third major system is the microcontroller control circuits. This group of chips, parts, circuits, and circuit boards may include one or more microprocessors, its circuit board and parts, and typically a specialized application specific integrated circuit (ASIC) which may be a separate chip or housed in one of the other chips in the microprocessor circuit board. The MCC may perform the main functions of the invention and may receive the input from the CIS and sensors, run the routines and programs for collecting sensor data and visual images, correct for the macular defect of the user, and control the display. Portions of the MCC system may be controllable by the user, especially related to the macular degeneration diagnostic program (MDDP) subsystem. This MDDP subsystem may contain the software and firmware for the user application defect mapping program which establishes the boundaries, one or more, per eye, of the defect area, as well as the boundaries of the area of projection. The MCC may also house the video manipulation programs (VMP), which may collect the camera input and reposition the image and pixels for corrected vision display. The MCC may also house the application program interfaces, as well as the graphic user interfaces (GUI) and routines. The MCC may also house the controllers for all of the sensors, inputs, outputs and user control.

As stated above, the VMP may be any number of kinds as described previously, or could be a pixel manipulation scheme or vector math like taking the image from the real world such as the pixel interpolation and simulation, image stretching, or other software video distorting application.

In one embodiment, a flat picture may be sent to the buffer by the camera and may be turned in to a fisheye or barrel distortion where the middle is larger and then the image may be squeezed at the edge. In this instance, the central image, which may be as near as possible to the deficit of the person's disease, may be removed and the image may be stretched and displayed. In the instance of the goggles, the edge may not be critical, and may simply be cropped to permit the central portion of the video to be displayed without the edges, which may have been pushed out by cutting the central portion out. In another embodiment of the invention, the edges may be important, like in the case of the mixed reality macular degeneration glasses where phase two distorted images must be remerged into phase three video images.

Thus, this invention teaches that one camera may be used for monoscopic image capture and display. In addition, this invention teaches that two cameras may be used to simulate true stereoscopic vision on the goggle/glasses display, wherein the IMD model may include factor correction for epipolar curves, guided by the epipolar geometry, so that stereo vision, generated by two or more cameras, can be employed and be displayed, and seen, as one PRI image.

The invention may use computer aided video images, which may be skewed and stretched in a matrix distortion or other similar fashion to put the most or the entirety of the image onto the peripheral vision of the patent by opening up the center of the image and manipulating it to the peripheral cones of the eyes, as seen by the patient in the projected image, in order to project the video captured images on the peripheries of the cones in the eyes where vision is still active. One of the benefits of this invention is that no invasive procedures are necessary and, as the user's macular degeneration changes, the software can be adjusted so that the image is now correctly skewed. It is an additional advantage of this invention that live feedback may be used to determine the areas where the image is to be and is not to be projected.

In the fashion taught by this invention, the viewed experience may make it nearly impossible for the user to distinguish between what is actually seen and the image that is created by the PRI.

Thus, the spreading and/or multi-lateral skewing of the image may reflect the corrected image onto 3D or high definition goggles and/or glasses worn by the user. The image may be skewed via the IMD module to avoid projection to the area of the eye that involves the macula, but still has all the image information. To imagine this process, think of a picture which is printed onto a stretchable and compactable substance. A hole is cut into the middle of the image and stretched open. The image compress into the sides of the picture. Thus, all of the information of the picture is still there, it is just rearranged where a hole is in the middle and the image is moved each way to the side, top, and bottom. This hole-cutting may be done via algorithms and computer software/firmware technology, for instance, using a technology like matrix distortion, as above mentioned.

Matrix distortion of a camera and matrix calibration, which is the correction of the distortion, are commonly known areas of camera calibration and have been used for a long time. Often times, cameras display significant distortion. However, the distortion is constant like on a matrix, and with a calibration and some remapping the distortion can be corrected. Typical distortion correction takes into account the radial and tangential factors. For the radial factor one uses the following formula:

$$x_{corrected} = x(1+k_1 r^2 + k_2 r^4 + k_3 r^6)$$

$$y_{corrected} = y(1+k_1 r^2 + k_2 r^4 + k_3 r^6)$$

So for an old pixel point at (x,y) coordinates in the input image, its position on the corrected output image will be (x_{corrected} y_{corrected}). This corrects for the presence of the radial distortion which manifests in form of the barrel or fish-eye effect.

Tangential distortion may occur because the image-taking lenses are not perfectly parallel to the imaging plane. It can be corrected via the formulas:

$$x_{corrected} = x + [2p_1 xy + p_2(r^2 + 2x^2)]$$

$$y_{corrected} = y + [2p_1(r^2 + 2y^2) + 2p_2 xy]$$

However, for this invention, a type of reverse methodology that would not normally be thought of may be employed. Thus, once typical distortions in the camera have been fixed, it is the teaching of this invention that an intentional distortion may be introduced. In one embodiment, the IMD model may stretch a center pixel to the points at which an individual cannot see, and compress everything else to fit in the remaining peripheral portion of the goggles. In this fashion a hole may be artificially cut into the image by computer and software/firmware aided manipulation such that a pixel which was formerly in the center of an image is squeezed to the outside so that the entire image in projected around the hole in the center, which may be artificially created. Only the matrix distortion portion of the model is shown here, as the other pieces are not directly related to the IMD model. There are other substantive parts of this program for projecting the image once the IMD model is applied. As shown, the IMD distortion model is shown as a value to the "webGL"1, a program which can be used with "renderingContext"2.

Fourth Major System: Image Projection and Lenses System

The fourth major system is the image projection and lenses system. The IPL projector and lenses may employ such technologies for display, such as wave guides, mirrors, prisms, or other technologies, such as transparent rear projection film, to correctly display the image on the glasses (lenses) or on a portion of the lenses. Alternatively, a heads-up type display may be used, such as a transparent shield or facemask. In practice, the lenses may be one of any of a number of types of see-through displays, like augmented reality or mixed reality glasses, or can be immersive and not transparent like virtual reality goggles. Some examples of organic light emitting diodes (OLED) that can be employed are passive-matrix OLED, active-matrix OLED, transparent OLED, top-emitting OLED, foldable OLED, lucius prism OLED, white OLED, quantum dot light emitting diode (QLED), ultra LED (ULED) and Ultra HD 3840×2160 pixel resolution, also called 4K, which is twice the resolution of full HD and has four times the number of pixels. A recommended combination is transparent active matrix OLED (AMOLED) with the evolution of technology as it is now because AMOLEDs are thin, have fast refresh rates, are less complex from an electronics standpoint, offer a lot of control over individual pixels, and consume low amounts of energy, especially since they produce their own light; and they have high resolution and produce sharp colors, which is needed for the invention to work at its optimum. In another configuration, lenses, such as Corning's transparent display technology featuring Corning® Gorilla® Glass, could be used. The application of a special functional film on the thin, durable Gorilla Glass surface may create a transparent display that is acceptable for displaying real time augmented video onto the HMD lenses. In addition, the application of technologies such as LG Display's N Pixel technology can assist the invention by making the pixels clearer from any viewing by the eyes. Further, technologies such as retinal projection may be used, and may be housed in the HMD.

Fifth Major System: Diagnostics Impairment Mapping System

The fifth major system is the diagnostics impairment mapping (DIM) system and tools, which may include virtual simulations and tools, including a user manipulated method of viewing a grid and using hand gesture sensors or tools like fiducial markers or a connected mouse to identify the area and boundaries where no vision exists, so that this mapping can be obtained from the real analog world and transferred into digital coordinates for correction by the video manipulation program. In this instance, the user may select a diagnostics setting, and an Amsler grid may appear on the lenses one at a time. While one lens is being evaluated, the other lens may be opaque so as to not let the user be distracted. The user may trace the edges of the border of the sight, which may then be transposed by the MCC to specific mathematical coordinates which create a border where the image is to be removed and replaced elsewhere. The diagnostic test could be employed as often as the user desires to refine and correct for the advance of the disease.

In another embodiment of the invention, the display screen on the HMD may be curved slightly, so as to reduce the reflections of ambient light from the display, thus improving image contrast, and focusing more of the image on the eye peripheries. The slight curvature may also reduce the optical distortion (keystone) in the screen image geometry, especially farther away from the central portion of the display, were no or little image is displayed in the case of macular degeneration.

In another embodiment of the invention, normal corrective glasses/lenses may be used and a film, like 3M translucent rear projection film, may be simply affixed to the corrective lenses, or the corrective glasses may be affixed to the OLED material so that the user has both his correction and the pixel manipulation in the same set of lenses.

In another embodiment of the invention, the correction for typical non-retinal problems of the eye like astigmatisms, myopia, hyperopia, or presbyopia, a type of farsightedness in which the ability to focus on nearby objects is gradually diminished as the aging eyes' lenses lose elasticity, may be done in the MCC. Pixel correction may be combined with the pixel manipulation techniques so that that the displayed video image corrects and compensates for that person's native other visual impairments, by using algorithms that adjust for the myopia or hyperopia through techniques like increased focus, increased contrast, and enlargement of the video with known techniques like fixed parallax barriers, lenticular lenses, pre-filtered light display, switchable liquid crystal barrier or display, multilayer display, diopter adjustment with independent eye focus, or pre-filtered light field display and the deployment of self-illuminating pixel technologies in the display and specialized lenses on the camera to correct for the non-macular problems of the eye, such as astigmatisms, myopia, hyperopia, or presbyopia. In this way, the invention may replace corrective optics to correct vision, with computations within the software and other aids. In another embodiment, the camera lenses may have the correction needed or may work with the computed correction in software.

If the camera lenses are not corrective, then the image correction may be made in the software, firmware, or hardware, so that the device may correct for both the loss of sight, like in macular degeneration, and also for problems like myopia. In this fashion, a person wearing the HMD system may obtain two types of correction in the same display, one for the macular degeneration and another for the nearsightedness or farsightedness. In this situation, the invention teaches that by pre-filtering, the video on the display may compute a pre-filtered light field, or use other similar technologies, which may result in a desired projection of the displayed image on the retina of a user or users, which may correct for their exact eye problem. By eradicating the rays that do not directly hit the retina at the precise angle necessary for the best correction, a user's eye prescription may be obtained without the need for corrective glasses. In other words, the correction computed into the video may be adjusted on the fly or in real time by the user via a fiducial marker, D-pad, or control pad ("focus controller"). An adjustment on the control pad may automatically correspond with a change in the filtering so that a more precise image is displayed on the lens and on the retina of the user's eye. This correction may be done for each eye, so that the display on one eye is different than the display on the other eye and each eye display may be adjusted independently by the focus controller. Also, the problem of scanning or eye-tracking may be solved by having the cameras needed for the correction on the smart contact lenses, which may then permit the camera's input and displayed images to match that of the movement of the eyes. The eye-tracking may be used in the medical application of the glasses, as well as for industrial and commercial and other application solutions. The eye-tracking subsystem may work through hardware and software to ensure that the image of the computer-mediated video information is directed to the appropriate position on the lenses where the eyes are gazing. The eye-tracking may be useful, not only for positioning of the video images, but to monitor fatigue of the wearer, or to alert in the instance that a wearer is intoxicated or under the influence of drugs. This can be helpful to alert corporate management concerning potential hazards in settings like an assembly line.

The system may utilize real-time gesture recognition technology, which may let the user use his or her hands for interaction and control of virtual or even real objects.

The software may recognize and tracks the 27 degrees of freedom (DOF) of motion. This may provide real-time, accurate hand-tracking and hand control combined with depth information. The technology may handle dynamic gestures, such as squeeze, swipes, tapping, grab and release, and finger motions such as pointing, pinching, waving, etc., which may enable users to execute computer/audio/visual commands with their hands and fingers. The hand control may be used in combination with the eye-tracking for camera control.

The system may include simultaneous localization and mapping (SLAM), which may work in combination with the GPS installed in the hardware. SLAM may be software and hardware which senses an unknown environment and recognizes and maps objects and pathways while simultaneously keeping track of a user's location. SLAM may enable accurate mapping where GPS localization is unavailable, such as indoor spaces, by using sensor data to simultaneously locate objects for a user in an environment and generate a coherent map of their surroundings. The simplest form of this technology may recognize walls, barriers, obstacles, and floors. This may then be used to help a user better understand his/her environment and prevent a wearer from falling over a curb or furniture, or to navigate through multiple obstacles. The SLAM technology may provide measurement and situational awareness and may be used in the control of drones and robotics. In other augmented reality applications, the SLAM technology may enable the positioning of complex 3D models in tracked scenes, ensuring accurate visualization and best positioning from the real to virtual environment.

The system may include object recognition sensor technology.

The software may have a process for identifying a specific object in a digital image or video taken by the cameras. The object recognition algorithms may rely on matching, learning, or pattern recognition algorithms using appearance-based or feature-based techniques. Objects may even be recognized when they are partially obstructed from view. This may be useful for partially sighted users, as the system can call out a couch, step, or other obstacle which might pose a danger to the user.

The headset may include a speech recognition and voice command software subsystem, which may interact with internally loaded software and apps. The user may be able to tell the subsystem to do anything that could be done with a keyboard or gesture control to command the system. The subsystem may be able to open browsers for the user, including new tabs, and open apps on the headset for viewing or searching. When used with hand gesturing and control, a user may be able to voice command a specific virtual menu to appear, then use hand gesturing to make a selection from the virtual menu. The voice subsystem may also be used to control, add to, subtract from, or otherwise manipulate pictures, text, or documents. For example, one a user has a document open, the user may be able to dictate text and the user's words may instantly appear.

In another embodiment, the augmented video may be displayed on the lenses and include the central 10 to 60 degrees FOV, for example, but could be in any case more or less either way. This displayed video may encompass phases one and two. Then the stitching techniques may be employed on the edges of the phase two augmented video, here, in this example, beginning at 60 degrees FOV. They may be projected/displayed, for example, on another 20 degrees FOV to re-interpolate and phase back into real-world, non-adjusted video. Pixel mapping techniques may help better retain image edge features and produce higher accuracy of integration of a real-world image projection. Thus, a user may have his or her central-most vision augmented via the projected video, while the video further from the central vision may be reintegrated into the real world non-adjusted video, while there may be no video on the outermost peripheral areas where actual vision is used.

In one aspect of the present invention, the data comprising the visual model may be filtered or transformed to eliminate noise or other undesirable effects within the data prior to the boundary or boundaries being established. This process may be performed automatically using a set of predefined operations, or may be performed under the control of an operator of the model view controller 14. For instance, the data may be filtered using one or more morphological transformations. Possible morphological transformations or operations may include, but are not limited to: erosion, dilation, opening, morphological gradient, top hat, and/or black hat. An initial boundary may be established using pre-filtered data and a secondary boundary may be established after the data has been filtered or transformed. The initial and secondary boundary may be compared automatically or by the operator to optimize the boundary used. Alternatively, Boolean operations may be used to filter the visual model and/or combining boundaries.

In another aspect of the invention, the pre-filtering may also include the pixel manipulation which, by using a parallax filter or other filter, may permit only the pixels that are rays that are at such an angle to miss the area of defect to be projected.

In one aspect of the present invention, the threshold may be adjustable, either at the model view controller 14 or at the display controller 16. If performed at the model view controller 14, this may provide control to the operator. In adjusting the threshold, the operator may optimize the boundary. If performed at the display controller 16, control may be provided to the user. This may allow the user to adjust the boundary to optimize the boundary for current conditions.

Figure 22:
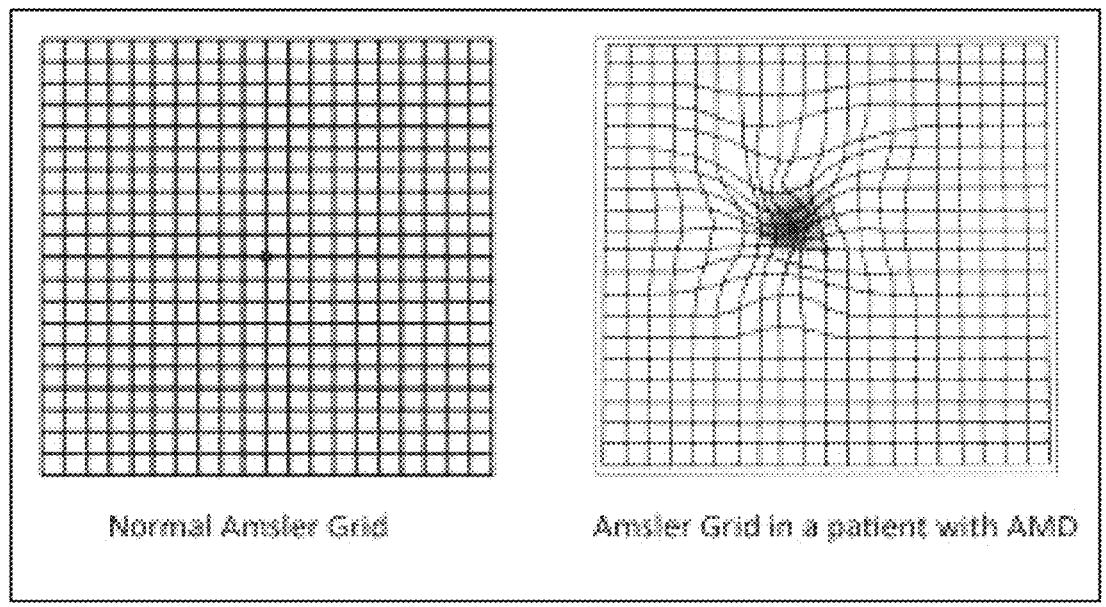
FIG. 22 is a graphical illustration of an Amsler map of a patient with normal vision and an Amsler map of a patient with AMD.

In one method for making sure that the digital pixel manipulation exactly replicates that of the analog eye, a fiducial marker may be connected to the diagnostic system resident in the HMD. A fiducial marker is an object placed in the field of view of an imaging system which appears in the image produced, for use as a point of reference or a measure merging the analog world with the digital world. Its applications are often seen in commercial products like virtual games. It may be either something placed into or on the imaging subject, or a mark or set of marks, as is preferable in this instance, in the reticle of an optical instrument, which is the measured camera and display. This diagnostic system may be combined with the pixel manipulation system such that the input of the diagnostic system may cause the pixels identified by the user as non-sighted or defective to be moved to a different location, as is more fully explained below. In the diagnostic state, Amsler grid may have been included in the software to be projected onto the lenses. A sample Amsler grid of a person with normal vision and a sample Amsler grid of a person with AMD are shown in FIG. 22.

The fiducial marker or mouse or other similar device may be connected to the software so that a location on the visual grid the user sees corresponds to the virtual grid resident in the software. The user may then look through the glasses at the grid and utilize the fiducial marker to identify the exact edges of the non-sighted space, which may then be converted or identified by the fiducial marker software or firmware as the space from which pixels and images must be moved and manipulated. In another embodiment, the output of a wearable FOV test may be used. For example, the embodiment may use an automated program embedded in the wearable HMD/HUD display device 50, 60. An initial start-up and mapping routine may be performed by observation, such as looking at an Amsler grid or moving objects to check the UFOV, or both, utilizing an existing FOV map to modify and optimize. Eye tracking technology may be used to ensure more accurate FOV mapping and validating fixation. Since eye movements can be as fast as 600 deg/s. and the smallest time constant for saccades is around 50 ms, and the smallest saccades could be completed in 60 milliseconds, it is possible for the reverse cameras which are a part of the CIS to look at the eyes to sample eye movements at a rate of 1 kHz which will allow sufficient precision of tracking of the eyes to let the system know how to modify the output in near real time for epipolar geometry and line of sight offsets. This result may be immediately usable directly as the digital input for the UFOV for the matrix mapping technology.

Figure 6:
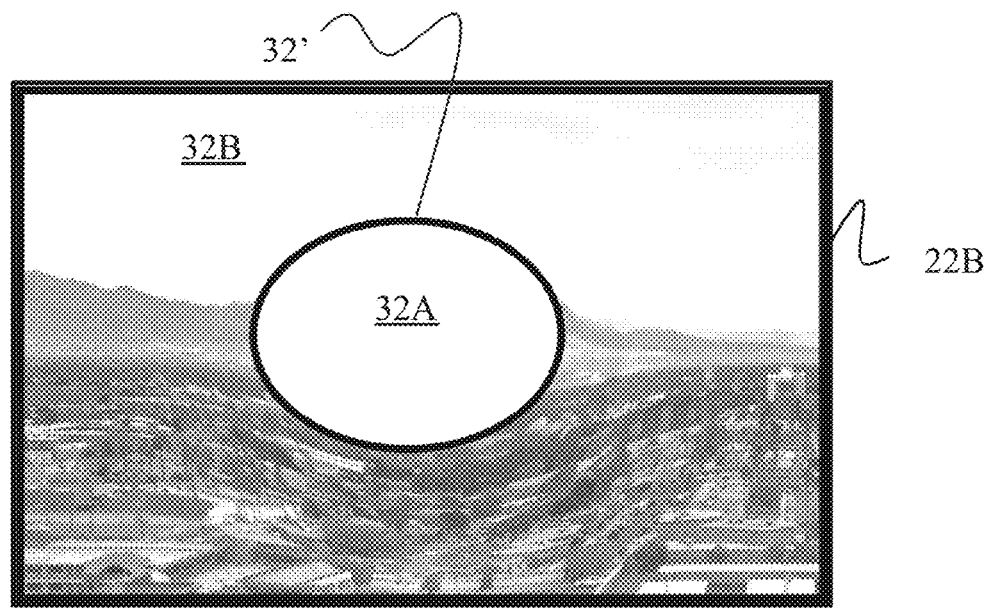
FIG. 6 is an illustration of a simple boundary comprised from one of a plurality of predefined shapes.

In another embodiment of the present invention, the boundary 32 may be adjusted or replaced with a simpler form (boundary 32', see FIG. 6). For instance, the boundary 32 may be replaced with a boundary established as a function of one or more predesigned shapes and the visual model. The model view controller 14 may utilize a set of predefined shapes, for example, rectangles, triangles, and ovals that are sized to include the affected area. The model view controller 14 may select one or more shapes automatically, or the process may be performed by, or with the assistance of, the operator.

Figure 7:
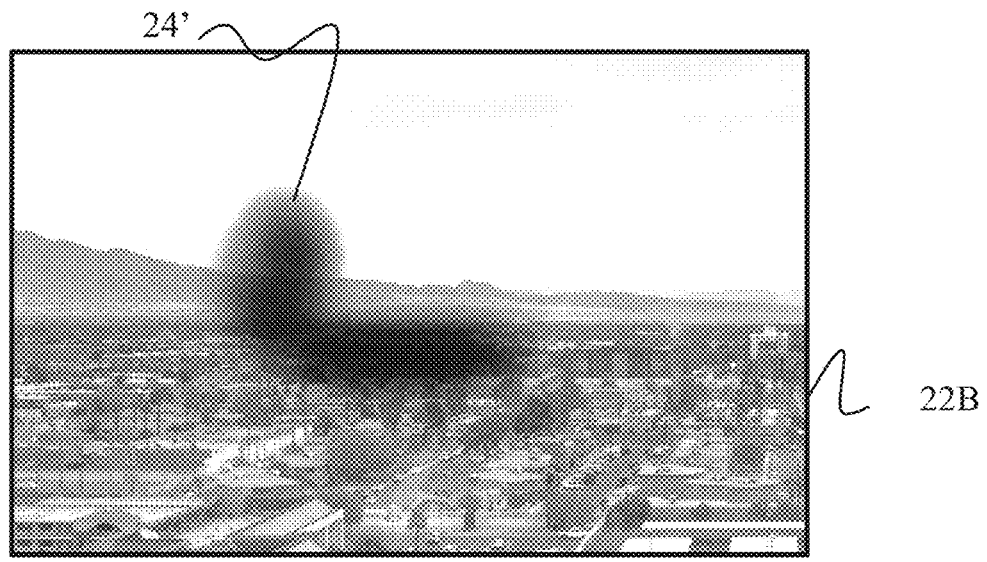
FIG. 7 is an illustration of a patient's vision with a more complex defect.
Figure 8:
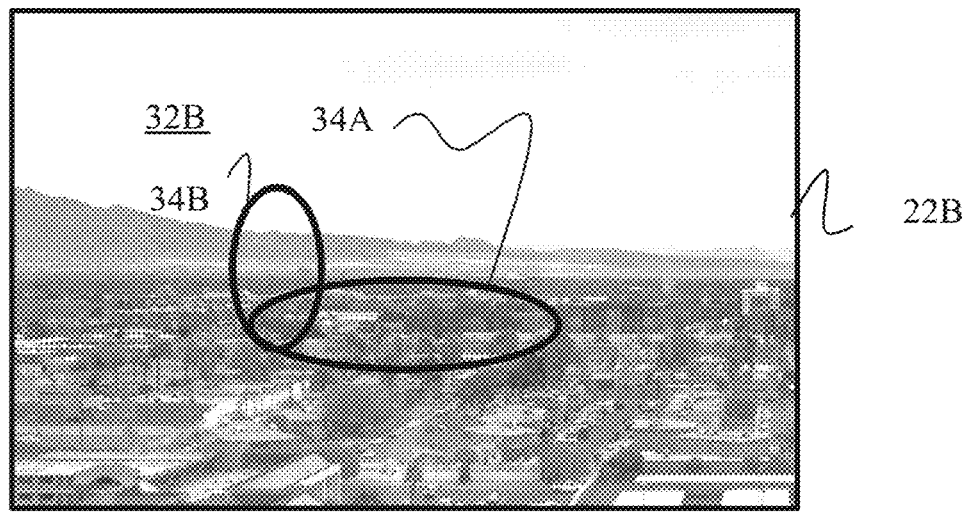
FIG. 8 is an illustration of a boundary associated with the illustration of FIG. 7.

With reference to FIG. 7, the shape of the defect or damaged area 24' may be more complex. A complex boundary may be established using the threshold process identified above, or by some other method. Alternatively, the initial boundary may be replaced automatically, or with operator input using one or more of the predefined shapes sized to cover the defect or with the results of the user using the fiducial marker. In the example of FIG. 8, two shapes 34A, 34B are used. The boundary may be formed by the outer edge of the joined shapes.

Figure 9:
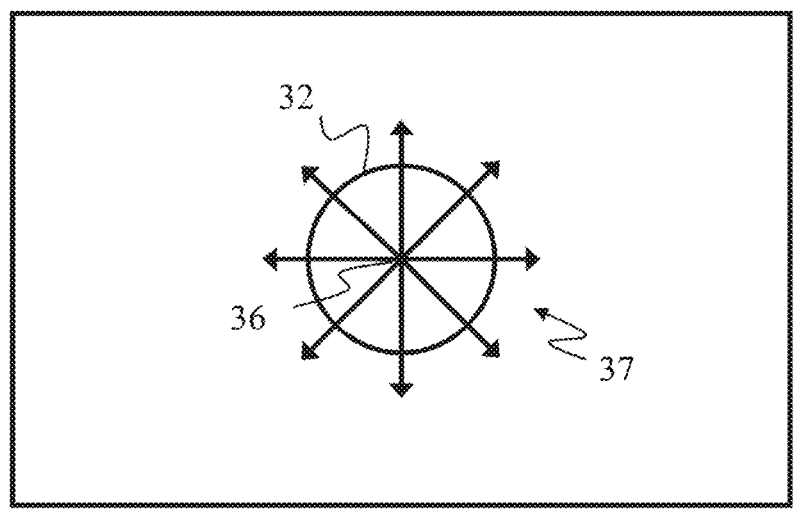
FIG. 9 is a diagrammatic illustration used in establishing a retinal map, according to an embodiment of the present invention.
Figure 10:
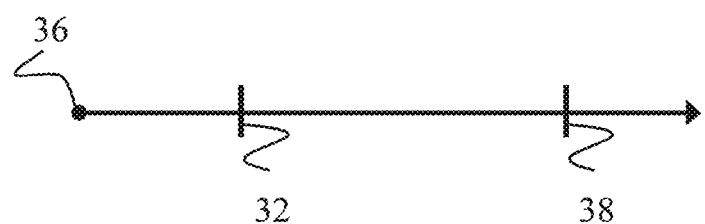
FIG. 10 is a diagrammatic illustration used in establishing a retinal map, according to an embodiment of the present invention.

With reference to FIGS. 9 and 10, in one aspect of the present invention, the image data inside the boundary 32 may be shifted outside of the boundary 32. In the example shown in FIG. 9, first a center point 36 may be established. The center point 36 may be an actual center of the boundary if the shape of the boundary is regular, or it may be defined by finding or estimating the center of the shape defined by the boundary, or the center point may ignored and the other items as described above may be used to determine how a pixel is moved. In one embodiment, image data along a plurality of rays 37 starting at the center point and extending outward may be shifted outside of the boundary. It should be noted that in the above examples, the areas inside the boundary or boundaries are defective. However, in some situations, for example, where peripheral vision is affected, the area inside a boundary may be associated with good vision and the areas outside of a boundary may be associated with poor vision.

In one embodiment, the retinal map may include a series of data points which overlay the digital model. The data points may be laid out in a grid in a regular pattern approximating the Amsler grid. Each data point may be defined by a set of X,Y coordinates relative to the image data. As explained in detail below, each data point may be assigned a set of coordinate transformation values ($\Delta X$, $\Delta Y$), which may be used to transform the image data. Each data point may lie on a single ray and one or more pixels, which extends outward from the center point 36. For each data point, the associated ray may be found and a set of coordinate transformation values ($\Delta X$, $\Delta Y$) may be established based on a set of predetermined rules. The coordinate transformation values ($\Delta X$, $\Delta Y$) may be used as coefficient values in the transformation equations below.

In one embodiment, visual information in the image from the camera may be radially shifted from a central point. For instance, in one embodiment, the image data from the center point 36 to the edge of the image 38 may be compressed in the corrected image from the boundary 32 to the edge of the image 38. Thus, the coordinate transformation values ($\Delta X$, $\Delta Y$) for any data point lying on the ray may be calculated based on the length of the distance from the center point 36 to the boundary 32, and the length from the center point 36 to the respective edge of the image 38. This may work better in an immersive environment where the concern for the moved edges is non-existent.

Figure 11:
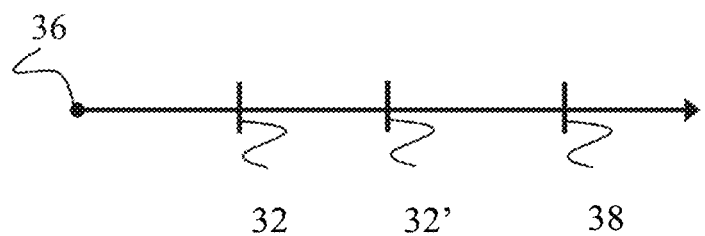
FIG. 11 is a diagrammatic illustration used in establishing a retinal map, according to another embodiment of the present invention.

In an alternative embodiment, the coordinate transformation value ($\Delta X$, $\Delta Y$) may be calculated such that the visual information is disproportionally shifted from the center point. For example, with respect to FIG. 11, visual information from the center point 36 to the boundary 32 may be shifted to a segment of the ray defined by the boundary 32 and a point 32'. The length between the boundary 32 and point 32' may be equal to or different than the length between the center point and the boundary 32. In this embodiment, the visual information between the boundary and the edge of the image 38 may be compressed between point 32' and the edge of the image 38. Not only can the visual information be shifted out towards the periphery, but can also be accomplished in reverse and the visual information can be shifted inward as well.

Once coordinate transformation values are established, the retinal map may be stored in the database 12 and transferred to the display controller 16. In use, the retinal map may then be used to transform the image(s) received from the camera and generate the corrected image(s). The corrected image(s) may then be displayed in real-time via the display unit 18.

In one aspect of the present invention, the visual information may be transformed or moved at each data point. The visual information between the data points may be transformed using a spline function, e.g., a B spline function, to interpolate the visual information between the data points. In another aspect of the invention, the pixels relating to the data portion of the image which is moved may be reduced to smaller pixels, such that the moved pixels and the pre-existing pixels occupy the same space on the display. Alternately, the removed and replaced pixels may be interlaced into a video frame consisting of two sub-fields taken in sequence, each sequentially scanned at odd then even lines of the image sensor. In another aspect of the invention, the pixels may be manipulated by fixed parallax barriers, pre-filtered light display, or switchable liquid crystal barrier or display. The parallax barrier may cancel out the pixels that have an undesirable angle and permit the ray bearing pixels which do have the correct angle of projection onto the retina to pass. Likewise, the other technologies will only let certain rays through to the retina, which can be used for the cut-out and repositioning of the pixels. In another embodiment of the invention, the prescription for the use may be included in each camera lenses so that the correction is done at the lens stage with lenticular lenses, progressive lenses, bifocal or trifocal lenses, and the like before or at the same time as the other modifications identified in this patent.

The display controller, in generating the corrected image, may shift visual information within the corrected image in a first area inside the boundary to a second area outside of the boundary as a function of the series of data points. The coordinate transformation values may be used to shift image data that exists inside the boundary to an area outside of the boundary. In the above example, the second area is defined as any area in the image that is outside of the boundary.

Figure 4C:
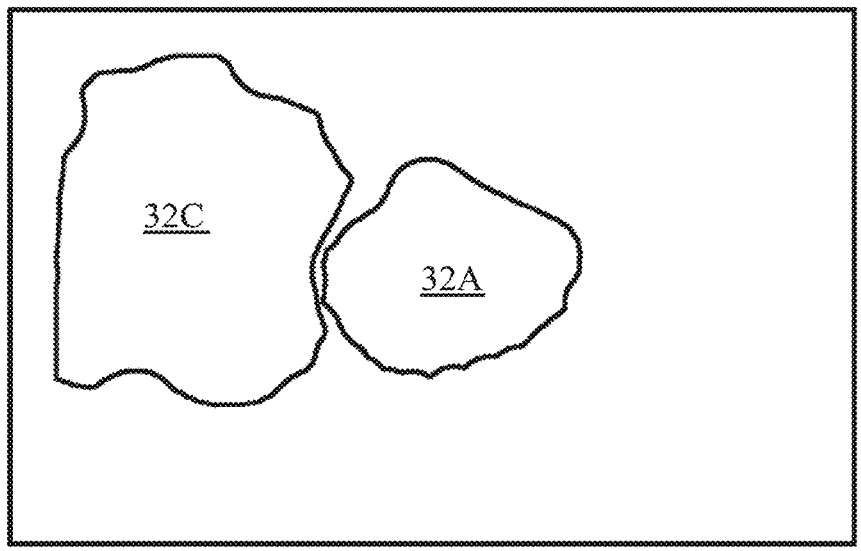
FIG. 4C is an illustration of first and second boundaries, according to an embodiment of the present invention.
Figure 4D:
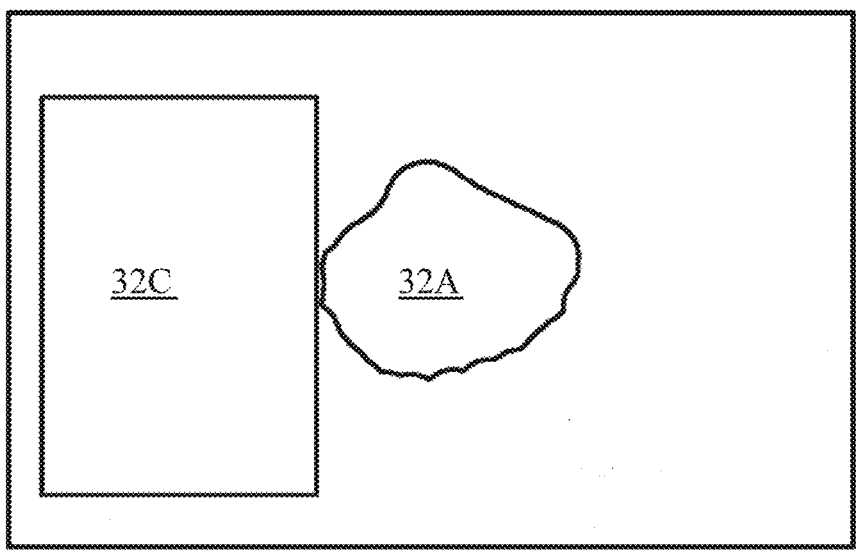
FIG. 4D is an illustration of first and second boundaries, according to another embodiment of the present invention.
Figure 5:
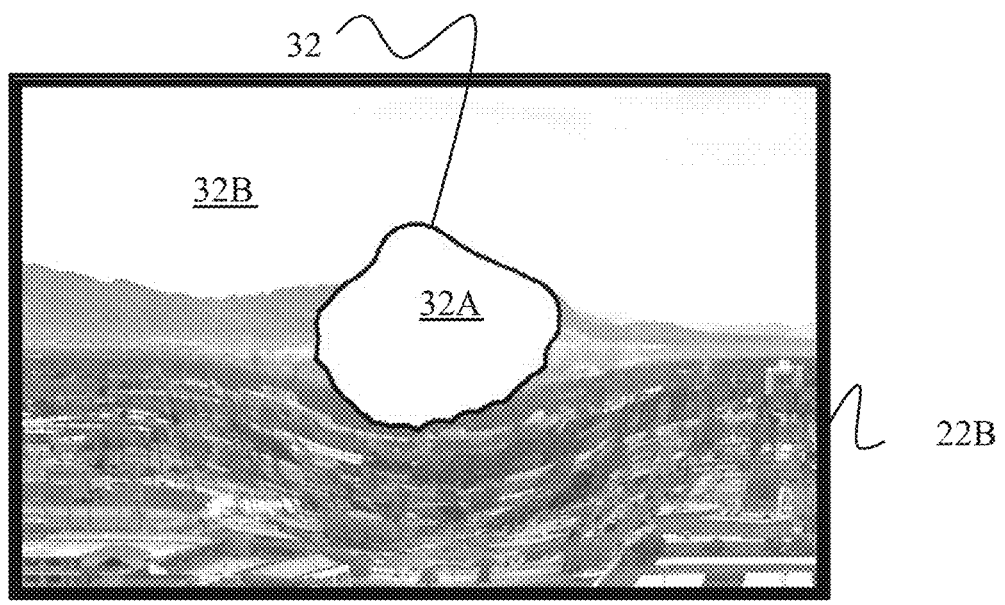
FIG. 5 is an illustration of a complex boundary, according to an embodiment of the present invention.

In another embodiment, the second area may be defined based on the data in the visual model. For example, a second boundary may be established as a function of the data in the visual model. In one example, the second boundary may be established based on the visual model that meets predefined criteria. For example, an area within the visual model may be established cells 28 in the grid 30 that have a value that meets predefined criteria. In the example above, for instance, the second boundary may encompass an area of the grid 30 in which the cells 28 have a value of 3 (or some other threshold) or less. In this embodiment, the information inside the first boundary 32 is shifted (proportionally or disproportionally) into the area defined by the second boundary. Examples of an area defined by a first area 32A and an area defined by a second area 32C are shown in FIGS. 4C and 4D. In both examples, visual information in one of the areas 32A or 32C may be shifted towards or into the other one of the areas 32A, 32C. In the illustrated examples, the second boundary in FIG. 4C has been replaced with a simpler shape/form in FIG. 4D.

In one aspect of the present invention, the display controller 16 and the display unit 18 may be implemented in a suitable user wearable device, such as smart glasses or head mounted displays (HMDs). In all cases, these hardware wearable platforms may contain wearable glasses that contain one or two forward mounted cameras, an onboard microprocessor, and display technologies for viewing by the eye. Furthermore, these are usually battery powered, as well as able to plug into a PC in order to upload information via a USB cable etc. and/or for charging. This may also include HUD (Heads Up Displays). The HMD may be worn over a user's existing glasses with prescription lenses 62 in order to facilitate moving between the two modes of normal vision and the augmented IDM (Image Distortion Map) vision. Alternatively, a virtual retina display maybe used to project photons directly onto the retina, or a smart contact lens may project the image that is worn on the eye. Any suitable method or device to present the correction image or images to or onto the eye(s) may be used. Alternatively, the image or images presented to the user may be otherwise opaque such that the outside world is not visible.

Figure 12:
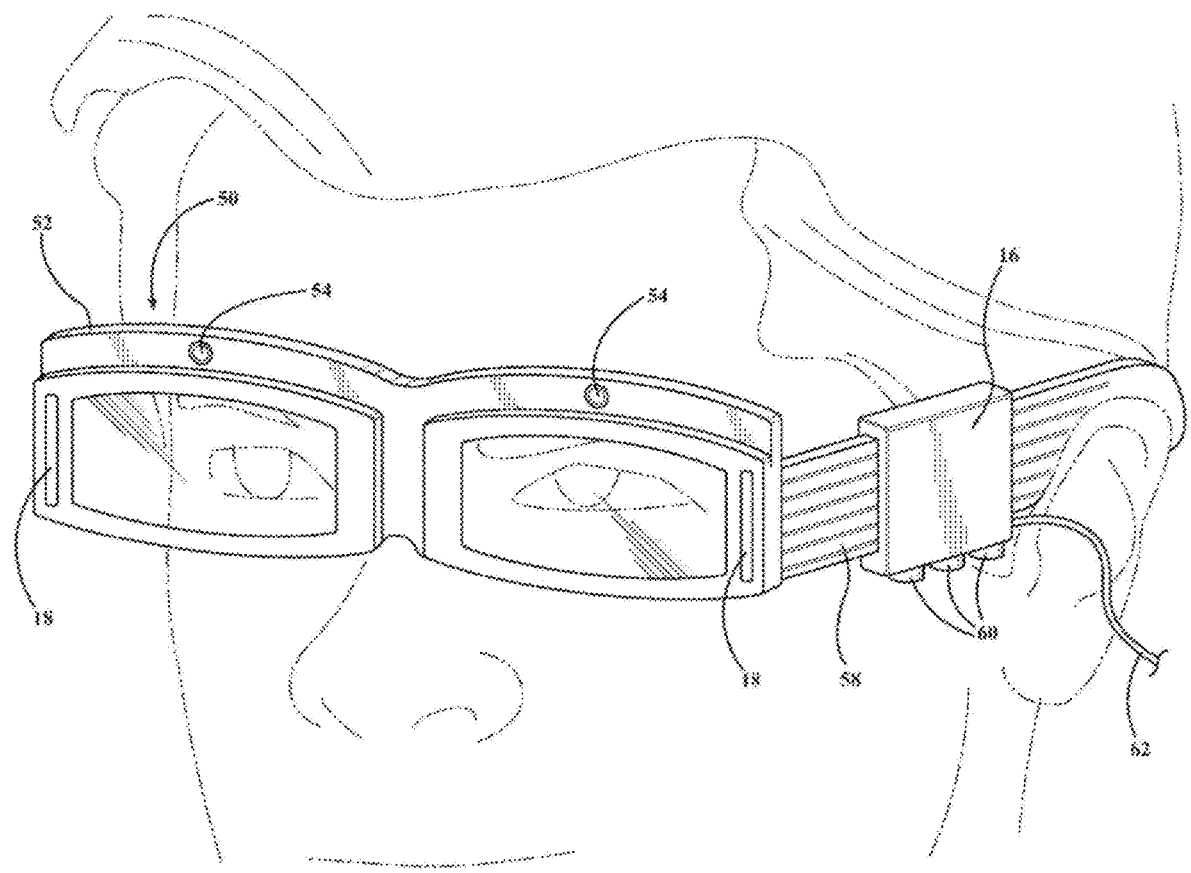
FIG. 12 is a diagrammatic illustration of a head mounted display unit, according to an embodiment of the present invention.
Figure 13:
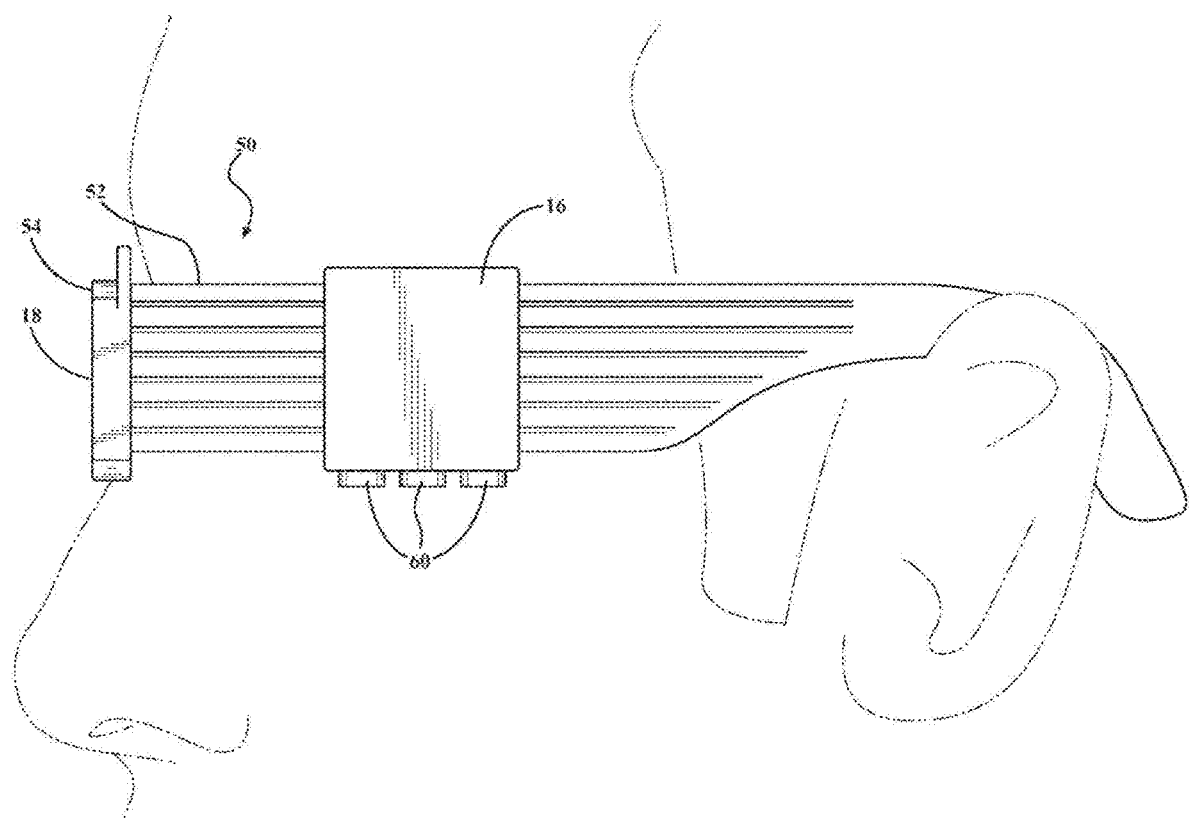
FIG. 13 is a second diagrammatic illustration of the head mounted display unit of FIG. 12.

With reference to FIGS. 12 and 13, in one embodiment, the display controller 16 and the display unit 18 are embodied in an exemplary head mountable display (HMD) device 50 that is worn by the user. In the illustrated embodiment, the HMD device 50 includes a set of wearable glasses 52 that contains one or two forward mounted cameras 54. The display controller 16 may be mounted to an HMD frame 58 and include an onboard microprocessor. The display unit 18 includes a suitable display technology for viewing by the eye. One or more input or control buttons may be provided that work in conjunction with suitable menus, and software controls display on the display unit 18 to allow the user to change options. The HMD device 50 may be battery powered and may include a USB cable or suitable port 62 to connect to, e.g., a computer to transfer data and software and/or for charging the battery.

Figure 14:
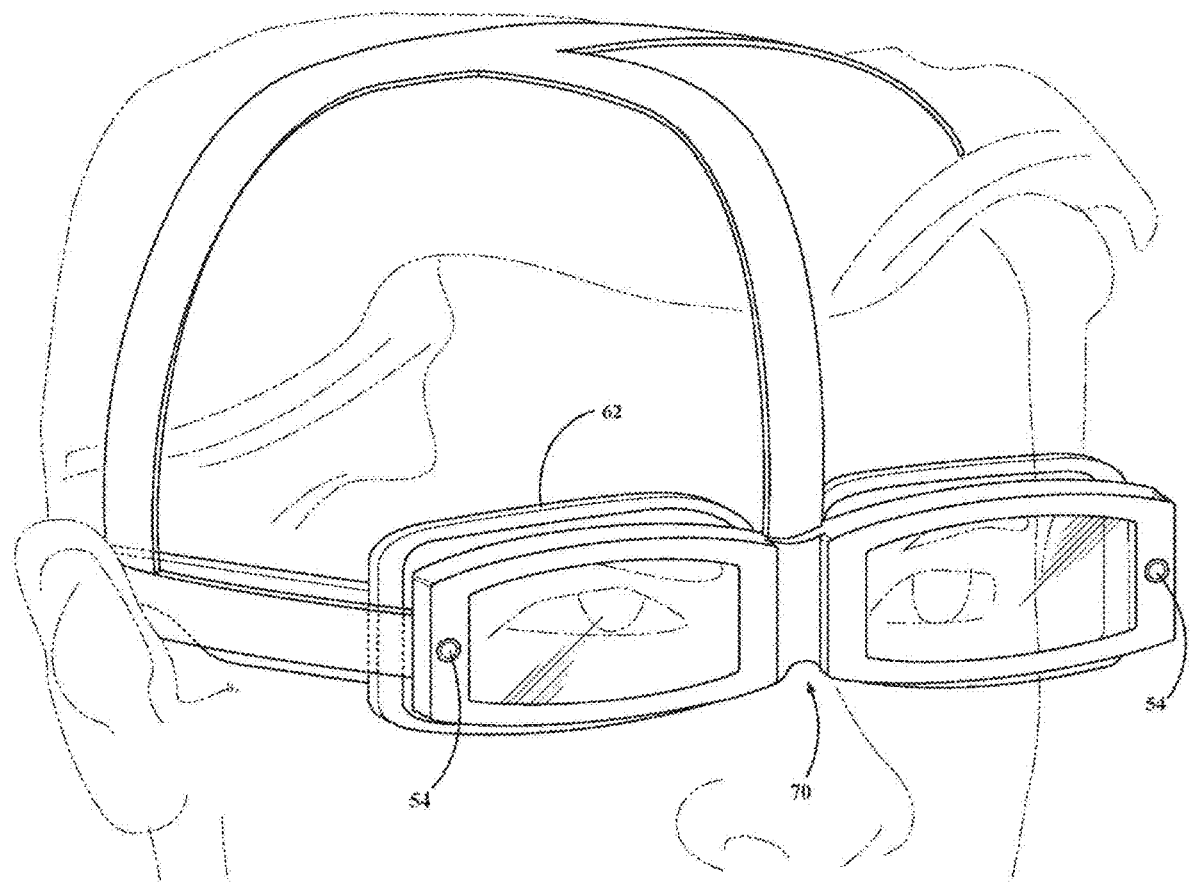
FIG. 14 is a diagrammatic illustration of a heads up display unit, according to an embodiment of the present invention.

With reference to FIG. 14, the display controller 16 and the display unit 18 may also be embodied in a heads-up display (HUD) device 60 that can be worn over a user's existing glasses with prescription lenses in order to facilitate moving between the two modes of normal vision and augmented IMD vision. The HUD display device 60 may be head mountable and may include different display technology such as separate LCD or LED type of display. The HUD display device 60 may embed a display on the actual lenses of the glasses themselves that overlay the image to view the augmented display in conjunction with the outside world.

Figure 15:
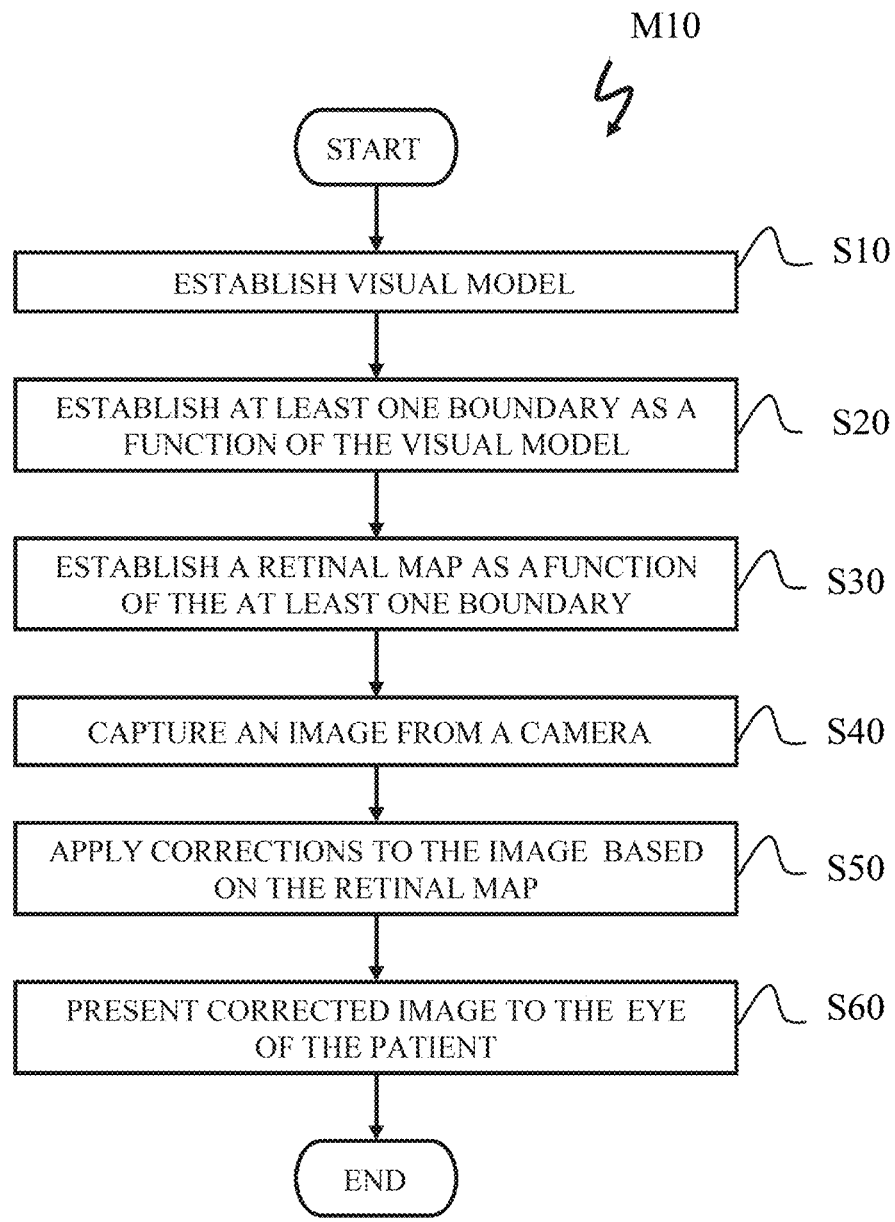
FIG. 15 is a flow diagram of a method for augmenting the vision of a patient, according to an embodiment of the present invention.
Figure 16:
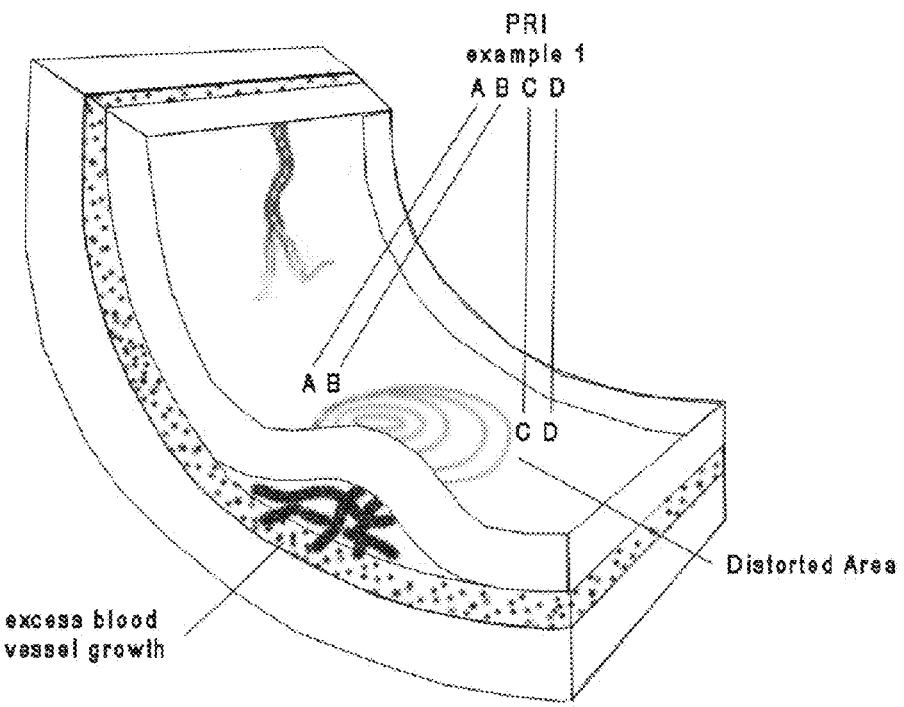
FIG. 16 is a graphical illustration of a first example of a manipulation of prescribed retinal interface, according to an embodiment of the present invention.
Figure 17:
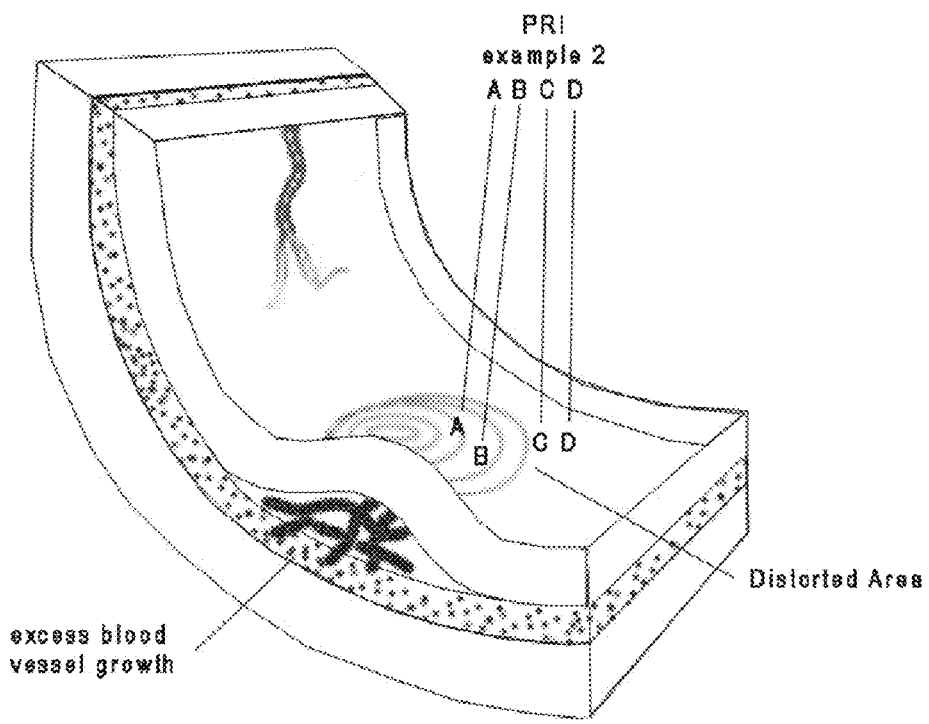
FIG. 17 is a graphical illustration of a second example of a manipulation of prescribed retinal interface, according to an embodiment of the present invention.

With reference to FIG. 15, in another aspect of the present invention, a method M10 according to one embodiment of the present invention is provided. In a first step S10, a visual model associated with a user is established, by the model view controller 14 and stored in the database 12. The visual model includes data related to a quality of the user's vision. In a second step S20, at least one boundary is established, by the model view controller 14, as a function of data associated with the visual model. At least one boundary is indicative of an area to be corrected within the user's vision. In a third step S30, the model view controller 14 establishes a retinal map as a function of the boundary and stores the retinal map in the database 12. The database may be incorporated into a semiconductor chip, which may also be existing space in a camera chip.

In a fourth step S40, an image from one or more cameras associated with the user is received by a display controller 16. Corrections to the image based on the retinal map are applied to the image and a corrected image is generated in a fifth step S50. In a sixth step S60, the corrected image is received at the display unit 18 and presented to the eye of the user.

The system 10 and method M10, in general, may remap portions of the image(s) captured by the camera(s) which would be viewed by the affected portions of the user's eye(s) to the periphery or unaffected portions of the user's vision, or alternatively to another portion of the user's retina. With this mapping correctly executed, the user's brain may adapt quickly and effective central (or periphery) vision may be mimicked. This may be accomplished with the forward-looking cameras as the sensor that captures the real-world image. The system 10 and method M10 of the present invention may shift the pixels to form a corrected image or series of images which may be displayed on the micro-displays on a head mounted device, such as readily available augmented reality and virtual reality glasses. This process may all be non-invasive and may depend only on the processor in the glasses, the remapping software, and the user's brain processing power through direct observation of the micro-display. The display device utilized may be implemented in head mounted devices, suitable examples of which are these offered by companies such as Sony, Epson, Facebook, Google, etc., utilize a variety of display technologies, such as LED, LCD, OLED, Photon Retinal Display, Virtual Retinal Displays, and Heads Up Displays.

Field of Vision Mapping

In order to correctly enable the pixel remapping technology of the present invention for enhancement of central vision (for the macular degeneration case) and other blindness conditions, the initial mapping of the UFOV (usable field of vision) may be digitally generated. It should be noted that the present invention is not limited to mapping from a center area to a peripheral area. In some cases, peripheral vision is affected and the mapping may be from the peripheral area to the center. There are a multitude of methods to accomplish this task. In all cases the initial examination, mapping, and calibration may be converted to a digital file. This digital file may then be used to construct the boundaries of the UFOV. The UFOV may be treated as a sharp outline where peripheral or useable vision is clear and not degraded. However, this boundary may be a result of evaluation and determination of the gradation of the partial vision, then interpreted to construct the UFOV boundary. This UFOV border may then be utilized as the baseline for the IMA (image mapping algorithm) to determine the area where the effective central vision can be mapped into, along with the existing effective peripheral vision. There are numerous ways to construct the initial UFOV boundary conditions, both through direct digital means and by manual approaches that can be then converted to a digital file. In some of these cases, the FOV test may be administered by a trained medical professional such as an optometrist or ophthalmologist in the doctor's office. In other cases, an automated FOV test may be self-administered with the proper digital technology. In the third case, a trained professional can manually administer an FOV mapping test to generate the UFOV. Any, and all, of these cases may be utilized to generate the UFOV as outlined.

Figure 18:
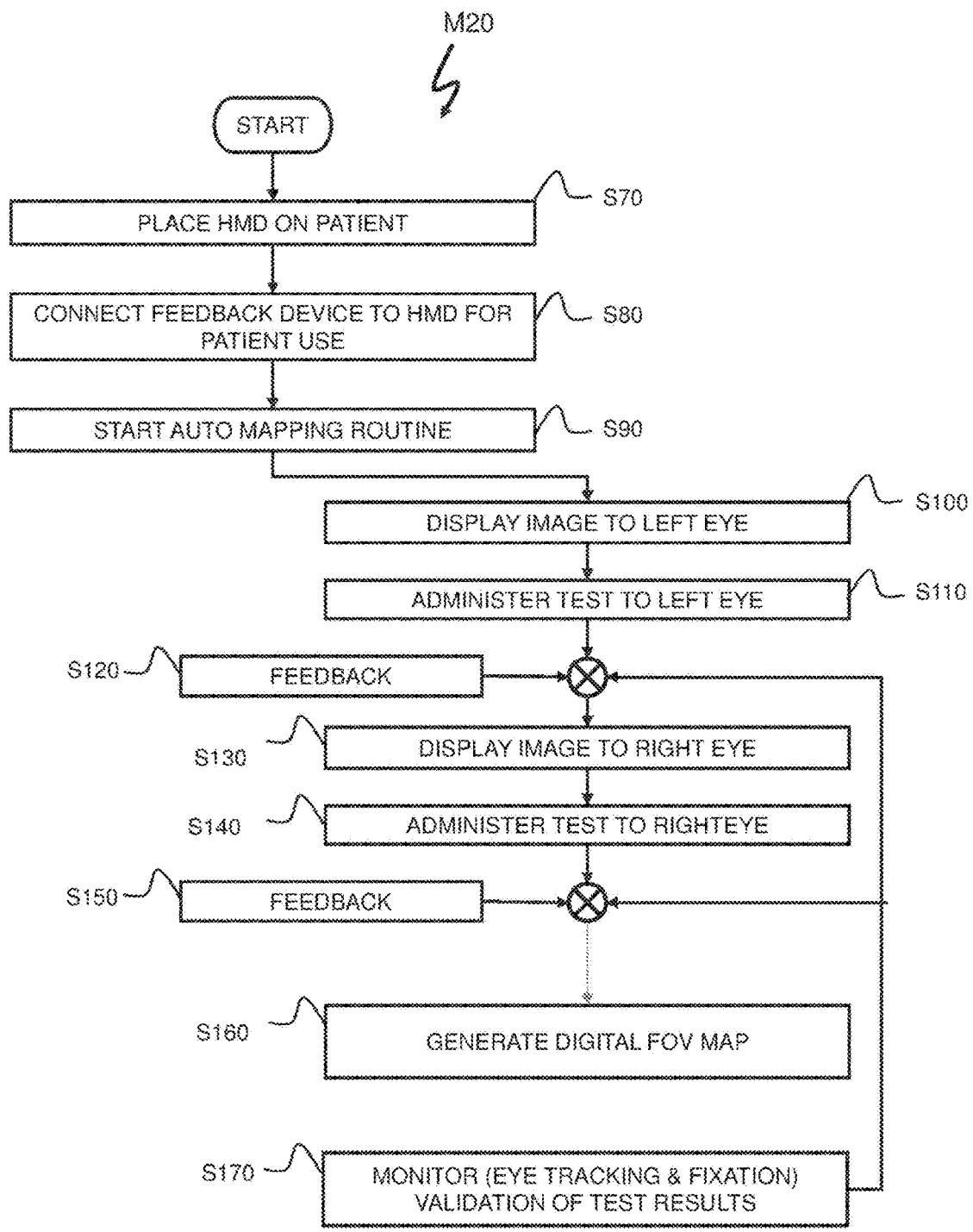
FIG. 18 is a flow diagram of a process for establishing a digital field of vision map, according to an embodiment of the present invention.
Figure 19:
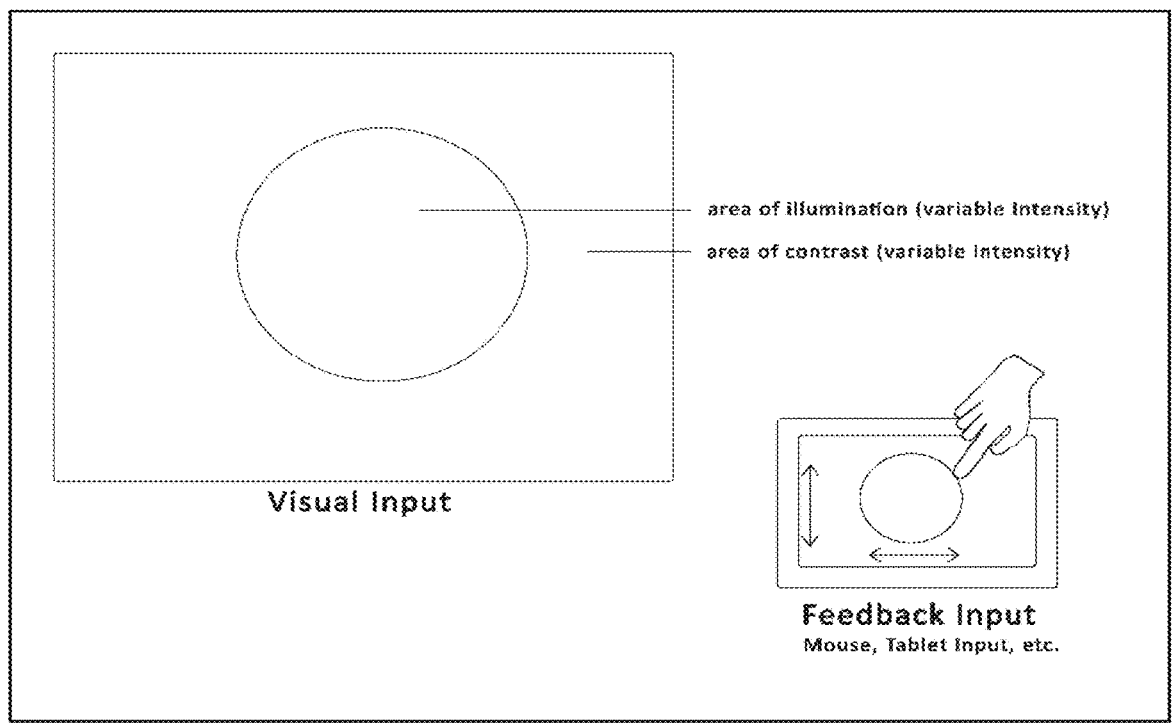
FIG. 19 is a graphical illustration of a first portion of the process of FIG. 18.
Figure 20:
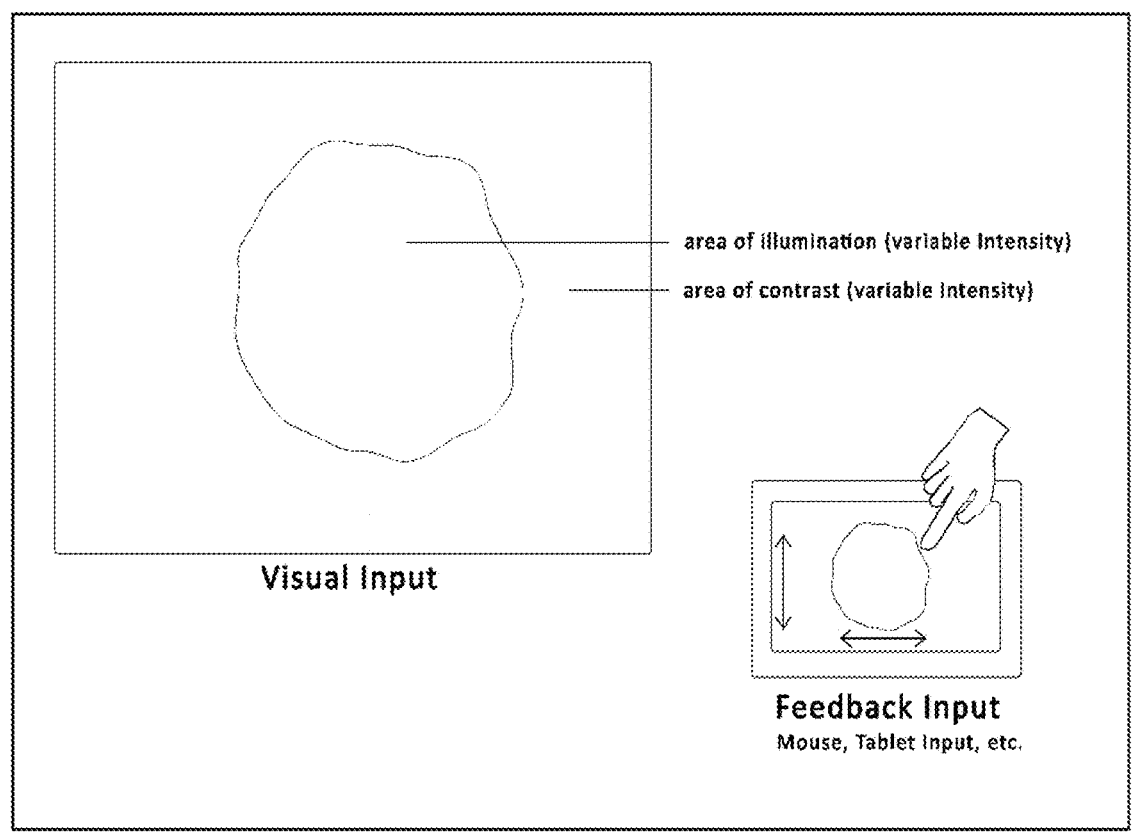
FIG. 20 is a graphical illustration of a second portion of the process of FIG. 18.
Figure 21:
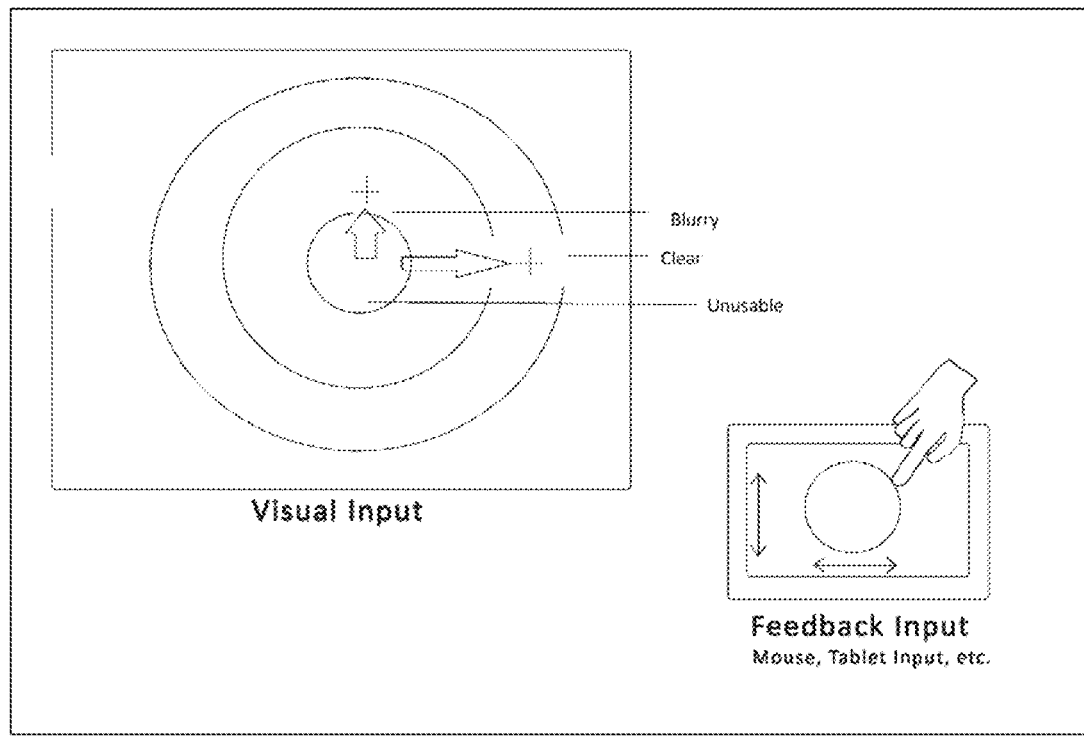
FIG. 21 is a graphical illustration of a third portion of the process of FIG. 18.

With respect to FIG. 18, the general process is embodied in a method M20. The general process is as follows:

1. The wearable HMD is placed on the user's head and would be put into "Diagnostic" mode for FOV mapping. (Step S70)
2. The wearable HMD is connected (via external cable or wireless communication mode) to a user feedback device, such as a PC with a mouse, tablet, and mobile phone (Step S80) or voice recognition technology where the user gives verbal feedback to the system, which recognized commands, clues, and instructions, and accomplishes the FOV mapping automatically.
3. The auto mapping routine is initialized. (Step S90)
4. Eye tracking and fixation are monitored throughout the FOV mapping process in order to determine valid results. Given that macular degeneration attacks the central vision, it is important that the fixation and focal point test is administered through markers or objects in the peripheral vision, as well. The valid results can be driven with a secondary feedback loop by constantly monitoring fixation and using only valid visual data points for the mapping of the UFOV, and retesting as necessary to develop the entire UFOV map. (Step S170)
5. The FOV mapping test is administered first for the left eye (or right eye) through use of visually moving along an Amsler grid to see where images are warped or straight. (Steps S100 and S110). Alternatively, a flashing object is generated to show at different points in the user's vision in order to determine visual acuity through the feedback device. This is performed at different level intensities to verify level of degradation of vision. See FIGS. 19 and 20. Alternatively, an object is moved through a series of sequences and with feedback, determined when the object becomes clear from blurry to unviewable, effectively creating gradations of the sight map. See FIG. 21. Alternatively, a constantly expanding sphere is displayed until the edges become clearly visible to the user. The edges are manipulated through the feedback device until the edge of the UFOV is determined. The latter two cases offer the advantage of a faster approach to FOV mapping for utilization with the wearable later. With a quicker mapping procedure, the system is less likely to cause fixation errors due to lack of concentration from the user. This also offers quicker calibration for more frequent tweaks to the UFOV map to optimize the performance. The further advantage that can be realized with the user's ability to manipulate the FOV edge is to better personalize the calibration to their particular affliction (Step S120).
6. The same test is then administered for the other eye (Steps S130, S140, S150).
7. The results are validated or invalidated based on verifying eye tracking and fixation, which is done concurrently while administering the eye tests (Step 170).
8. The Digital FOV map is then generated (Step 160). The auto-mapping and Digital FOV map can be created using voice recognition technology where the user gives verbal feedback to the system, which recognized commands, clues and instructions, and accomplishes the FOV mapping automatically.

This invention teaches the use of one or more cameras to capture the approximate line of sight of the user and display a corrected pixel manipulated version of the real world onto see through glasses or lenses though which the user looks. When the line of sight is not exact, then software may be used to realign the picture or video so that it most closely approximates the actual line of sight of the eyes. Alternatively, smart contact lenses may be worn with the cameras placed in the center of the lenses.

Further, software may be used for correction for the epipolar geometry correction, so that the image is corrected for when the eye is looking at long distances versus looking at something close. In these instances, a camera looking at the eyes or one eye may track the position of the eye and send information to the control subsystem.

Figure 23:
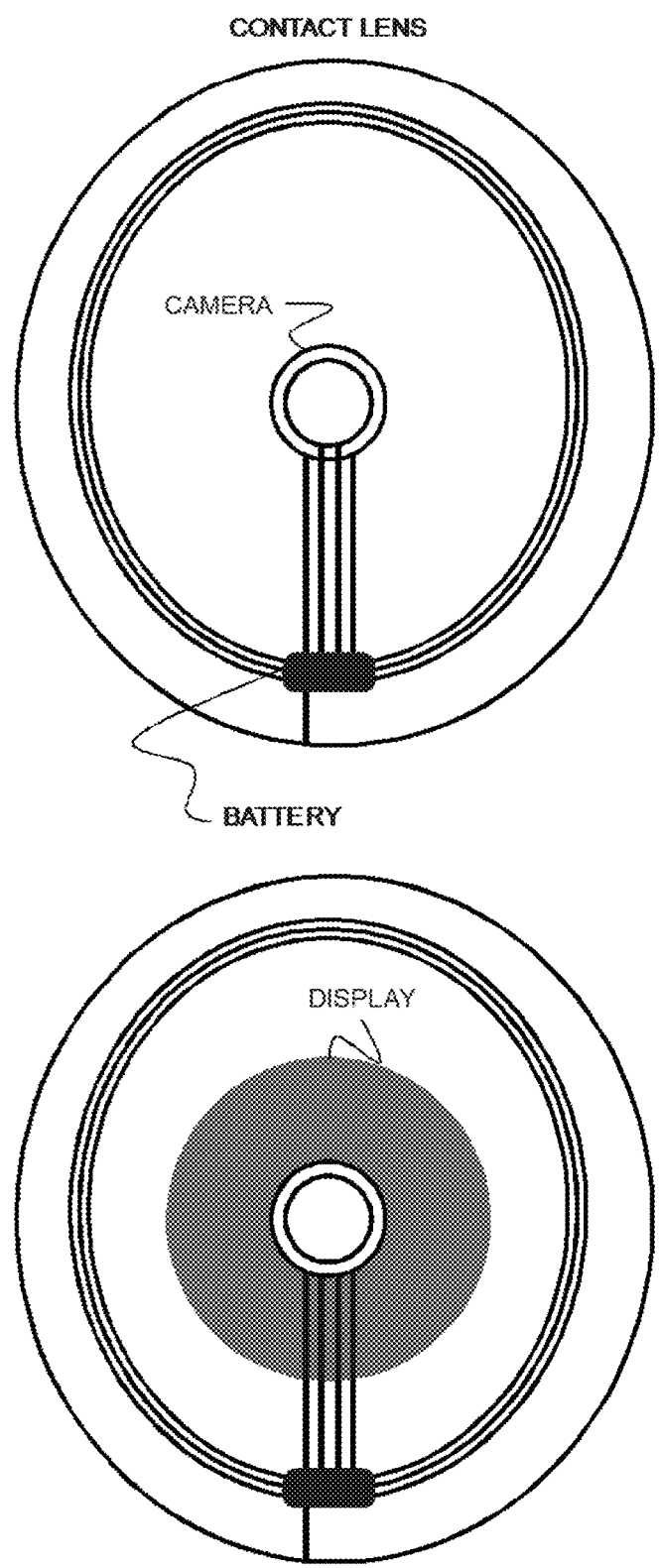
FIG. 23 is an illustration of a smart contact lens.

In one embodiment of the invention, smart contact lenses may be used in connection with glasses. The smart contact lenses (FIG. 23, 26) may have the camera placed in the area where the vision has been impaired or is non-existent. In this fashion, the image which is to be displayed on the lenses may have the same or near similar aspect as the rest of the normal vision because the cameras move with each eyeball and, when projected with a corrected image, can approximate the real-world vision.

In another aspect of the invention, more than two cameras may be used. The two or more cameras may be used to create stereoscopic vision or to simply project the same corrected image to both eyes. The reason that more than one camera per eye may be used is because each camera institutes its own distortion, and the larger the FOV that the camera captures, the more distortion. Thus, less distortion may be introduced in the example of one corrected image displayed for both eyes, captured by two cameras to create the entire FOV of over from less than 100% FOV to over 200% FOV. This is because it may be easier to use simple existing programs for blending or seaming the images from two cameras together than to use one camera that must originally capture an image which is up to 220% FOV and then correct for the lens distortion. This method may also be employed with the method described below for the employment of smart contact lenses, where the smart contact lenses may use one camera for a corrected display to both eyes, or may utilize one camera for each eye for a dual corrected display, or more than one camera for each eye/contact lens for a display to each eye or to both eyes. In addition to the positioning of the one or more cameras, the invention teaches that software/firmware can be used to correct the projected image for eye view aspect ratio, meaning to make the projected image look as though it was captured in the line of sight of the eyes. The use of smart contact lenses with camera(s) placed in the central vision non-sighted portion of the user's vision (the central vision or macular vision, see FIG. 23), may also correct the displayed image for triangulation and epipolar geometry so that a mono or stereoscopic image can be accurately displayed on the glasses/lenses or directly into the retina and be in aspect with the user's own vision.

Irrespective of where the camera or cameras are located, either on smart contact lenses or on the person or on the glasses or glasses frame, the image of the real world may be captured, then modified in accordance with the corrective modification software/hardware and then displayed on the glasses or a portion of the field of vision of the glasses. This can be done on one lens or on both lenses. In this fashion, the user may be looking at the real-world vision through the glasses while simultaneously an augmented, manipulated, and corrected (for that user) version is also displayed onto a portion of the glasses or lenses, where only the portion of the field of view which needs to be adjusted is modified. The goal of the new inventions in this patent may be to ensure that there remains some peripheral vision where real world images are reintroduced to the users FOV, which may be unmodified looking through the glasses and around the glasses/lenses so a person can use this peripheral vision to avoid hazards, ensure near navigation, be able to manage steps or other obstacles, or see hazards.

The corrected display onto the glasses, lenses, or retina may be accomplished with glasses or lenses using such technology as transparent OLED material, or such as Apple's Retina® HiDPI mode display, where the user interface image is doubled in width and height to compensate for the smaller pixels. In this invention, where the word pixels is used it also means a subpart of an image and light emitted rays of information which are to be broadcast to the eye and retina.

Figure 24:
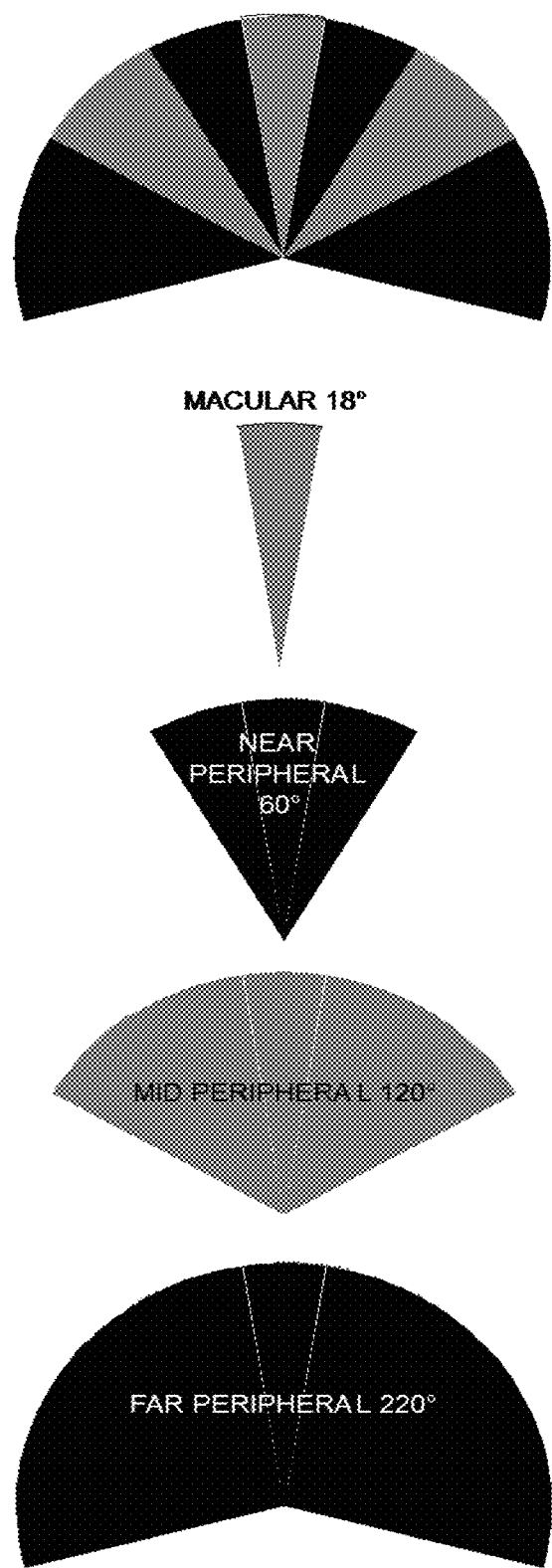
FIG. 24 is an illustration of the patient's macula.

In addition, see-through technologies that project opaque images via the use of wave guided images upon lenses, or the use of mirrors to project an image upon clear lenses, or technology such as clear rear projection film affixed to a person's prescription lenses may also be suitable. In addition, technologies which project images directly into the retina can also be employed. The goal of all of this may be to remove the image from the non-sighted portion of the user's vision within the damaged macula, as shown on FIG. 24, which may comprise about 18'% of the central FOV, and move those images to the near peripheral, which may comprise about the next 60% of the FOV (minus the 18% macular vision), and then reintroduce non-manipulated images into the mid-peripheral vision, which may comprise about 120% FOV, and leave no project on the far-peripheral, which may comprise the outermost 220% FOV, all of which combine in the mind to create one homogeneous image.

In this fashion, only the 30% to 60% FOV which needs to be manipulated may be augmented with pixel manipulated video, superimposed over the see-through lenses, leaving the actual real-world images for the user's mid and far peripheral vision to see, so that a user can see where to step, walk, move, and negotiate his or her real-world environment. While the estimate of 30% to 60% of the FOV being manipulated is stated here, in actuality anywhere from below 1% to over 100% of the FOV may need to be manipulated, depending on the user's impaired or missing FOV vision, and the adjustments to the FOV which need to be made to correct for that defect. Likewise, the de-modification of the image can occur in the near, mid, or far peripheral vision of the user, as necessary to get the best vision.

It is the teaching of this invention that merging the augmented and manipulated pixel video information may be superimposed onto some type of see through lenses or directly onto the retina. This augmented video display which is attempted to be constrained into the near-peripheral vision, as much as possible, may contain more FOV visual information (pixelated or otherwise) than originally exists in the real world. This is augmented video display is then merged with non-manipulated real-world information, which is already available through the see-through lenses.

In the instance of merging, the augmented video, which is the video which has had the pixels manipulated to show more FOV information than would otherwise exist in the real world, may be merged with real world visual information to create a mixed reality display, so that the user may see augmented video with the manipulated images on the display of the glasses, lenses, or retina, which is then slowly merged back into a real world video matched as closely as possible with the real world unmodified vision of the user, all of which may combine in the mind to create one homogeneous corrected image.

In another aspect of this invention, the glasses or lenses may not be used and the image may be displayed upon smart contact lenses, which may receive the video from a remote source which may have received the video, manipulated the image, and re-projected the modified image onto the smart contact lenses for the user to see.

In another aspect of this invention, the lenses, such as wave guide projected lenses, mirror projected lenses, transparent OLED lenses, or film applied to lenses, such as 3M reverse projection transparent film, upon which the video or images are to be displayed, may be glued or similarly affixed to the user's corrective lenses, such that the user sees both the prescription corrected real world images along with the video projected augmented images, all of which combine in the mind to create one homogeneous image.

In another aspect of the invention, pixel algorithms may be used to use the outer boundary of the projected FOV to intersperse augmented visual information which, by skipping some, but not all pixels, may permit real world information to be viewed through the see-through glasses or lenses, a merging effect mixed reality may be created which merges the real-world images to the eye with the augmented video.

In another aspect of this invention, the prescriptive corrective lenses may be worn together with the mixed reality see-through lenses, without the same being glued or directly affixed. In this case the corrective lenses may have a mechanism to snap in or otherwise hold the corrective lenses within a close proximity to the augmented mixed reality lenses.

In another aspect of the invention, contact lenses, upon which augmented images can be viewed, can be used together with the user's own prescription glasses and/or lenses.

In another embodiment of the invention, this manipulated video of the real world may be displayed on see through glasses, and improvement over the enclosed goggles which previously existed, in order to merge manipulated video information with real world visuals.

The model view controller may be further configured to establish a border somewhere in the FOV as a function of data associated with the augmented visual model. The boundary may be indicative of an area to be corrected within the user's vision, wherein the area to be corrected may include more visual information than would originally exist in that same FOV in the real world. In other words, to correct for the user's limited FOV, the image or pixels from the area where the patent cannot see may be included into the FOV where the user can see.

In one embodiment of the invention, this may occur with reducing the overall size of the pixels to be able to include the manipulated pixels. In another aspect of the invention, the pixels may be the same size but may be managed pixel by pixel to include additional visual information.

In one embodiment of the invention, for instance in the case of correction and merging of augmented video with real world vision, a macular degeneration user may use interlaced video rather than progressive video protocols, and the removed pixels may reside in the alternate interlace.

The model view controller may be further configured to establish a retinal map as a function of the boundary and to store the retinal map in the database. The display controller may be configured to receive and to store the retinal map. The display controller may be further configured to receive an image from a camera or cameras associated with the user and to apply corrections to the image based on the retinal map and responsively generate a corrected image. The display unit may be coupled to the display controller and may be configured to receive the corrected image to present the corrected image to the eye of the user.

In other embodiments, a method is provided. The method may include the steps of establishing, by a model view controller, a visual model associated with a user and storing the visual model in the database. The visual model may include data related to a quality of the user's vision. The method may further include the step of establishing, by the model view controller, a boundary as a function of data associated with the visual model, the boundary being indicative of an area to be corrected within the user's vision into which corrected FOV where the additional pixels removed from the non-visual area of the users FOV are added.

The method may also include the steps of establishing, by the model view controller, a retinal map as a function of the boundary and storing the retinal map in the database, receiving, at a display controller, an image from a camera or cameras associated with the user, applying corrections to the image based on the retinal map, and responsively generating a corrected image. Further, the method may include the steps of receiving, at a display unit, the corrected image and presenting the corrected image to the eye of the user.

In still other embodiments, one or more non-transitory computer-readable storage media may have computer-executable instructions embodied thereon. When executed by at least one processor, the computer-executable instructions may cause the at least one processor to establish, by a model view controller, a visual model associated with a user and storing the visual model in the database. The visual model may include data related to a quality of the user's vision. A boundary may be established as a function of data associated with the visual model, the boundary being indicative of an area to be corrected within the user's vision. A retinal map may be established as a function of the boundary. An image from a camera or cameras associated with the user may be received at a display controller. Corrections may be applied to the image based on the retinal map, and a corrected image may be generated. The corrected image may be presented to the eye of the user.

INDUSTRIAL APPLICABILITY

With reference to the drawings and in operation, the present invention may provide systems and methods to stretch, skew, and manipulate the image being projected on the eye to avoid the vision impaired or unsighted portions of the macula, and be directed to the remaining central vision, sighted macular vision, and the near peripheral vision. The findings of the inventors are that the displaced pixels or images may be removed but replaced as near the original position as possible. In this instance, the central vision area typically may be said to comprise the central five degrees FOV of the eye, with the paracentral area being the most central either degrees of the eye's vision and the macular vision being the central 18 degrees of the eye's vision. Typically, with an AMD user, the eye defect lies within these areas. On the outside of the macular vision is what is called the near peripheral area of the eye, which may comprise the next 30 degrees of the FOV of the eye. If possible, since the receptors of the eye are the most similar to the central portion of the eye, the displacement of the pixels or image may be to the nearest possible near peripheral field of vision of the eye.

The whole foveal area including foveal pit, foveal slope, parafovea, and perifovea is considered the macula of the human eye. This is what is destroyed with macular degeneration. Familiar to ophthalmologists is a yellow pigmentation to the macular area known as the *macula lutea*. The *macula lutea* is thought to act as a short wavelength filter, additional to that provided by the lens. The fovea is the most essential part of the retina for human vision and contains short-wavelength receptors cells, medium-wavelength receptor cells, and long-wavelength receptor cells. Thus, the central approximate 10 degrees of the eye's FOV projects onto approximately the central 3 mm of retina, or a region within 1.5 mm radius of the fovea centralis positioned at 0° eccentricity. This is a slightly larger area than the region that contains the yellow macular pigments, which is 4 to 6° in diameter (*macula lutea*) or the macula. The foveola approximately coincides with the area of peak cone density in the photoreceptor layer, and in general is centered within a small region devoid of retinal vessels—the foveal avascular zone (FAZ). Thus, the repositioning of pixels or images may be concentrated onto the remaining non-defect areas of this region, as much as possible, as the cones in this region are so densely packed that they look almost like rods. Also, the relationship to the cellular structure and ganglia are on par with a more one-to-one basis than any other area in the eye, so that just making a hole bigger, if it ignores sighted portions of the *foveolar centralis*, may make a far less crisp picture.

Figure 25:
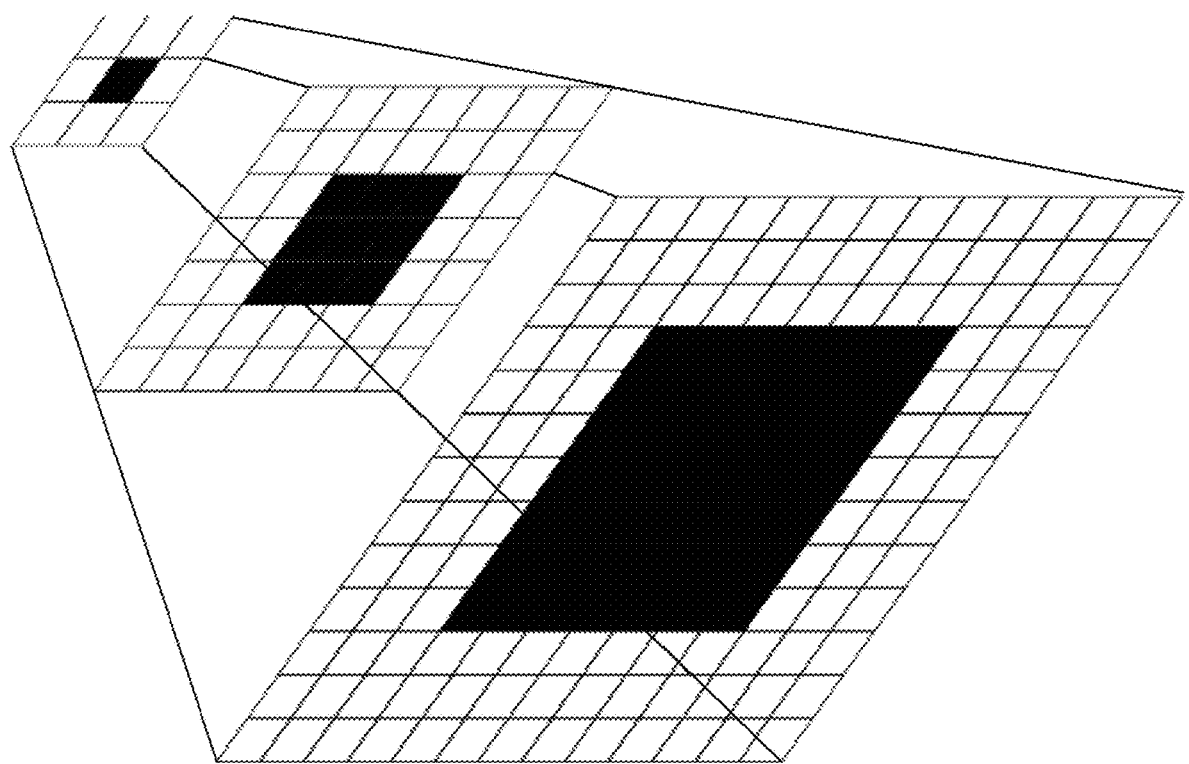
FIG. 25 is an illustration of subpixel mapping.
Figure 26:
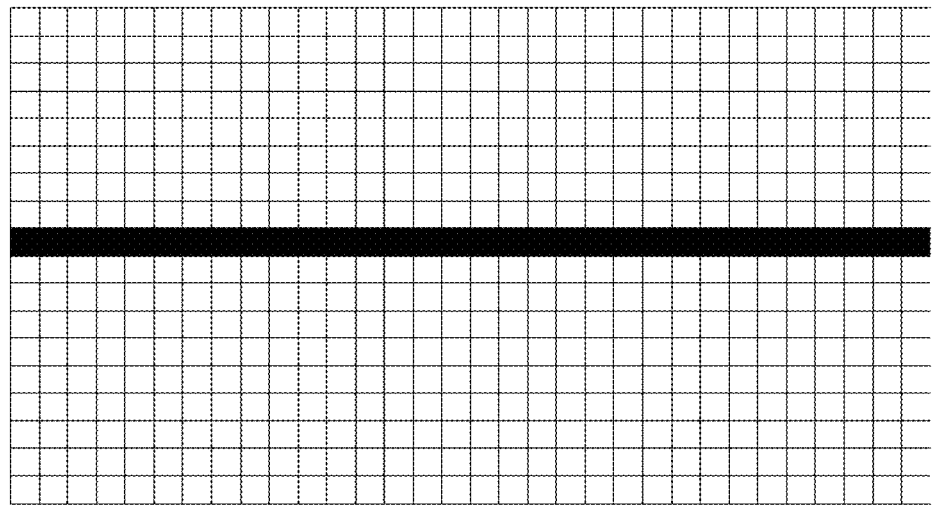
FIG. 26 is a graphical illustration of the corrected field of vision, showing the area of pixel manipulation.
Figure 26:
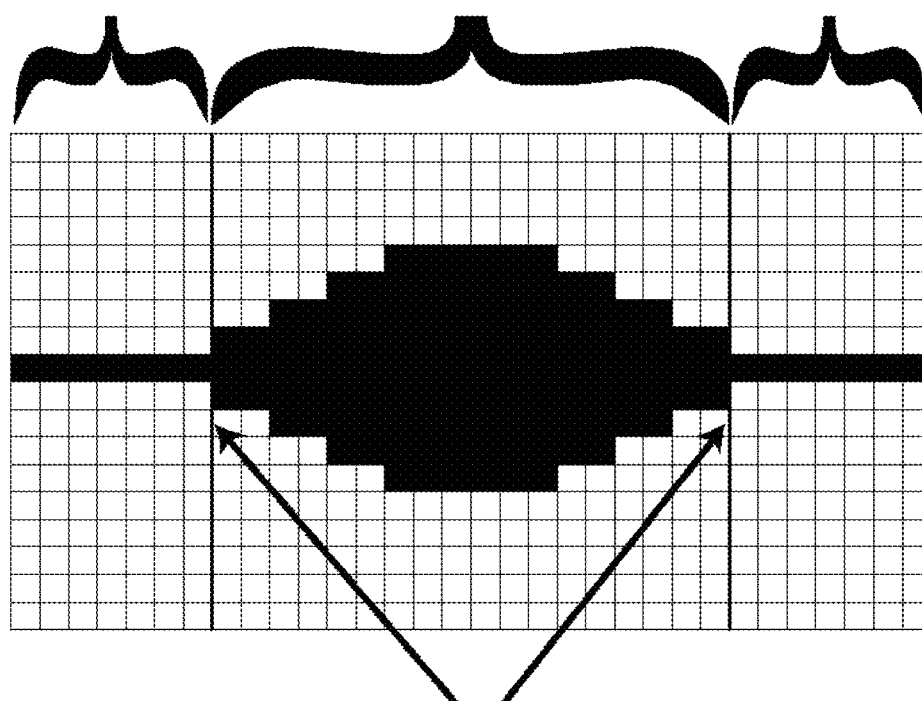
Figure 27:
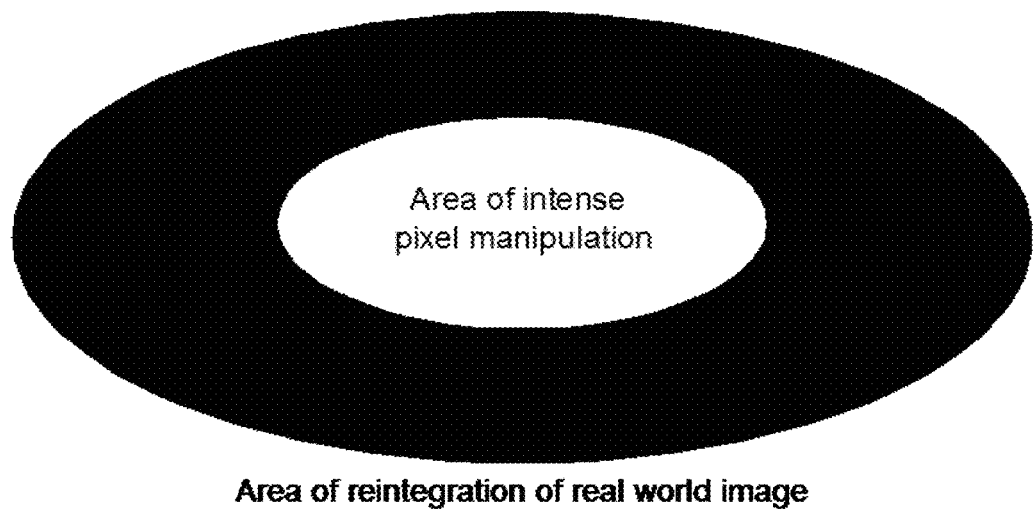
FIG. 27 is a further illustration of the corrected field of vision, showing the area of pixel manipulation.
Figure 28:
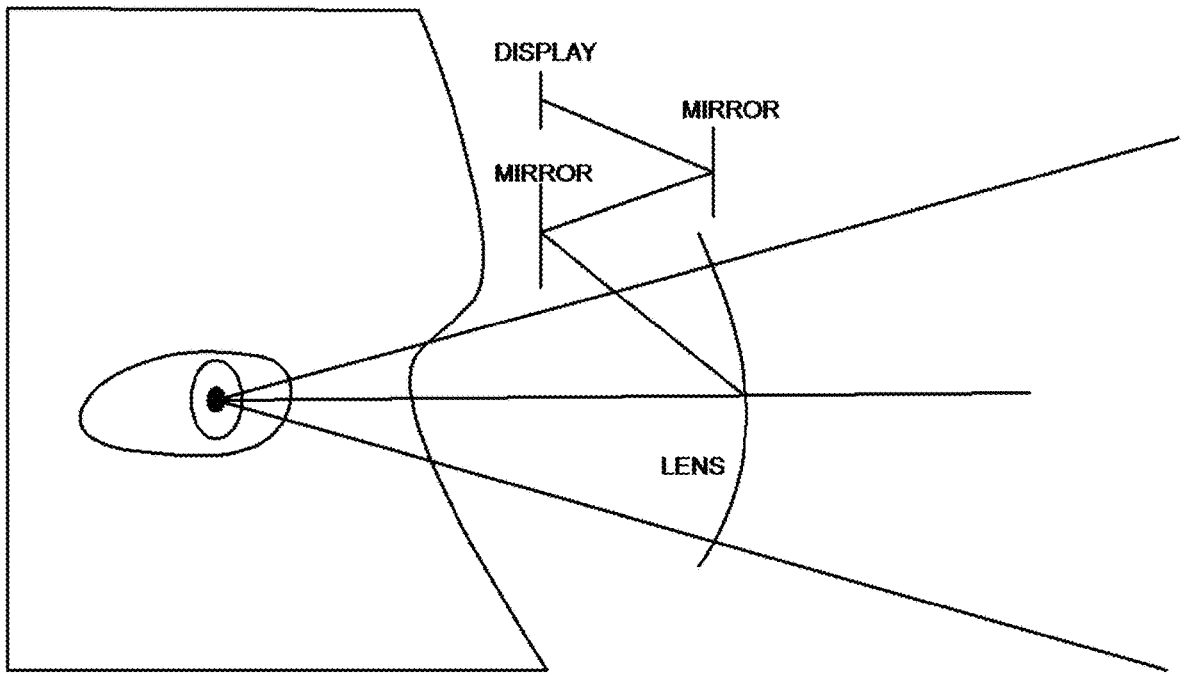
FIG. 28 is an illustration of the system with remote camera (top) and contact lens camera (bottom)
Figure 28:
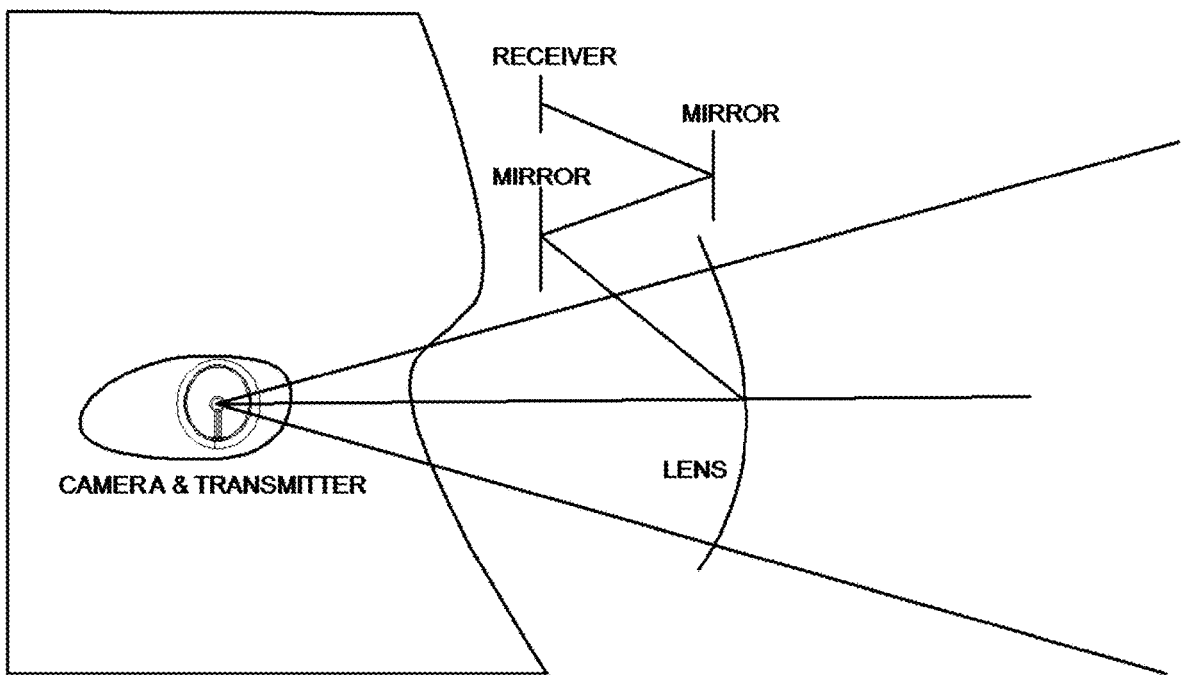
Figure 29:
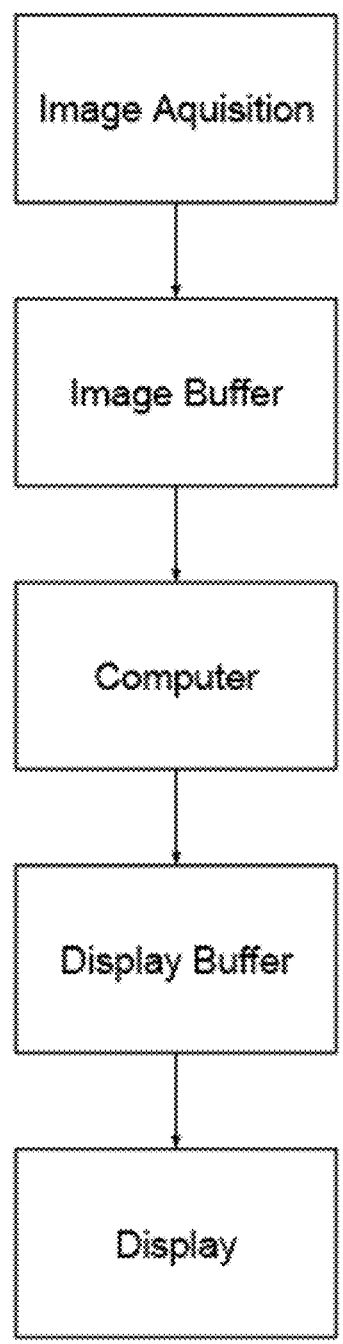
FIG. 29 is a flow chart of the process.
Figure 30:
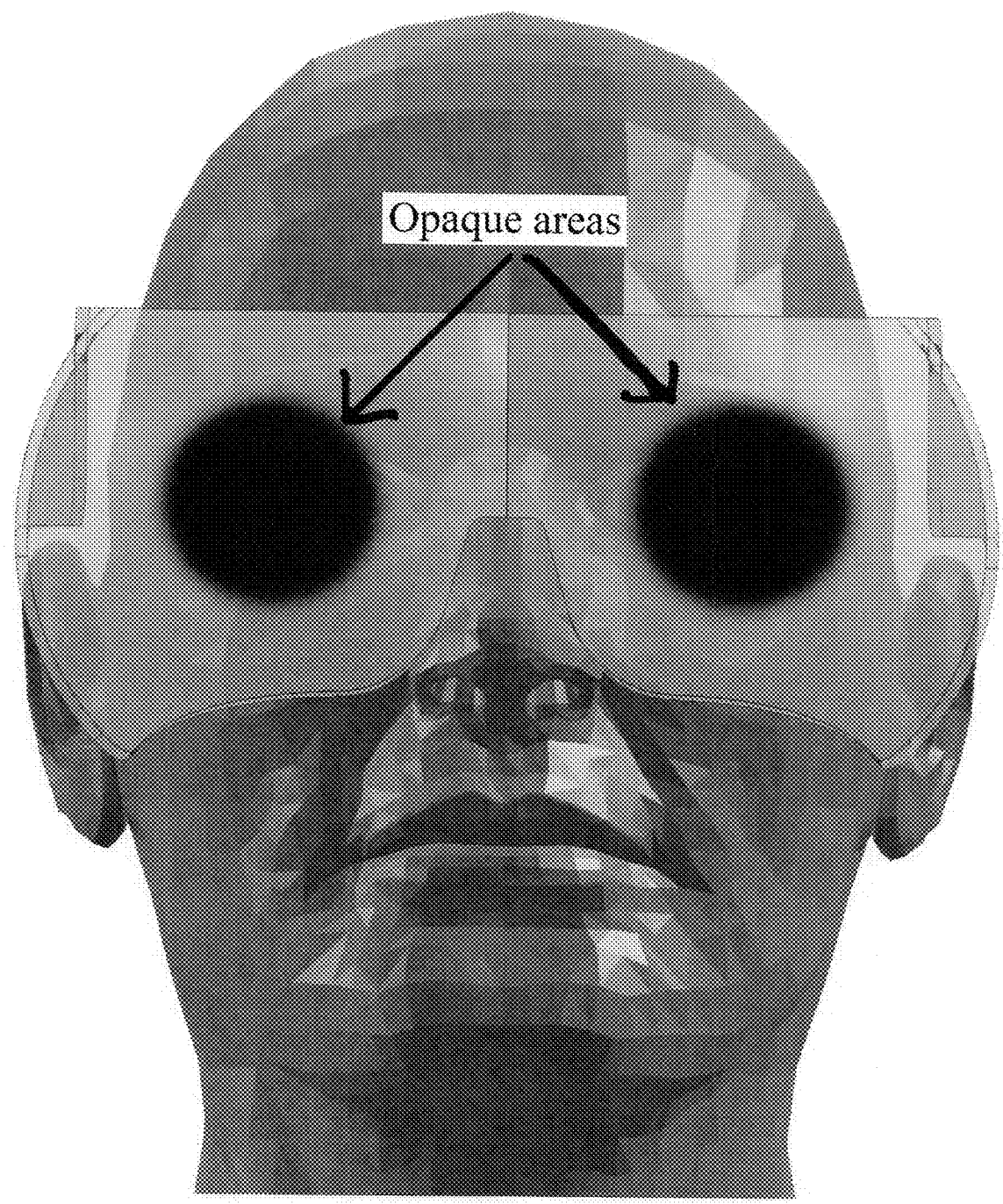
FIG. 30 is an illustration demonstrating dynamic opacity.

For this reason, the software may not just cut a hole as a homogeneous looking space, like an oval or a circle, but the software may as precisely as possible remove the pixels and images from the non-sighted areas and replace them in the next closest sighted areas, despite the highly irregular pattern this might demand. FIG. 25 depicts how this may be accomplished. In this way, the remaining sighted portions of the *foveolar centralis* and macula may be used to project the modified image to make the best use of this specialized region of the eye.

If the disease has progressed, where there are no remaining sighted portions of the macula or *foveolar centralis*, then the image may be displaced and projected on the closest nearest area with the highest concentration of cones which exists.

The distribution of rods and cones across the surface of the retina may also have important consequences for correction for macular degeneration. Typically, the total number of rods in the human retina, approximately 91 million, exceeds the number of cones at approximately 4.5 million.

As a result, there is a higher density of rods throughout most of the retina, while the cones are more concentrated in the central vision portion of the eye. Since daytime vision and acuity is highly dependent on cone-mediated vision, transference of the modified picture and video may be preferred to any remaining areas that contain the most cones for the best augmented acuity.

Since the relationship of cones and rods changes dramatically in the fovea (macula), a highly specialized region of the central retina that measures about 1.2 millimeters in diameter, this is the area of first focus for the repositioned augmented pixels and image. In the fovea, cone density increases almost 200-fold, reaching, at its center, the highest receptor packing density anywhere in the retina. The increased density of cones in the fovea is accompanied by a sharp decline in the density of rods. In fact, the central 300 µm of the fovea, called the foveola, is totally rod-free. Thus, one aspect of this invention may be to displace the pixels or image to as similar an area of the eye as possible, so that perception of the image by the eye is projected onto an area which is as close to the same as the damaged area, in terms of rods and cones, as possible.

To accommodate this specific displacement area, up to 15 degrees (typically a user does not have the entire macular area defective, at least in the early stages, so 15 degrees is usually an outside range with 5 to 8 degrees being more typical) additional pixels and images may be placed within the closest 30 degrees FOV to the unsighted area.

Alternatively, if no area exists where there is a concentration of cones, then the image may be moved to the next best place which is the near periphery and the retina's peripheral receptors. Alternatively, the image may be skewed to immediately adjacent portions of the retina in an irregular fashion that best approximates the area of defect. In this way, the entire image is projected on the functioning retinal receptors, and any involvement of the macula is avoided. The systems and methods, according to embodiments of the present invention, may create a distortion map of the entire image and project it onto the periphery of the eye, while avoiding the macula. This may be done by the use of computer aided 90-degree 3D or similar high definition goggles or glasses, or by photon projection with a virtual retina display of the image directly onto the retina of the eye.

In some embodiments of the invention, the method and manner of the skewed projection relies on external lenses, with up to 2 million pixels, a resolution seen only otherwise on ultra-high-definition TVs and tablet computers, which may provide the resolution needed to put the entire image on the peripheral retina receptors in sufficient detail to be analyzed by the optical nerve and brain.

Also, for the introduction of perspective, two cameras can to be used, and the modern goggles and glasses can accept more than one image interface and/or signal. Thus, the computed manipulated images may be captured in real-time and displayed in real-time for the user.

In addition, the goggles and/or glasses could be used to house a technology like virtual retina display, retina scan display projection, and/or a retinal projector technology, which all use photon on retina projection, which in this case may be modulated by the IDM (image distortion map) to the person's specific retinal map so that an intentionally distorted image may be projected onto the areas of the eye which have the best visual reception. In this fashion, the image may be projected directly into the portion of the peripheral retina which is still active in a macular degeneration user via photons, utilizing a technology such as a virtual retinal display (VRD), also known as a retinal scan display (RSD) or retinal projector (RP). When combined with these technologies, the person's specific retinal map, modulated by the image distortion map, may be displayed by the technology, which may draw a raster display (like a television) directly onto the retina of the eye, and in this case on to the usable portions of the retina of the eye. With the VRD, RSD, or RP, the user may see what appears to be a conventional display floating in space in front of them, which may be corrected for the loss of macula, but may still provide the user with the ability to see other peripheral obstacles, such as steps in front of the user which the camera is not yet focused on. In addition, the goggles and/or glasses could be used to house a technology like virtual retina display, retina scan display projection, and/or a retinal projector technology, which all use photon on retina projection, which in this case may be modulated by the pixel manipulation according to the person's specific loss of sight. In this fashion, the manipulated image may be scanned directly into the portion of the peripheral retina which is still active in a macular degeneration user via photons. These photons may be projected by cameras in the glasses or by smart contact lenses, which may or may not receive its information, energy, and connection from the HMD.

Another advantage is that these types of wide field-of-vision goggles or glasses can be used in conjunction with one or more cameras, which may be head mounted. Another advantage of these types of glasses is that they can be combined with proximity sensors, motion sensors, and head and eye tracking, a feature which is advantageous for understanding a user's specific field of vision for adjustments, and to measure distance through triangulation. For instance, in human eyes there is a convergence of the image when it comes closer to the face, meaning that the image captured by each eye begins to overlap the other eye's image. In 3D camera applications, this convergence is not always taken into account, and the sensors can also be used to automatically change the field of view presented to the retina, i.e., a virtual zoom to determine facial features when in proximate distance of another person. When used in conjunction with a user interface, the zoom, skew, or other manipulation features can be selected in a straightforward method chosen by the user to gain visual acuity in various environments. A differential adjustment may also be chosen with regard to each eye. Alternatively, software derived proximity and motion sensing can be employed by utilizing comparative techniques on sequential camera images.

Thus, this invention teaches that one camera may be used for monoscopic image capture and display. In addition, this invention teaches two cameras may be used to simulate true stereoscopic vision on the goggles/glasses display, wherein the IDM (image distortion map) model may include factor correction for epipolar curves, guided by the epipolar geometry so that stereoscopic vision, generated by two or more cameras, can be employed and be displayed, and seen.

The invention may use computer aided video images, which may be skewed and stretched in a matrix distortion or other similar fashion to put the most or the entirety of the image onto the peripheral vision of the user by opening up the center of the image and manipulating it to the peripheral cones of the eyes, as seen by the user in the projected image, in order to project the video captured images on the peripheries of the cones in the eyes where vision is still active. The benefits of this invention are that no invasive procedures are necessary and as the MD changes, the software can be adjusted so that the image is now correctly skewed. It is an additional advantage of this invention that live feedback can be provided.

In the fashion taught by this invention, the viewed experience may make it nearly impossible for the user to distinguish between what is actually seen and the image that is created by the distortion map.

Thus, the image may be spread and/or skewed multilaterally and then the corrected image may be reflected onto 3D or high-definition goggles and/or glasses worn by the user. The image may be skewed via the IDM (image distortion map) module to avoid projection to the area of the eye which involves the macula, but may still have all the image information. To imagine this process, think of a picture which is printed onto a stretchable and compactable substance. A hole is cut into the middle of the image and stretched open. This makes the image compress into the sides of the picture. Thus, all of the information of the picture is still there, it is just rearranged where a hole is in the middle and the image is moved each way to the side, top, and bottom. This hole-cutting may be done via algorithms and computer software/firmware technology, for instance, using a technology like image distortion mapping as above mentioned.

In one embodiment, the process may map each pixel in the two-dimensional image (or video) from the camera(s) to a new pixel location on the display. In another embodiment, only the data points are remapped. The other image data may be transformed using a predefined function that interpolates the data between the data points.

The IDM model may take vector values (numbers) that describe the lens center of the goggle device (per eye, on the oculus rift) (called "ICr"), as well as field of view of the display, and return the vector object that defines how to distort the image to make it more viewable by someone with macular degeneration. The key element may be to define the mapping between image (pixel) coordinates and 3D rays in the camera(s) coordinates as a linear combination of non-linear functions of the image coordinates. This may allow a linear algorithm to estimate nonlinear models, and create a method to distort the image such that there is typically a (circular) hole(s) or cut-out(s), or a geometrically distorted area in the center of the image accomplished by moving the pixel coordinates so that the entire image is distorted and mapped around the hole, which may be cut-out, or to compensate for the geometric distortion caused by leaking vessels. How this image is exactly cut-out and the pixels rearranged may be accomplished through testing with the subject so that it is attempted to use as many peripheral retina receptors as that subject has active. This image distortion map ("IDM") model may thus become that person's prescribed retinal interface ("PRI").

This invention has great benefits in that it is non-invasive, can be worn or not worn, and is easier to adjust and keep fine-tuned because it is external, and image and algorithms which stretch and skew the image to the PRI can be adjusted in real-time based on MD user feedback in adjustments.

In another embodiment of the invention, the active retinal receptors may be identified through evaluation with the system or by known prescription whereby the lowest number of receptors in the retina required to affect the desired mental and visual impression of the image ay be used to increase the apparent refresh rate, by actually increasing the refresh rate by displaying the image on less than all of the receptors.

In another aspect of the present invention, various FOV maps may be stored and/or analyzed or tracked in a database. The database may be stored in the cloud. A knowledge base and decision tree-based formula may be used to analyze the FOV maps, and one or more of the FOV maps may be used as a starting point for a user. The selected FOV map could be fine-tuned using one or more of the methods described above. A FOV from the database may be chosen as a starting point based on user visual models, common trends, and outliers within the data. The FOVs models could be sorted and/or chosen based on identified common boundaries. The output of the different FOV maps, i.e., the resultant corrected images could be analyzed, with user input, utilizing a process of comparison and elimination while viewing desired real-world images, i.e., a face chart, text chart, or the like.

A controller, computing device, server, or computer, such as described herein, may include at least one or more processors or processing units and a system memory, which may be an embodiment in a personal computer, server, or other computing device. The controller typically also includes at least some form of computer-readable media. By way of example and not limitation, computer-readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer-readable instructions, data structures, program modules, or other data in a modulated data signal, such as a carrier wave or other transport mechanism, and include any information delivery media. Those skilled in the art should be familiar with the modulated data signal, which has one or more of its characteristics set or changed in such a manner as to encode information in the signal. Combinations of any of the above are also included within the scope of computer-readable media.

The order of execution or performance of the operations in the embodiments of the invention illustrated and described herein is not essential, unless otherwise specified. That is, the operations described herein may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In some embodiments, a processor or controller, as described herein, includes any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term processor.

Whereas, the devices and methods have been described in relation to the drawings and claims, it should be understood that other and further modifications, apart from those shown or suggested herein, may be made within the spirit and scope of this invention.

What is claimed is:

1. A wearable mixed reality system comprising:
a camera input system;
an image projection system capable of being worn by a user; and
a processor in communication with the camera input system and the image projection system such that the processor is capable of receiving a real-world image from the camera input system and simultaneously displaying at least a portion of the real-world image and an augmented image on the image projection system such that a user views the portion of the real-world image and the augmented image simultaneously, where the processor is further capable of generating a shader based on input ansler grid data such that the shader is capable of manipulating the real-world image to produce the augmented image.

2. The system of claim 1 where the image projection system comprises a wave-guide display.

3. The system of claim 1 where the image projection system comprises a pico projector.

4. The system of claim 1 where the image projection system comprises one or more prisms.

5. The system of claim 1 where the image projection system is housed in a head mounted display and where the head mounted display is capable of being in communication with and controlled by a wireless device.

6. The system of claim 5 where the head mounted display is capable of displaying images and sounds from the wireless device.

7. The system of claim 1 further comprising a hand and finger gesture tracking subsystem such that the processor, the real-word image, the augmented image, or any combination thereof are capable of being interacted with by the user.

8. The system of claim 7 further comprising a drone, where the camera input system comprises at least one camera located on a drone and where the drone is capable of being controlled by the user via the hand and finger gesture tracking subsystem.

9. The system of claim 1 where the image projection system is capable of dynamic opacity.

10. The system of claim 1 further comprising an eye tracking subsystem capable of detecting abnormalities in eye functioning.

11. The system of claim 1 further comprising bone sound conduction technology.

12. A method of providing a mixed reality experience to a user, the method comprising:
   receiving a real-world image from a camera input system;
   loading ansler grid data and generating a shader based on the ansler grid data, where the shader manipulates the real-world image to produce an augmented image; and
   displaying at least a portion of the real-world image and the augmented image on an image projection system capable of being worn by a user such that the user views the portion of the real-world image and the augmented image simultaneously.

13. The method of claim 12 further comprising producing the ansler grid data based on user input.

14. The method of claim 12 where the image projection system is housed in a head mounted display, the method further comprising controlling the head mounted display with a wireless device.

15. The method of claim 14 further comprising displaying images and sounds from the wireless device on the head mounted display.

16. The method of claim 12 further comprising interacting with the augmented image via a hand and finger gesture tracking subsystem.

17. The method of claim 16 where the camera input system comprises at least one camera located on a drone, the method further comprising controlling the drone via the hand and finger gesture tracking subsystem.

* * * * *